United States Patent
Backman et al.

(10) Patent No.: US 11,584,966 B2
(45) Date of Patent: Feb. 21, 2023

(54) PIEZO TYPE MECHANOSENSITIVE ION CHANNEL COMPONENT 1 (PIEZO1) VARIANTS AND USES THEREOF

(71) Applicant: Regeneron Pharmaceuticals, Inc., Tarrytown, NY (US)

(72) Inventors: Joshua Backman, Tarrytown, NY (US); Aris Baras, Tarrytown, NY (US)

(73) Assignee: Regeneran Pharmaceuticals, Inc., Tarrytown, NY (US)

( * ) Notice: Subject to any disclaimer, the term of this patent is extended or adjusted under 35 U.S.C. 154(b) by 276 days.

(21) Appl. No.: 16/785,152

(22) Filed: Feb. 7, 2020

(65) Prior Publication Data
US 2020/0263252 A1 Aug. 20, 2020

Related U.S. Application Data

(60) Provisional application No. 62/806,932, filed on Feb. 18, 2019, provisional application No. 62/862,847, filed on Jun. 18, 2019.

(51) Int. Cl.
*C12Q 1/6883* (2018.01)
*A61P 9/14* (2006.01)
*A61K 31/192* (2006.01)
*A61K 31/616* (2006.01)
*C12N 15/10* (2006.01)
*C12Q 1/6827* (2018.01)

(52) U.S. Cl.
CPC .......... *C12Q 1/6883* (2013.01); *A61K 31/192* (2013.01); *A61K 31/616* (2013.01); *A61P 9/14* (2018.01); *C12N 15/1096* (2013.01); *C12Q 1/6827* (2013.01); *C12Q 2600/156* (2013.01)

(58) Field of Classification Search
CPC ................ C12Q 1/6883; C12Q 1/6827; C12Q 2600/156; A61P 9/14; A61K 31/192; A61K 31/616; C12N 15/1096
USPC .......................................................... 514/27
See application file for complete search history.

(56) References Cited

FOREIGN PATENT DOCUMENTS

WO 2020171982 8/2020

OTHER PUBLICATIONS

Glossary of medical education terms, Institute of International Medical Education. http://www.iime.org/glossary.htm Accessed in Mar. 2013. (Year: 2013).*
Smetanina et al. The genetic constituent of varicose vein pathogenesis as a key for future treatment option development. Vessel Plus 2021;5:19, pp. 1-13. (Year: 2021).*
Batchvarov et al. One-Year Diosmin Therapy (600 Mg) in Patients With Chronic Venous Insufficiency-Results and Analysis. J Biomed Clin Res vol. 3 No. 1, 2010, p. 51-54. (Year: 2010).*
Martin-Almedina et al. Human phenotypes caused by PIEZO1 mutations; one gene, two overlapping phenotypes? J Physiol 596.6 (2018) pp. 985-992 (Year: 2018).*
Bell, R. K., et al. "A large scale genome wide association study of varicose veins in the 23andMe cohort." The 64th Annual Meeting of The American Society of Human Genetics, San Diego, California, USA. 2014. (Year: 2014).*
Anonymous, "16_88727995_G_A Open Targets Genetics", 2018, https://genetics.opentargets.org/variant/16_88727995_G_A.
Anonymous, "16_88730362_G GGGAGGC Open Targets Genetics", 2018, https://genetics.opentargets.org/variant/16_88730362_G_GGGAGGC.
Fukaya et al., "Clinical and Genetic Determinants of Varicose Veins: Prospective, Community-Based Study of ~500?000 Individuals", Circulation, 2018, 138(25), pp. 2869-2880.
Shadrina et al., "Abstract; Supplementary table 2; Supplementary table 3; Suppl. table 5A", bioRxiv, 2018, http://www.biorxiv.org/content/10.1101/368365v1.
Shadrina et al., "Varicose veins of lower extremities: Insights from the first large-scale genetic study", PLOS Genetics, 2019, 15(4), pp. e1008110.
International Search Report and Written Opinion dated May 25, 2020 for International Patent Application No. PCT/US2020/017267.
International Search Report and Written Opinion dated Nov. 9, 2022 for International Patent Application No. PCT/US2022/073441.
Douguet et al., "Piezo Ion Channels in Cardiovascular Mechanobiology" Trends in Pharmacological Sciences, 2019, 40(12), pp. 956-970.
Van Hout et al., "Exome sequencing and characterization of 49,960 individuals in the UK Biobank", Nature, 2020, 586, pp. 749-756.
Botello-Smith et al., "A mechanism for the activation of the mechanosensitive Piezo1 channel by the small molecule Yoda1", Nature Communications, 2019, 10(4503), pp. 1-9.

* cited by examiner

*Primary Examiner* — Yih-Horng Shiao
(74) *Attorney, Agent, or Firm* — Armstrong Teasdale LLP

(57) ABSTRACT

Methods of treating patients having varicose veins, methods of identifying subjects having an increased risk of developing varicose veins, and methods of diagnosing varicose veins in a human subject, comprising detecting the presence of Piezo Type Mechanosensitive Ion Channel Component 1 (PIEZO1) predicted loss-of-function variant nucleic acid molecules and polypeptides in a biological sample from the patient or subject, are provided herein.

8 Claims, 6 Drawing Sheets
Specification includes a Sequence Listing.

Single-point and aggregate results for the 65 pLOF variants in PIEZO1

| Single-point analysis | | | | | | | | | Drop one - RVT | |
|---|---|---|---|---|---|---|---|---|---|---|
| SNPID (rsID) | Ref | Alt | AAF | Beta | SE | P-Val | MAC | Functional Effect | P-Val LOO Burden | Delta P-Val Burden |
| 16:88727163:G:A | G | A | 6.9E-05 | 2.81 | 0.88 | 0.001 | 6 | stop gained | 1.06E-06 | 33.91 |
| 16:88721586:G:C | G | C | 1.1E-05 | 14.63 | 119.5 | 0.903 | 1 | stop gained | 2.63E-07 | 8.45 |
| 16:88716874:G:A | G | A | 1.1E-05 | 14.40 | 119.5 | 0.904 | 1 | stop gained | 2.59E-07 | 8.31 |
| 16:88738735:D:1 | TC | T | 1.1E-05 | 13.95 | 119.5 | 0.907 | 1 | frameshift | 2.45E-07 | 7.86 |
| 16:88721268:D:1 | CT | C | 1.1E-05 | 13.90 | 119.5 | 0.907 | 1 | frameshift | 2.43E-07 | 7.80 |
| 16:88726546:C:T | C | T | 1.1E-05 | 13.67 | 119.5 | 0.909 | 1 | splice donor | 2.34E-07 | 7.49 |
| 16:88723253:G:A (rs368895635) | G | A | 2.3E-05 | 3.77 | 1.42 | 0.008 | 2 | stop gained | 2.31E-07 | 7.42 |
| 16:88719588:G:A | G | A | 1.1E-05 | 13.57 | 119.5 | 0.910 | 1 | stop gained | 2.29E-07 | 7.35 |
| 16:88720229:C:A | C | A | 1.1E-05 | 13.55 | 119.5 | 0.910 | 1 | stop gained | 2.28E-07 | 7.32 |
| 16:88727072:D:1 | TC | T | 2.3E-05 | 3.59 | 1.42 | 0.011 | 2 | frameshift | 2.22E-07 | 7.12 |
| 16:88716359:A:G (rs776709730) | A | G | 2.3E-05 | 3.15 | 1.42 | 0.026 | 2 | splice donor | 1.94E-07 | 6.23 |
| 16:88736324:G:A | G | A | 4.6E-05 | 2.48 | 1.18 | 0.035 | 4 | stop gained | 1.67E-07 | 5.35 |

Figure 4

LD Assessment for PIEZO1

| Variant | LD(R²) | 1 | 2 | 3 | 4 | 5 | 6 | 7 | 8 | 9 | 10 | 11 | 12 |
|---|---|---|---|---|---|---|---|---|---|---|---|---|---|
| 1 | 16:88716359:A:G | 1 | 1.1E-9 | 1.1E-9 | 1.1E-9 | 1.1E-9 | 2.1E-9 | 1.1E-9 | 2.1E-9 | 6.3E-9 | 4.2E-9 | 1.1E-9 | 2.1E-4 |
| 2 | 16:88716874:G:A | | 1 | 5.2E-10 | 5.2E-10 | 5.2E-10 | 1.1E-9 | 5.2E-10 | 1.1E-9 | 3.1E-9 | 2.1E-9 | 5.2E-10 | 2.1E-5 |
| 3 | 16:88719588:G:A | | | 1 | 5.2E-10 | 5.2E-10 | 1.1E-9 | 5.2E-10 | 1.1E-9 | 3.1E-9 | 2.1E-9 | 5.2E-10 | 8.1E-6 |
| 4 | 16:88721268:D:1 | | | | 1 | 5.2E-10 | 1.1E-9 | 5.2E-10 | 1.1E-9 | 3.1E-9 | 2.1E-9 | 5.2E-10 | 8.1E-6 |
| 5 | 16:88721586:G:C | | | | | 1 | 1.1E-9 | 5.2E-10 | 1.1E-9 | 3.1E-9 | 2.1E-9 | 5.2E-10 | 8.1E-6 |
| 6 | 16:88723253:G:A | | | | | | 1 | 1.1E-9 | 2.1E-9 | 6.3E-9 | 4.2E-9 | 1.1E-9 | 1.6E-5 |
| 7 | 16:88726546:C:T | | | | | | | 1 | 1.1E-9 | 3.1E-9 | 2.1E-9 | 5.2E-10 | 2.1E-5 |
| 8 | 16:88727072:D:1 | | | | | | | | 1 | 6.3E-9 | 4.2E-9 | 1.1E-9 | 1.6E-5 |
| 9 | 16:88727163:G:A | | | | | | | | | 1 | 1.3E-8 | 3.1E-9 | 2.8E-5 |
| 10 | 16:88736324:G:A | | | | | | | | | | 1 | 2.1E-9 | 8.6E-5 |
| 11 | 16:88738735:D:1 | | | | | | | | | | | 1 | 8.1E-6 |
| 12 | 16:88835345:G:A | | | | | | | | | | | | 1 |

Figure 5

SEQUENCE LISTING

```
<160> NUMBER OF SEQ ID NOS: 4

<210> SEQ ID NO 1
<211> LENGTH: 69883
<212> TYPE: DNA
<213> ORGANISM: homo sapien

<400> SEQUENCE: 1
gggagccgcc gtccggccca gctcggcccc agtgagccga gcgctgcgct ccgccgaggg      60
gcagggcggt cgcctgagcg agcgcgggcc cgggacgtcg gcaccggcgg ggcggccgaa     120
ggagaaggag gaagaggaga aggcggcgcg cgggtccccg cgggtcagcc atggcgcgcc     180
ggccccgggg cccccgcacc gccccatagc gccgcggcgt ccgctcggtc tgggccgggc     240
cctgggccct ccagccatgg agccgcacgt gctcggcgcg gtcctgtact ggctgctgct     300
gccctgcgcg ctgctggctg gtgagtgggg ggcgggcgcc tgggggcgac gggaggggc     360 tgcgtctcgg ctccccacgg cctggacacc ggacgacgcc ggccggggcg agggctgcgg     420
gcgagcgggc gcggaaattc ccagggacgc gcgacccggg cgcccgcatt cctgaagcat     480
gagcgcgcca ggcggcggcg gggctcctgt cccagggccg ggctggaagg gcggcggcgg     540
ctgggggaga cggcaccgcg tgcccacggg ggcggtcgag cgagcgccgg gcatagcgcg     600
gctggcgtct ccgccggggc gctgcggaga ggaggccgcc gggcgaggcg gtgtttgccc     660
cggtgggaag ggccgcggcg gtggtggggg gagcacgaat ctcttttttct ctttcgggtt     720 taaaaaaaaa agcgcaaagt tgcatcagga cttcctgaca atctgggaga aggcgggctt     780
```

```
cctgcctgga gctgtttaat ttggagcttc ccgagcccaa cgaacgtccg tgcccagggc    840
ccagccccgc tcaccgctgc acccccctct gccggactga ggcggtccca cactttggaa    900
aaaaatagtg tgggttcctc cctggtcctc ccttgcccta ctgggctcag tttcgcaggg    960
gcggggggccg gcctctgccc tggtctgggg gaggggacac cccggaggc tgtggcctgg     1020
tgtcagggcg gggcagggt ccccagtcct ggcatctgtg ttccctgctt gccgggcagt     1080
ggtgccctt tcgcgaagca cacccggtg gcttggtgct gcacggcctg gcaccctac      1140
ccttccccga ccctggccta gccgggaccc agggtccgcg ccctccgccc ggggctccc    1200
cacgtgtgat tgatctggga agcagtcgga tggaattaac ccacgacaa gtgggacggt    1260
ttgcattggg agtccgccat ggacacggca ggtggggcct tttgattgta aaagcccttt    1320
cggagcccctt gcctcgctcc agtgggagc tcgcccagcg ctagctttgg ggatctagag   1380
ccgcctgcct gaggctccca gacagactgc gttttgatcg gtcgcacaga aggtggtga    1440
aacttgggga gattttcta gacaggaatc aatgaaaacc attgaggctg gagaggagag    1500
gttttgagca actctcttca gtgcggtcag ccctgtgtgg actgggcagc ctgggacctg   1560
ctcccagtgc agggtcagat gggccgtaaa cagggcccgg ctgtgttcct tcctgtgcct   1620
tgaaaacaag caggacagcc tggcacagag gcagagtcta gagctgacag gccttagaga   1680
gggaaacagg aaagcttctg aaacgtcccg ttcacactga tcgttccatt tcctcttgtg   1740
tctgagtggg agcgggtgtc ctccctgcag ggaatgcccc cctctcaga tggcagctgc    1800
tccttgggca gagttggcaa tgttttctt taaatgacca gatggtaaat attttcatgt    1860
cacaaaatct tcttcttctg gtattttcc agccattaaa tgtaaaagcc ctcctgagtt    1920
catgggctgt acctaaacag gtgttgagcc cgattctgtg gcacatgtgg tttgctgccc    1980
cctgggcatt ggtcagggg cctgggttct gccttctcga ttgctatccg cgtggggat     2040
ctggggagg gatcactgtt cttcttgctt ttggcctcct tggggaggat ggggaggtag     2100
cccagggtg ctcacccagg ccccgtgtca gtcttctatg aaactttaa agaatagtga      2160
tgactgactg tctgtctgta tggtactttc cttaaaccta aaactggtcc caaataaagt   2220
ctcttaattt gaaagatgct gaagcccggg ccataccca cactgattct gtgtctgggg    2280
atggggcgtg gggcctgggc ctcactcagt gttttctctc agtcacctgg gggagatgga   2340
agtggagccg gccaagaacc ctgcctgcct gcctgctggc cgggactcct gagtcaggct   2400
ctctggccct ggggtgtggg cagctccaga tggacccgcg atgtgcaggt tcagctggcc   2460
tggccggagg tgggacactg gctttgctgt ctttggagtg cccctccct ctctggcgag    2520
cttcggctgg aagcagttct accgtgtttt ggaaatgaat gaggccttca gaaggcatta   2580
gtcagtgtgt gcctgcgctg gctcagacag tgcctggtga gggtttgagt catcctgggg   2640
tgccctggc ccccacgccc tccctctcca gtgcaggatc attacccaaa aatctggcag    2700
ggagctgccc cacccacagg gagcagggc ctccttcagc agtctcacct aatgttgctg    2760
gagccttggg ggatcagggc ccatctcttc tagagagatg tcaggcagg gctgggcgcg    2820
atggctcaca cctgtaatcc cagagcttcg ggaggccaag gtgggaggat tgcttgagcg    2880
tagccattcg agagcagcct gggcaacgta gagatcccca tctctatgaa aaatatttaa   2940
aaattagctg gcatggtgg tagtgcacct gtagtcccag ctactcagga ggccaaggtg    3000
ggatgattgt ttgagtccag gagttggagg ctacagtgag ccatgattgt atgactgcac   3060
tccagcctgg gtgacagacc ctgtctcaaa aagaaaaag gaaaaaaaag ggcaggacat    3120
ttgtgattct gataatatgg gaccgcacct ccagttctat cagtgggaaa tctagacagg   3180
```

```
gctgcggaaa gccagctggt gcgagaggag ccaccgtgtc actgactgtg ggacacccac    3240
gtgggctgac aatatggctt ctgcttttca gggtgcctcg tggcacagcc tagggcaca      3300 cccacggccg gcaagctggg cgtcacctcc ttcaggctga ttgtcactga gaagtgtcac    3360
catttagcat gagggatgct gcctcctttt tcagaacatt gtcaccatca gggtctcacc    3420
actcctggga ggcggccgag aagctgggga acagcaggca ctcggctcac agttgctcag    3480
cagtgcagac cctctgagct gagcatggca gagtcaccct tcggaggcct gtgcccgggt    3540
ctcaggacct gcacagaacc ctggcctgtc ccatccgagg gtgctgggaa gagcatggcc    3600
gtggcagagt agggtgggag ctgctttcct ctgtggcttg ggggcccctt ctgagcatca    3660
gctccctggt gtgacagagg ggcgcactct gtccccatgc tgggcctgga ggctggatga    3720
gtcagcagga gagcctgggg cctgcctcac agcaccaagg gctgcaggtg tgagtgtgca    3780
catgtgtgcg tgtttgggga aggggccagg gactgcccag gagctgagga tgggtcacag    3840
cgggtgctcg tcccgcagcg ggtcactggt gcccaggaca cagggagctc cagccccagc    3900
tgccagggtc ccacagagag gaagtttcct ctggggtgg gtgggggcgc acagtctctg    3960
atcctggccc caaggcagct tcctgggcgg tgtctctcct gtgctgactc ggcagtgcat    4020
ttgctttcgg tgctcaaaga tgaaggggaa ccaccgtggg ccttgacggc ctcatctgcc    4080
cgctgcagcc cactcctgag atgggaccac cgcagtcgtc agggtccagt gagagccgca    4140
tcttgcagga agccattcct ggcctctctg gcctcagaaa tccccttttc aattcaacaa    4200
aatgttagtc ttctgtttag ctattttaga aatagacagt taggcttttt tctcttttt     4260 cttaaagaca gaggctcact ctgtcgccca ggctggagtg tagcggcgtg attttggctc    4320
cctacaactt cagcctccag ggctcaagcc atcctcctgc ctcagcctcc tgagtagctg    4380
agattacagg tgtgtagcac catacctaat ttttgtattt tttgtagaga cggggtttca    4440
ccactttggc caggctggcc ttgaactcct gaccttaagc gatctgcccg cctcagcctc    4500
caaaagtgct ggggttacag gcatgagcca ccgcgcccgg ctgacagtta gacttttgct    4560
tctttgttta tataagcttt ttcttctggt tccaaaagca agtttgccct tccttgtggt    4620
agagaatcct agctcacaga gcagtttaga agccagcaca gtatcccaca cacacatctg    4680
gcatggacag acccttcctt gctgggtgtg ggtcctgtgt tcttctgaaa ggcaagctgt    4740
tcccagccaa cccctgcccc tctctgcctt agcctgcctg gaggcctgag tctcctgggt    4800
gactgtgagg tgggacccc ccttccccta cccccaccca catcctctgt atctgccttc    4860
tgtcctgctc ttgacctttg agctcctctg ctggcttcag ggtgcggctg ttgagcctat    4920
tttttggatt aggactctgg ggtgagggaa gttaattcac acacccaaga tcacactggt    4980
gggaagggac aggcccgggg tgaaggcttc tcctctcctt ggcggttgag tcccacacct    5040
gctggccgag gcacctgaag gggacttggg gtccagggtc actgggagga cggggcagg     5100 cagaggggtg gccgacctgg tggcggctcg tgggcagcag ccgaccctat cttgctctga    5160
acgtgtgggg ccctcacccc cttctctggg tctgggtttc ctcccctgta agtgacaccg    5220
taaaagcttc acagccgctt ccaagtctca ggtctctcgg gctttggatc tcacacccag    5280
gctgggtggg ggtaggggcg ggacagccgt ccccccgga aggctcagaa ttcctcgcac     5340
aatcgtgggg ccaggagacc cgcaacacag gctttcccag ctgcgctgag tgccgcggtg    5400
gccgggggtc cgtcgggcct ccatggagct gagggaagg ggccactcac cgcctggtcc     5460
cggagcacac agggcagctc ccaggagcac agaggctcct tgggacctgt ggggctgtcg    5520
```

```
gcctccctca tgctgcacac acagcgcgtc cccaggggtg tctgcagccc agcccatccc    5580
actgcagatt cccgaccact cagattcatt catgcatcct ctcacgccgg tcctgtggga    5640
cagagctctg ggcagcagcc agaagtccaa gttctggttc agggccagtg gaggtgggtg    5700
ttggggtggg gctggagctc cctgctctcc ctcccaagct agccaggaaa ggaggttggg    5760
ggccccgcac ggtcattgct gtttattcac aaagcgcgat gctgagcaca ggcggggaaa    5820
gaaaagtgcg atcagtgcca ggaaaatggg gctcccccga cgccgtccaa aatgggatcc    5880
cttgccgggc gcggtggctc acacctgtaa tcccagcact ttgggaagcc gaggcaggtg    5940
gatcacctga ggtcaggagt tcgagaccag cctgaccaac atggcaaaac tccatctcag    6000
ctaaaaatac aaaaattagc tgggcatggt ggcgggcacc tgtattccca gctgggaagg    6060
ctgagacagg agaatcgccg gaacccagga ggtagaggtt gcagtgagcc acagtcgtgc    6120
cactgcactc cagcttgggg gcttggggga cagcaagact ccctctcaaa aaaaaaaaaa    6180
aaaagtgaag tcgtaaatca gattaaattc ccttttaac cctttgaacc tctgtcctcc    6240
cctgttccca gcgggaagcc tctggtgaac gcgccatgca ccccacctgc cccgctctc    6300 tgggtctctc tcccagctgg aacggccgct tccccaggtg ccttccctgg gccacagcct    6360
tgtgcctcgg cggctgctgg atgcctgggt gtgtgggtgg ctcccagtgt gtgggatggc    6420
acacgagcct ctcgcccttc tgtgtggggt cgcacaccca ccgcaggccg tattttgct    6480 cacgttcatg tttctccacg gtggacgctg ggttgcaggg acccttcctg tgtgcgggtg    6540
aggatctggg cagctgctgg tgccgggccc atggggacgc tgaccgtccc gggtgccggc    6600
tctgaggtgt gcagtggacg gctgtcctgc cgggcgctgc cagggcccct taggccgacg    6660
tgcgtggcca cccgattccc cgccgttgtc tcaggaacct tgccgagtg ggtggatca    6720 atttttcggt tgtgttttaa tagcataatt acagggagta tttcaggctc cctctgacgg    6780
gccggcaggg tttggctgcc ggctgtttac caggctccaa tctgcacact attttttctgt    6840 gggtatatat agctggggct gcttctcctt cctcaggttc aggctaaaga gggacagcag    6900
ccgcctcagc cacccctgt ggtttccttt gcctgtggat gggcggctaa aatgggccca    6960
ggaagagtca agaacaaggc cggctctcgg tgccacagct ctaccccaa aagcaggaag    7020 ggggctcggg ccatgcccat ctgtgagcta caccggtccg ggagcggcat caggcagggg    7080
agtcctggac ccccgcagtg ctggggtgtg tttgtccgcc ctccctcccg tgtgtctaga    7140
agcctccagc ctcggggaaa acaatgaaac tcaactgtga cttaaacaga ttcccaggcc    7200
cgcaggagct cccggaggct tgtggctgtg gcgagacctg gagggccatg cgggagggac    7260
agacgcaggt ttgcggaggc cgcctgccca ggaggggcgt caaggagggg acagatgtg    7320 ggtttaggga ggccacctgc ccgggaggag cctcgaagga aggcacaggc gtgggtttgg    7380
ggctgcctgc cctggagggg cctcaaggac cccaggtctg gtcttggtct cactcacctc    7440
ctggaccccc caaggcctgc agtttgcaat ctgtcgcctg gaccccac tgtctgcctt    7500 tacgcagctc agccaccacg cggccctcgc tccctcattt acttgatttc tgtttatggt    7560
taaagtaccg tttaaaacga cacatcatta aagcaacatg aaaggagtt ttgaaaaggg    7620 aagccatcgt ccatcccact gcccctgcct cagcgggat ttacttttcc tttcctgtct    7680
gcgggccagt gacaatgagg accccgcaat gtgtctgcgg gccagtgaca atgaggaccc    7740
cgcaatgtgt ctgcgggcca gtgacagtga ggaccccgca atgtgtctgc gggccagtga    7800
cagtgaggac cctgcaatgt gtctgcgggc cagtgacaat gaggaccctg caatgggcgg    7860
cctgtaaggc tctgccctgg cctccgctgc cttcgctttc tccctccttg gtgggtgcac    7920
```

```
gcccttgtgc ttttcctaaa agagcaggtc ctccgggcat ggtggctcac gccggtaatc    7980
ccagcacttt gggaggccga gacgggtgga tcccaaggcc aggagttcaa gaccagcctg    8040
gccaacatgg caaaaccctg tccctactga aaatacaaaa attagctggg tatggtgaca    8100
ggcatctgta atcctagcta ctcgggaggc tgaggcagga gaatcacttg aatccgggag    8160
acggagtttg cagtgagccg agatcacacc attgcactcc agcctgggca acaagagcga    8220
aactccatct caaaaagaa gaagaagaaa atcctgacac ttcagcctgg tgcaggccct    8280
tccctccttc tagtccctgc caagaagtga gccgggccca gatctcctgc cgggcgggga    8340
atgagcacac acattcccct cttgggacag acagcagcag cagccctgtt gcacacatga    8400
ggacgtacag gctcaggggc cgtgggtggc agagaggcta tcagcgccgg actggcccgc    8460
cccgagccag ggtccagccc cacagtcctg tccccaagcc ctggcccttc tgcggtcact    8520
cccgtctgct gaatccccta ctctgcccct ggtgtgtggc cccccagttc cctcctgtgt    8580
tcattccctg ctaacctccc gtggcttcgc ctccccagat gccctgagca cacagcctct    8640
ccccttcctc ccctcctaga tgtgcacata ggagccgccc aaaggctggg gcagctagtg    8700
gggcccctcc aagggaagct gggccccggg caatgccctg agccaccagg tcctggccct    8760
gcgtctcatc ccttcttttt ttttttgag acagagtctc gctctgtcgc cctggctgga    8820
gtgcagtggc ccagtctggg ctcactgcaa gctctgcctc caggttcac gccattctcc    8880 ttcctcagcc tcccgagtag ctgggactac aggcgcccac caccacactc cgctaatttt    8940
ttgtattttt agtagagacg gggtttcacc gtgttaacca ggatggtctc aatctcctga    9000
cctcatgatc cacccgcctc ggcctcccag aatgctggga tgacaggcgt gagccaccgc    9060
gcccggcctc atttggttcc ttctgtgcac cacagtgtgg gatctcgggt cctgggtggc    9120
acgtgtttaa cctgaaagga aactgcccct gcgctcccca gcttgtagcc cgtgggcctg    9180
gctctgaggc cccgactgcc ccacggcctg tgctgcgcat gctggagcca ggctccggct    9240
ctggttggcg cctcccgtgg ctttaatctg cagtgacctg ggtgcttaac gagggccttt    9300
gcctctgcgt gtgcactgcc ttcttctgag gagtctcctc aagtctccca gctgtttaaa    9360
caatggggtc ttttgtcttt tgacctgttg gtgccatcag ccagcctcct gcacatactc    9420
tccctaccct tggctgccac tcctgtcctg cccttcgcca tgtctttttt cttttctttt    9480
tttttttttt ttttgacagc gtcttattct gccaccagg ctgtagtgga gtggcacgat    9540
cttggctcac tgcaccctcc gcctccctgg ttcaaccgat tctcctgcct tagcctccca    9600
agtagctagg actacaggtg cccaccacca caccggcta ttttttgtat tgttagtgga    9660
gatggagttt caccattttg gccaggctgg tctcaaactc ctgaccttag gtgatccgcc    9720
tgccttggcc tcccaaagtg ctgggattac aggcgtgagc cactgcgccg gcccccgcc    9780 atgtgttttt aagagcaggc atttcattca gatgaagccc ggacactctt gggggttctg    9840 ctcagggct ctacctgcca ctgaacgtcc tctccctgtg tgggtggcca tggcattcag    9900
cctgtgttgg gccttgttct gcctggctac tggccgctag gtctgccccg gcatcctctg    9960
tgtcctgtgt gggcgcctct gcctcctgct ccagcctgtg ccaggcaatc ctgctcacct   10020
tccaggagcc aggcctctcc ccagggcctg cgtcctgtca gggtcaggga cggcccctct   10080
gccatgctcc ggagtccctg gtcccctcac tccgttacgt cctgggtgtc acgggtacgg   10140
ccgggaactc tgtcgtcttc actgtctggg ccggggcctc cctgggtgtc tgctggatgg   10200
agtgggtgcc tttgggtccc tgcaaagtga gcctgcctcc cagcaccgcc ctgtcgttac   10260
```

```
atagccacta tctttgcgcc tgttttcct  tcctttgact ggttcctctg ggttaattc   10320
ccaggcctgg tattaccatc tctgaatgcc tgggtggttt cagcgcccag gaggctgtgc  10380
tgaggtatct tagaccatgt gggcaccgtt cgctcctgcg cagccggctc cggggtgccc  10440
tgttttgcg  gaatcctgca gggaacccca tgtaccctaa gagtgctctc cccagccact  10500
gtggcataag acaagcggtc tctttgccct tgggccccat ccttgtctgg tcggccttc   10560
ttcatgggtc cagcgcggga ttgccggctt ccttttcagg cttcctggga cccccactca  10620
gacctgcagc tgggccagcg atgcccaccc gtttctcctc cacgtggtat acagaggtgc  10680
ccaggctgct gctggggact ctggagccca ggagtgagtc tccttgaccc tgagctgtcc  10740
tggctatcac agctgggtcc tgttttcccc ttcagcaccc acgggtgtct ttctccagtt  10800
tatattgtta ttttatttta tttacttatc gagacagagt ctcgctctgt cgcccaagct  10860
ggtgtgcagt ggcacaatct cgactcatcg caaactccgc ctcccgggtt caagcgattc  10920
tcatgcctca gcctcctgag tagctgggat tacaggcatg tatcaccagg ctggacctct  10980
agtttatatt attacagcct ggtcaggag  tcactgggcg tcgccatcct gtgggtggga  11040
aggggggccca ggcagaggcc aggaggaggt gacagtcatg cgcttagaag ctcaggccac 11100
gcccacccag ccctgcctgg tgaccggttc ctgctgtgtt gggagctgca tcccagacct  11160
tatcgccggg cacagaactt ccaagccagg ggagagggag gcctggaggg gccccaatct  11220
ctgaaggtca gcagtggcgg ggaggaggct tgcggtgctg aagggactcg ggggacctgc  11280
agggaggtgt tggtggtcag ggatggtggc acctgagggg acttttggca gggccagaag  11340
tgcccagagc aagctccggt gggggccctgc actggagggc tggggtcgag tgaccctctt  11400
cctaagacca cccaggagga cactgggtgc agggtggccg gagccctcac ccccagtagg  11460
cagctgctgt ccactccgcc gacctgcctg tcacccagta ggcagctgct gtccactccc  11520
ccgacctgcc tgtcacccag taggcagctg ctgtccactc cccgacctg  cctgtcaccc  11580
aataggcagc tgctgtccag tcccccgacc tgcctgtcag ccttttccct gtcaggccct  11640
gttcctagga gcctggagac ctcaggggtg gccttgagcc cccagggttt ttttgagggg  11700
aagcgccagc tgctgtcttc acccttcccc tagtgaggcc aggctgtgca gggccacgtg  11760
gaggcagtct gtgctgcgcc catcggtcgc ctggcttcct gccgaccctc ggcccccagc  11820
cacctctggt ctcgggcaag gcccctcccc ctgcccacct cctccctggc ccccacgcca  11880
ggtgggcaga cctcctctgc ggtttttatt caggggggtcc ctcgttggct gcccactctt  11940
ggagggctgt cctgactcag gcctcccctc tactcagatc ccctgagcga gggcctgggc  12000
gtgacgccgg gagttactgg ggggccagag ggggaggctc agcctgaatc aatgagaccc  12060
aggaggaagg aggcacgtgg acctgagggc tggctggagc cgctggtgac agatggagga  12120
gtaattgctg cttccagagc acagcgagct cgagctccct ggagtgccag aagcttctgg  12180
gtggacagac aggccgcctc acattccaga ggctgacaca gtcttccagg cacccctggg  12240
gccagctgga agccatgtgc ctccactcac gtgtcccgtg ggtgtttgga ggggaggctg  12300
gccctgccat ggcccacccc agcctgcggc ctcaggagct tgcacatttg caaggggtg   12360
acatgaagac tgagccaggg ctgcggcggg catccccctc agagaacagg gaggagggg   12420
cacaggcctt ttttttttt  ttttgacag  agtctcactc tttggccagg ctggaatgca  12480
gtggcacgat ctcagctcac tgccaccttc gcctcccagg ttcaagcgat tctcctgcct  12540
cagcctcccc agtagctgag attacaggca cccaccatca cgcccggctc attttttgtat 12600
ttttagtaga gacgggggttt taccatgttg tccaggatgg tcttgatctg ttgacctcgt  12660
```

```
gatctgcttg cctcggcctc ccaaagtgct gggattacag gcgtgagcca ctgtgccctg   12720
ccaggcacgg gccttttat gagggaggaa gccgtgccct ctgccacctg cctgtgggct    12780
ggggcctgca ggctcccagg gccctcagct ccagcgtggc tgttggttat tggcacctgg   12840
gcctcatgtc cacatggaaa gtatattccg agctggtggc taagccacaa gagcctgctt   12900
acctgtccca accccggct cacttgctgc catgatacgt ctgggattct gggccctcct    12960
tctgagcttg gacacagact tgggacttca gcgctggaca caggtgctgg atctggggtc   13020
tcaatggcac cagggatggt cattctgaca gccatgccca gagtctcagg agggcctggg   13080
gccgcaggtg gacaggcatc ctgaccagag tctcaggagg gcctggggcc gcgggtggac   13140
aggcatagag tctcaggtgg gcctggggcc gcgggtggac gggcatagag tctcaggagg   13200
gcctggggcc gcgggtggat gggcatagag tctcaggagg gcctggggcc gcgggtggac   13260
gggcatagag tctcaggtgg gcctggggcc gcgggtggac gggcatagag tctcaggagg   13320
gcctggggcc gcgggtggac gggcatagag tctcaggagg gcctggggcc gcgggtggac   13380
gggcatagag tctcaggagg gcctggggcc gcgggtggac gggcatagag tctcaggagg   13440
gcctggggcc gcgggtggac gggcatagag tctcaggagg gcctggggcc gcgggtggac   13500
gggcatctgg acgtcggctc cactagtgtc acctctgcaa ccttgtccca cccagcacct   13560
ccctatggcc ctgctctgac tgtgggctga gggggacccc catggctagc ttggacctc    13620 cgctggacac tgtcataggg cacttgtcga gtggccctgc tgaggttcag gcttgggcgt   13680
gtgtggcccc tgagcccagc agctgcgtga ccgtgggga gccgagcccc cagtcaagaa    13740
agctgtgtgc tccttaccct gcctgctggg cttggggcct gcagggcaag ggaggcggtg   13800
ggatgggagc cccgcctggc ctggtttctt gttgtcgccg cactcctagc tgtatgtagt   13860
cagatgaggc tcccagtcct ggctctgctg ctgagcacca ttgggccggt ggttgggtga   13920
atctctcagc ctctctgagc ctccagcact tcgtccttaa gagtggaact ggtctggacc   13980
tcccaagggg gggtcactgg gtgcagagtt cctgcaaggc tgggcccggt gccagtagcg   14040
gtcgctctgt ggggcctttc gcacggttga tttttatctc cctgtgagat tagcgcctgc   14100
cctgctctgc ctcacggctc tggctctccg ggactgagac cacctgctaa gtgacagggg   14160
cggaaggacc ttgcaacaca gagcaagacg tgatagggtg gagctgctcc gcccaggccc   14220
cgcctgcaga tgagagggcc cagagcctct taatcccctg cgctcagggc atgtgacggc   14280
agggagtctc tccagtgccg cccaccggat tcctatagtt agagctcctc gcccaagccc   14340
ccagggcacc tcactggcct cccaggtgag gacatgaggc ccagcgactc tggtggtggc   14400
tggtgtcacc tatggcaggg ccgcgcgggg cccagtggag gacgcctggc ccggacctga   14460
ctgctccgtg ggaaccgtgg ggcgtgctca gggtgacttg gtgcggctgg gctgccagcc   14520
ggcctggctg agtcactggc agtgaaggca ccaggtggtg gacgtgctcg gcagctggcg   14580
ggagagtacc cccacccagg accgtgttca ggctgagggg gaagggagcg gcccaggcag   14640
gcaccgccca tggcggggcc cccgcactaa cggccacctc tcccgatgga ctgcagttct   14700
ggagccgccc ctgaggagaa cgccctgctc agtgtcctgg cagactctgg actcttcacc   14760
gtgccatcct cgctacagcc tggccaggca gccgctcccg tcccccacc ccacagacag     14820 gaactgcaga ctcctaaagg tcgagccagc tcccaagtcc atagccagaa agtgatgcag   14880
gcggggcccg gctgggggc aggtgtgacc gggtcatggg ggagcgggct gtgcacaggc     14940
atcaggctga gaggtctcgg ggatacgtcc tgggagccgc ctgccaggcg tcctgtgggg   15000
```

```
ctgcctgcag gcctcctctg gctttggcag gttctgtccc gacagaccga ggcttgggaa    15060
gaccggattg tgcactctct gcctggagag agggtgggga ggggctgggg cgtgtgggca    15120
gggagaacac cctgggaggc atcagtcctc ttccctgggg acgggccatg cgtcaacagt    15180
ccctcacttc ctctctcagg ggcagaggcg tgggggtccc gagcctccag gttggagtag    15240
gttaggaggg cctcagagcc ccctgctgcc ccgccatgtg gcattggaag gggtgtgacc    15300
ccctagggga tctgttaacc acactccgcc ccatgccggc ctctctgttc cctctaacct    15360
gcgcaggagc agggccagct ctgagctagc agaggtgaca tgaggctcgt cctggccccg    15420
cccaccctgg cccctccctg tttcccacca cgctccgccc accagagcta catgttgtgt    15480
ttgagcctca gccccagacc tggctcaggt cctcaggagg aagcagtgac agccaggccc    15540
ggggtcctct ccctgctctg ctccctgcgt gctgactgga ggctgcaggt ccccaggctt    15600
ggccctgacc ctcaggaatg gagccggccg atgtgaggtg ggggctccgg tcatgtgcag    15660
tggtaggaga ggaggcggga ccggtcccac agctccattg ctgccgaggc gttccgcagg    15720
tctgtcttca tattggtaag gaaaatgcga ggatggtgta gcctgggcat cccagtcccc    15780
aagtccgaaa tctaaatcca agcggaaaat tccaggcctg acttcatacg ccaggtcaca    15840
gtcagaagcc agaattattg aaagtatgct ctgggcgtgg tggcctcaca cctgtaatcc    15900
cagcactttg ggaggccatg gtgggaggat cacttgaggc caggagtttg agagcagcct    15960
gggtaacata gtgagacccc cgtcattatt tacacaaaat tatgtgactg cctttagggt    16020
atgtgtacga ggtatatatt gaaatgtgag tagaattttg tgttgagtcc catcccaag    16080 atacctcatt atgcgtgtgc aaatattcca aaatccagaa atcctaaac tggaaatact     16140 tctggcccct ttggatgagg ggccccact ctgcatagca agtgtgggcg cgggtgctgc     16200
tgtgtcctag cgtacttcag tgtgtggcct ttgcagtgaa tagggctggt gtcctcactg    16260
tacagatgag gaaactgagg cccagcttgc tttgccaagg tgcatccggc cccggccatg    16320
gctattctgg ctccagatcc catggtctgc agccacaata ctgctgtgcc ccggactggg    16380
ccctgcagct cgcggtgtcg ctggcctgcc cattgtgggc accgccccca ccccagactg    16440
gccgaggcct agaagggagc agggcctggc tgaggctgca ggggtgggga cggtcagcca    16500 gccctcact gccaggaagg gcgcatccat cctggcctct ccccagggag aagggaggag     16560
cggctgagag ggaagcgctc ttgccctgtg gacgagctcc tgccccacgg actagggagc    16620
ccccgcccac aacctgcttg tcagggccac ccgggacccc cgggagttcg gctgctcgct    16680
ctgctgttag gaattggatt agttttccat aaaaacagga tgtggtgggt gagagggcag    16740
tgtgtccgtc tttctcactc cccttttttcc aggaactgag cacgcgcata ggttttagcc    16800
agggccgtcc agtcccctcc ccaccccca cagggaacaa tccactctct gctcttaagt     16860
ggccacttaa tcagcttctc ctcctggccc ggggagcttc ttggagccgg cctgccgtgg    16920
tgggaacagc tatggggaca ccctgccata aggtccagca gctaagctgg gatgtggggg    16980
gaggggctgc gaggcccagg cagtgtgcca ggccgcacaa gaggagccca gctcttgccc    17040
caccagctgg cagccctgga ccgaggttgg gccgtgagg ttggctgggc cctgggccct     17100
gggcccccct cccaggaca cgactgtggt ggcacatggc tttgggggct cgtgggtccc     17160
actttgcaga cctctgcttt aaggggtctg gtccacgggg tccctctgg agggcctggg     17220 ggaaatctca gggacctggg gtctggaccc ggggagggga gcgggagaag catgtgcgtg    17280
agtctcgtgc tgtcagggag cccggaagt ctgcgagggc ttgggggttg tgtcagggag     17340
tgtgggtttt gcccttcagt ggtggaagct ggcttgagtc ccctcgatcc ctcaaggctg    17400
```

```
tagtcctgac tcggggctgt agggcagggc agggtgggt caccctgagg cagaaggctc    17460
agcggagatg ttctggcttg gctctgcccc tccctggctg ggtggcctca ccctgtgacc   17520
tttggggacc ctggttcctc tgagccaggg gacagcagtg actccgcctt cctaggtggc   17580
tgaggatgac atgggctccc cctgcaaatg tgggttctgg ctcagtggcc aagtgtatga   17640
tggtatgtgg ctcttggggt cctgagagag atgggagagg agcaggggtt tgtagggaag   17700
ctggcggctt ccaccccagc cagtcacctg cagtggggga gttccaaagc tgactgaagc   17760
ttcgaccttg tggctggtcc ccttccttcc tgcctcagtc attctggtct ctggggatc    17820
agggctgggg ggctctgggc tgtggggcc tgtttttgtg acttaaagct ctcccagcac    17880
agcccctga cctccttcct catgggcagg acctggccca ggggtctcag cacagccaca    17940
ggccagggat gcccttgcag atggccctgg atggaattcc agaactcaga aatgtctcct   18000
tcccgtaagg atgtcccgag actcatgaga ccgtttcctt ctgggaaggg ggaggaatgg   18060
ggagatgagt gaagagcgca ctgcagctca atccgggaag aagctaatca atcaatcagg   18120
gaagccaatc gatcggagaa gctgatggga aagctgtgct tggtagaata ggctcgtgcg   18180
ggcagagcag tcgcggcact cacaggctga ctgtgaggac cttgggtgtt actttgtgct   18240
tctctgcatt ttaaaaactt tgaaagtgg agaagaggaa agtgaatgtt ctctgagatt    18300
tcatggaaag gggaaactga gcccactct agccagtttg ggcccagggt tccaacctgg    18360
ggtggccccg gccctcgtgg cctgaggtga tcgtccctgt ggctctgaga gcagctgggg   18420
ccgggtcccc gttctgggc tggtgatcct ggggaagagc caggcagtgc cctgcccacc    18480
tagtggttat gagcccagaa tgttgatttt ttttcccttgg ttgcttcatg actttgttga   18540
atttccagag tatgtgtggg gggccccggc gtcccactcg ccccagccct gtggcagcag   18600
agctggctgt caagctcagt cagctgggcc cagggccccg gaggtaggtg ggtgtgtgcc   18660
tgagcttccc cttgggccc tgccaggtgc tgggagggac cacacaggcg gcaggaactc    18720
gggtcccca ggcctcggcc acaccagcct ggtgcttgtt atatattgat atgtctctct    18780
acctgtgaaa tgggtattta ttttaaggag ctgacgcacg cgattgtggg gctgtcacgt   18840
ctgaagttcg cagggcgcgc tggctgtcaa gagccgctgt tgcagtctcg agtccaggct   18900
gtgcgctcag gccgggcttc tctgtggcgg tcctgggaat tcctcctccg ggcccttagg   18960
cgacactccc ctgccttcag ctgattggat gaggccctca tgccgtctgc tgatttaaat   19020
caatctcatt ttaaaaacac ctgcacacca aattgcgatt ggcgtttgac taaactgggc   19080
agcgtggccc agcagcgctg acacatgaat caaccctcac accccacccg caggcgtgac   19140
cacggcaccc acgctgccga ctgagaacac agccgtgcgc tgactcgcat gtgatgtctc   19200
tggtcgcacc tcctccatcc tcagcaccct gttcagaatg gagatagcgg ccgggtgcag   19260
tgctcacacc tgtatcccca gcaccttggg aggcctgggt gggcgggtca cctgaggtca   19320
ggagttcgag accagcctgg ccaacatggt gaaaccccat ctctactgaa aatagaaaaa   19380
ttagccgggt gtggtggcag gtgtctgtag tcccagctac tcgggaggct gaggcaggag   19440
aatcgcttga acccaggagg tagaggttgt agtgcgcgag attgtgccac tgcactccag   19500
cctgggcggg cgacagagtg agactctgtc tcaaaaaaaa aaaaaaaaaa aattagagat   19560
aacgacttgg gctctctaga gaccagggag ccaggctcca ggcgctgctg tccagcccct   19620
tgccagctat acgaggtgct cacctggcca cgtgtccggg cagtgcttct ggggtggcat   19680
ccactgggag ggcaagatgg ttctggtaca ggtgcccaat tctgtcccca tttcacttac   19740
```

```
tgggaactca aggcacagag aggggagggc tgagctagga ccagacccca gtctcctgca    19800
gaagtacaca gacatgatgt acgaccatcc tggacacctg ccctgagatt cccctccctc    19860
tcctgccctg tcccagtggc ctgggggaa ggggaagcaa ggttctgaag ggagtgtgac     19920
cagacacctg cccgtgacac cccctctcca ggctgcctcc gagtggctgg tgactcccct   19980
cctgcctgcg agggaggtgg ccaggttgca ttcctctctg agtgccgggg aagtccctag   20040
agagcaggcc agcctgtgac tgggccctgg ggcagtctag acaggccaga ctggacaggc   20100 caggggggctg ggtgccgctg ggtaaatcac agggtgaggg ctctgagtca gcaccccatc  20160
ttctgtcctg ggtccagcac cgctgaggac acagtgggca gccgggtctg ccagggccag   20220
gtagctgtgt tgagaaggca gtgctcctga gaggcggcta ccgggaggtt ttcaatggcc   20280
aggcttctta ggaagccctt gttgcctctc tggggtgagt tgctgggggcc atggttggag  20340 tggtcgccag tgtctgcccc tggtgccgag ggcggagtcc tcgttttggg aggtcacggc   20400
atgatgctgg gagtcaaagg caggccgtgg caggggcatt ccttttttct ttcttttttt   20460 ttttttttg agacggagtt tcactcttgt cgcccaggct ggagtgcagt ggtgcgatcc    20520
cagctcactg ggatcccagg ctcccaggtt caagcgattc tcctgcctca gcctcccgag   20580
tagctgggat tacaggtacg tgccaccatg cccggctaat ttttgtattt ttagtagcga   20640
cggggtttcg tcatgttggc caggctggtc tcgaactcct gacctcatga tccacccgcc   20700
ttagcttccc aaagtgttgg cattacaggt gtgagccacc gcgcccggcc tggcagggga   20760
atgtcgacgc gtgatctctg cctggagagc acgttcatgt ttcccagagg acactttaga   20820
acatggcgcc tgggtttgga tgaacctcag cctaagaatc tacctgctca ggatccagcg   20880
acgctggtgg tgtggacttc agctctggag aatgggttat atggaacctg ggcgccggga   20940
gggcattgcc acgtgcttgc tgctgggggct tcaagaggac cccatctcct gtggccgaga   21000
ccccgtgtct caaggcacat ccccttttcgt accccgcccc accctccgca gcttcatgac   21060
ctctgggttt cccccaggac cttcgcatct gatgttccca gatccttcct gccactgggt   21120
cctgctctgg tgcccccgg ggaagccttc cctgaggacc cagctcagca tctggtgcta   21180
actgtggctc atcgtgcact ttggccccca ggaggctgtg ggctcctgaa accctctga    21240 accacgggct tccaaccaca cctgaccccc tgcgtgccga ccctgtgtgc aggtgtacag   21300
gtgtgcctgg ggcaggatgg ctgtgacggc ctcacagagc ccggagagct gcctcctagc   21360
ttccaaagcc ttcattcag gaatcttacc ctctcaatta gtctggaatg ctgggggcgg    21420
ggccagctcc aggtcacaga gcgacccttgt ttacccagac cttaacatcg gcccttccat   21480
gctaatcaat gtaatcattg tggtccatgc ggcctctgga atgtgctgtc cactccctgg   21540
gtcagccaga gagtgtcagg gagcacctac cggctgttac ccagtgctgc cctgacctgg   21600
ttcttcactc tgcacatttg tatcacgcca gaccctggct ggcagctcca ggtgacgagg   21660
catgtcagtg ccttcctgtt ctgttctgtt ttgttttgtt ttttaaatcg ggatgaggcc   21720
ttcctgtgtt gcccaggttg gtcttgaact ctcagggtca agcgaacctt ctgccttggc   21780
ctcataaact gctggattac aggcaggagt caccatacct ggcccactgc tactttctag   21840
atgaagagac agaatcccag agaagaagca ggggtttggc tgctggtctg gagccggttc   21900
tgctcacctc cagcttctgc cttgggccgc cctgttcaca caggagctgc tcacaggctg   21960
agacctcgag cagggccctc ctagaggaac tgggcccccg taagtgccct gagccgccag   22020
gagccggccc tgcgtctcat ccctatctcc ggaggacatt ggctgctagc tcaccagctg   22080
gcccctgggc aggcttgaat catgacctgg aacgccaggt gtctctggct ctaccccctgg  22140
```

```
acctgcaccc tgtccaagtg ccccagggcc agactgtttt ggttgcaccc tctggacggg    22200 ctaccccat gatggctgct catggaaagc tgtggttctt agggagctgc caattcctag    22260
tcctgcagcc tggagctcct gggtataagg tggggctcg ggcgtattgg ggactggggg    22320
tctcaggaaa gagcctgtgg gacctgtgaa ctcatagctg ctggccgagg gaccaccttg    22380
tggctgtcct tctcagctag gcctggtcag ggcttgtgtg cagggcggct gaagctgtgg    22440
gaggccacac tgtccacaca gtgccctgta agcccaccgt gcctcagttt ccccgtctga    22500
caagtggcac aacagaagcc acttcctggc acacagctca gggtcagggc cgacacagca    22560
cttgtgggct gccgggagac ccgagaggct gccccttcct tgccttggct gccacgggtg    22620
acctggcaaa cccctctggc cgtggcacca ctgggggtct acccttggca gtcagggttg    22680
gccgcttggc tgggagcccc ttctcctccc cagacacatc ctctccttgg ggctggaggg    22740
ggtcctgccg tccccgggat tgtcgagcag caggaatcca ggagggcagt gcctgcagct    22800
cagatggggg ccagtgggca gggccgatcc aaggtggca ggaaagtgcc catcactgac    22860
ctcaggtggg ggaggccatg gtgtgtgaag gaaggagagc tgagtgggag gtcttacttt    22920
gtcaccgccc ctctgagtgc ctgctgtgtg caaaggccag cgggggccct ttcttcagct    22980
gggctctgcc cagacccctg agctctgggt gggccgggag ggagaccttg ctgctcacag    23040
aggtggctct gcctgaccca gctcccttcc cagggcacag tgggggcata gggtcggctc    23100
cgtcagacat tccgggacct cgtccttcc tggggccaca ccctctaccc actgtccccc    23160
acctatttac ctgtatctgc gccagagatg gctgcccaga taagccctgg tttcctccct    23220
ttctggagag gctgcgggg ctggcgagga acccacctgc gcagagagtc aggggattgc    23280
tctgtgtgga acgcaggcct cacccatgcc ctggaatctg tccccttctc tgttgctgag    23340
ggatgagtcc cagatccctg accctgcagg ggagcccagc acagaaaaac tctgaggcct    23400
ccacaccctg gcagcgctgc tggtcgtctg tggggaagga caggcctgg gaggagggg    23460 gaggtgcgga gggcagtggg gagggtcagg aggaagtggg ggaagggcca cccaggcccc    23520
gatgtggggg atgtctcacg cgtggggtgg ggcattctca tctctgcttg gtctcctgcc    23580
atgctggggg tcgttcactg cggacccaa gtaccatgaa gatggggatg ggatgctgag    23640
cagcatcggg gagaacgcaa aggcacctcc cagctcaccc gccccacccc cgcaagcaca    23700
accattgcca tggtgtgggg accggaaggc ggcggctttg ggaccagact gcttctgcct    23760
cgggccgtgc cgctgggcct ttggtcagca ccatcgtgcc ctgcaagtca ctcttagcct    23820
ggtgccctcc tgggcagggc agtgccacaa gagctcaggc ccagatgtgc aggtgccact    23880
gttccaccca ccagcaggtc acctggggaa ccctcccctc ctgcagcctc tgtgtgctca    23940
tctgtgaaat gggcgtggtg gagtcacccc tggcttgtgg gagaatccca ggggctgatg    24000
cctgcaggac cctgtgggct ttgccccgct ccctgggcag agacagttcc cccagtccca    24060
cccacgtggc tgtgtgcagc aggtgcctgc tgaccctctg ttcctgcaca gtcaccttct    24120
tcacagacgg accccaccc tgccctgcaa acccctccag gggctgcggg ctgagtgtgt    24180 ccggagggt gtcctgactc tccacgccag caggtctgag agcagatggc tgtggcaggt    24240
gcggtgggtg cccagcccac agcagccacc aggcctgcag gaccctgccc cgtgtaggtc    24300
agatgagcca taaaactgag tttcctggac actgagctaa ttaaacctgg acaccgagct    24360
aattaaatgg tccagaagct cctcagtgcc ccaggctgct ggccgggctc caagtaggtg    24420
aggaacattc cgtttacctc ctgctgcgtc gaaggcgggt ggctcccctc gggcccctgc    24480
```

| | |
|---|---|
| ctgtcccggg cccctgggt gctgctgcgt caaaggcggg tgtctccgct tgggaccctg | 24540 |
| cctgtcctgg gcttcctggg tgctgctgcc tcgaagacgg gtggctcccc tcgggcccct | 24600 |
| gcctgtcctg ggctccctgg gtcctgctgc cttaaaggcg ggtcgttccc ctcggatccc | 24660 |
| tgcctgtctt gagctccctg ggtgctgcct gccctgtggc cacgtcccac tgttgccttt | 24720 |
| ggacaaagct ctcctagggc ctggggttct cccatgagat gacaggggtt ggttcaaagg | 24780 |
| tctctgaggt ttttagagct tgtgaagtg ttctagaatc cattttctct ctcattgctg | 24840 |
| gacagagagt atagactggg cttttcttg agtttctctc aactcttctt tgtccatgag | 24900 |
| gcaggaagag gggcttcctc agtcctcagc ttggggtgga ttgggatgga cagagaaccg | 24960 |
| tgcaggatcc cagcctgaga cggtccagcg ccccggggga gcggagcccg tggctcagcc | 25020 |
| gtctgtagcc acggccgggg tcactgtcac tgagggcacg gaggcccgc cggcgaggtc | 25080 |
| cgaggtgggc gtgtggggtg gtgggcgctg gaggcaggac ctctgcttgt ggagggtggg | 25140 |
| ccaggcgtgg accaggtgtc acgtccgctg gggcctttga ggggcaggtg gggattggcg | 25200 |
| cggagaagga gtgaagcagc tggggttttg ggagcctgtg cggagcaggc ccggatgcca | 25260 |
| gggtggctgg tgaaggtggg cctggccggg ctcggcctcc attgggggag cccccaggt | 25320 |
| cccctcccca cacagcttcc ccctctgtct gctgtccaag gctcctgtgc tggcactctg | 25380 |
| gggtggtagg ccatgcagcc cgtgtgaacc tccatagacc ttgctgtgaa cgctgcacgg | 25440 |
| ggcgtctggg ggcgggctgg cttcccccg tccctgggc caaccttgcc agccttcttc | 25500 |
| ttccataaaa gtgggatccg tctgagccct catggcccct ctgggtctgg gtttgctttt | 25560 |
| tgtgctctgc ctggggtcat ggcagggaag gcccagcagg ctcccttgca gagcagggca | 25620 |
| gagcagcggc cgccaggagc tgcctgtacc acgtctgctc ttcttcctct cttcctctgc | 25680 |
| ccggcccgc ccaccgtcga aagcactagc acgggagtgt ttatcggttt ctcttccaag | 25740 |
| ccaaataagg cagagagcgc tcttgcagga gttggagcag gccaggggga gggcagctgg | 25800 |
| ggcttggacc aggaccccgg ctccctgtag ctgccctggc ctggcagctg tcatccgcga | 25860 |
| actctgatcc tcgcctgccc tcacccggcc cctttcagag cttcccatgc tcagctggta | 25920 |
| gcaaaagaag tcaagaccta gcaaggtgcc tgccccggcc aggaggccca ggttctagcc | 25980 |
| ctgcagctgc cgctgtgagc tctggggact cagacgactg atgtccttcc cagcttctgt | 26040 |
| ttcctttgat gagaggaagg ttggaccaag cgacctgccc tgcttctgtc tgtttcctcc | 26100 |
| agtccttttc cttttgacc agttcacttg ttgataactc cagcaacgca tgaaaacatt | 26160 |
| ccccttgtaa aaaagggaaa tgccgtgggt agggggacc aaggacctct tctgcaggag | 26220 |
| cagacgcaac agcttggtgt ggatcttcct cagccttttt gtccatccta gacatgtgga | 26280 |
| atttcagttt tacacaaaag gaatggtagg cgtctgactc tctgtggctt gtatcacttg | 26340 |
| gcagtgccac agggattggt gcatgtttgc tctctcatgc tatgtgtcag gcactgttgt | 26400 |
| ctctgcgaca atcctgtgag gagggagtta tggttcttga tttatagacg aacaaactaa | 26460 |
| gacagaggag attgggctca tctgtggtca tctcagcagt tgtgagaggt cagggccaga | 26520 |
| gcccagtggt gtcattctgc agggcacata cagacacgac ccacagggtt ctgccgcacc | 26580 |
| ccctgccgct tggcctgctc tgcaggtggg tgccgaggct gttcctgcat ctgctgtgtc | 26640 |
| ttgtgagtcc gtgggtgcct gtggagtggg ggcagtgggt ttgcatttcc aagcactgcc | 26700 |
| tctgtcatag gctcagggag aagcagttac gcatgagctg ctatgagcca cgggtatgac | 26760 |
| tggcatcaca gcaggaggag ccctggggat ggctgagtga cgatgggtgg ggacagagct | 26820 |
| cacagaagcc agggttgccc ccaggccagg ccactgctgg ggccaaggct gggatgcagc | 26880 |

```
acgatgttgg tctgtcaggg agtggcagga agcccacagg gtcagctgac acttaaccca   26940
gagtggtggg agccttgaat gccagactga gggccacaca gttggtctcg gtgcacaagg   27000
acttgggctg agagggctgt tgctcctcaa tggccatctc cttgtgggag gagagtccgg   27060
gcagccgctt ccaggaaccc acccatgctt gaaatagtgg gaccacaggg ctgaggaggc   27120
tcctggggat tcctcccagg attcagctgc tctgtcccca accccggagg gcctattcgt   27180
ctagccctat atcctctctg ccagttaggt cagggcagag aagtagaggc acagagggtg   27240
gcggaggggt gtccagccag gcctttctgt ggcaccttct gaggctggct ggagtctgtg   27300
aaatctgtga taactggccc agacccttcc tgcctcctgg ggcatctgct ggagctgagg   27360
ctgctggggg agtctgcctg tgacttgagt ctcttgctgg gccatgctgg gctcagttcg   27420
cctgtctgtg gggtgggatg gtgccaccct taggttgttg ggaggaccca aggagagtga   27480
tgcctccagc catggcagct ggcccagctc cggcccgcag cctggctcct tcagggccag   27540 gaaccccag gtcatggact ccaaccctcg ggctctcctg cttcccaggt gacgaagctt   27600
caacccatgg gctctccttc ctgggtgtgg aagccctgga gaaggtggag atgggatctc   27660
agtccagccc attggctcca cttcctttga gaagctcttt ccccgtctt ggcccccagc   27720 ccttgttcaa gcacctgtcc ctctcctgtc tcctaggccc cgtcagtcct tttggagacc   27780
tgttcccacc cgcccctgct ctcacaggct gccagtgtcc acacactctc aggcactgtc   27840
attggagcct tttaaccaca cgggaaagca ggcaggttag gtaactaccc cccaccccc   27900 cgccagcaac gcccctgca tacccagggc ctgcaccagg tgctgctgcg ctgccagctc   27960
tctcgaggtc cctcctccta acctcaatgc atcgcgtctt ccagccccg gctccgaggg   28020 ctcagcctcc aggtggtcta acctggagtc taaacctgga ttgccatctg cctgcctcag   28080 cccttcc ctt cccagggac cgagggccag tgcggctccc cagccaccca ttttttgttt   28140
gttttgagac ggagtctcgc tctgtcgccc aggctggagt gcagtgtcct gatctcggct   28200
cactgcaagc tccatctcct gggttcacgc cattctcctg cctcagcccc caagtagct   28260 gggactacag gtgcccgcca ccacacccgg ctactttttt gtattttttag tagagacagg   28320 gtttcaccat gttggccagg atggtctcga tctcctgacc ttcgtgatctg cccgcctcgg   28380 cctcccaaag tgctgggatt acaggcatga gccactgcac ctggcttgtt tgtttttatt   28440
tttattgttt tttgagacgg aatcttgctc tattgcccag gctggagtgc agtgacataa   28500
tctcagctca ctgcaacctc cacctcccag gttcaagcga ttctcttgcc tcagcctccc   28560
aagtagctgg gactacaggc acccaccacc acacccagat acattttgta tttttagtag   28620
agatggggtt tcaccatgtt ggccaggctg gtttcgaact cctgaccatg agatggcggg   28680
cttgagccat cttcccgcct cggcctccca aagtgctggg attacaggcg tgagccacg   28740 tgcccggccc cagccaccag ttttgtacag cactcaggtg ggtgtggttc ctgaggacat   28800
gtcacacgag atccttccgg tccattagcc caccccgccc catcagtggc cagtgcggcc   28860 attgtgggt ccagagtccc gaggcagaac gactgactcc aggttgtgga ggggcctctt   28920
aggatccttc taggcaccca ggttgggcag gtgcctccat gcctaagact gagctcctgg   28980
tggacatcgg gctgggtgtg ggcgtcctgc acacctcccc tgtggcctgg tgcccgtgag   29040
gagtggacag tcaccccgag agcatagacc accctcgagg ctcccagatg gcggccgcag   29100
agccccactt ccctgcctgg tgtgtgatac cttccatggc tgaggacacc tctgactgct   29160
cactcctgtg accctggacc caagtgctgg gccacacctg gactccaggc cccagtcctt   29220
```

```
ccttcttctg ctgtcctggc tcctgggtgg ccccogccct ccccgctccg aggctctgcc    29280
ctgtgctggg aacccaggaa ttgccacccc ctggccccgg tttctcatgt caggatctgc    29340
tggccaggtt gactcctgag cgccactgtc tcctcagact tgctggtccc acccggtccc    29400
cacctgtcca ccgcccgagg ctctcctgtg aggccgctct gcagctcttg gcctggggggc    29460 ccccggcctc tcatggtgcc ttctgcactg tcccctttgg agatgggagc tttgagggta    29520
ggcgccaccg ttcggtgaaa aggcggtata agcaaagcaa ccccccagata ctgaaggagc    29580 cgggaaataa aaggaggcag acagagcaag tgtgttggta cccgcctatt tactggcagg    29640
aacttacaga cggaaacatg gcctcaggca gcctccaggc aggtagagct ctgaacccaa    29700
acgcccgatc tggggctcgt atcgtgccct gggaggaatg tgcaggtggc tgggaacgtg    29760
gcgggtgggg tggccagatt cctgctgcag caccgggttt gtttaggaag aaacgtacga    29820
ggactagaca ctctttttt tctttcctgc acgtgaatgc cagggagtag gtgctcctgc    29880
aggaagatga tgcatcaacc agccagtctg gaggcattcc gagacccggg gttaatcagc    29940
agattagcat ttaaataaag ttactctgtc cccacagcca gctaggcccg agccacatgg    30000
cgggggcggc gggggcggct gttcgccgca tcccaggctt gctccatctc ctcgtctgca    30060
atgtggaggt gacagtcgtg gtcctcggct agtgccacag gactgtacgg gacagatcac    30120
ccagccccgt gcctgcactg ggggcggcgg tgacgtgatg gccgcggcgg tgacctgatg    30180
gccgcaggtg tgtccaccct ctggttaggc ctctcctctc cctggggcgc aacaggtgtc    30240
ctcgggtggg aggttcagct gctgggcctg ggccccagc tttcagctcc tgtgcaggcg    30300
tggagcggga cggcacgccg gggcgttcgt tcacacgatg cccccagctc gtctctgcct    30360
gctctgtgat gcagcctcag ctcctgtggg tccgggtca cccacccgtg tgggccgcag    30420
tctttctgca ccacgtcctg ctctcggcca gcgctggcct gcgggcccg gcagtgtggg    30480 gtcacacaca ggccgcaccg gctgtttcac ggagcccccc tgctcaaaat cctggccttg    30540
ggtctctgtg tggctcctgg agggagcatg tatgaggtgt ccaggttgtg aaagccccat    30600
ccggcagccc tccctgtgac agtccttcag gcctcgtcag gcttggttca gcccgtgtta    30660
gaggaggcca gacagctcct cctcgatcac cacagggaac gagggttggg cagtttctcc    30720
tctcccaccc gggcgtgggt cagctgcaag ggtctcatcc caggaactgg atcctggcag    30780 ggggggctcag gcatctgaca tcccctggca ggtcttccta tgtgccagtg ggagtgggtg    30840
gtgtccagcc ctctttgtgg aatgttccgg ttgagtggtg tgtggtcctg gttaccacca    30900
tgtggcattt gtggctttcc tggccagcac ccactgaaag cagaggccag cccagccctt    30960
ggacacccag gggcccagca gctaccgtgg gggcagcctc tcccctcctg actgtgctcc    31020
tctcagctgt aggatgaagg tctgtggatg ggtgatggct gggctctctg cttcccaagg    31080
agctggatgt gggccatagt caggcgtgtg ctggtgaggc gaggggggttg ggggttggga    31140 accacagctc tctctgaccc catcccattg cagctgactc aggaaaaggc attaccccca    31200
cggggtcaca ggcccagcct gggcagctcc tgatgggaac atgggagcca cagggcaggg    31260
caggctcctg tccccgctcc ttggattgtc tcaggcccg cctccccttt ggctgaattt    31320
cttccttctc tgcctgagcc tgatctgcga agcttccgac ctgccctgag ttggagccag    31380
tcttcagggc caaaagcaat gccgtctcct ccaggcagcc tgctctgaag tctccccctc    31440
tggctttagc ccacaaagtc acagctgagg ccacatcaac acacttagac caagagcact    31500
gccggctgca tagacagcac aggtagatcc aaggagtgtt tcgaaaagcc gtggccctgc    31560
ggccgggatg cccggacctg ggtcctgacc actcttggga gctcctcccc tctcagagcc    31620
```

```
catcccatct gaaaatgggg gcattggagc attggaggag tgctcctcac tcctgccctg    31680
ctagccggct actccgagga ccccaagacc agatgatggg agaagtggtg ggctgggctg    31740
tgaccctgag ccccttctc atcccacccg tgaggctgcc cctgcttggt gtctgtggca     31800
aggctgacag aagatggcgc cagggaccag ccagggccct cctgtctcag cccgtccttg    31860
ggtgagtggg tgtgctctgg gggtggcagg tgtgctccgg gggcgggagg tgtgctgcgg    31920
ggggccgggt acgctctggg ggggcgggtg agctctgggg ggctgggtgc gctctggggg    31980
ggctggtgtg ctctggggat ggacaggtgt gctctggggg gcggggtgtg ctctggggat    32040
ggataggtgt gctctggggg ggcggttgtg ctctggggg gcaggggtgc tccgggggtg     32100
agtgtgctct gggggcggt gggtgtgctc tgggggcggt gggtgggctt tgggctaagt     32160
agccctcttc ctctctgagc cttttccttg tctgtgttgt tggtgagtgg ccgccacctg    32220
ggacaagcct tagctgtctg tccaactgtc caccatgtcc ccggaccta gaccaagccc     32280 gctgcctggt ggggcctgct tggtattgaa tgaatgaatg aatggatgaa tggatgaatg    32340
gatgaatgaa tgagtgaaca aactctgggg ggcgtgttgc tgatcacccc agggcaggcc    32400
cgtggtgggt catggtctca ggcaggggac ttgccctgcc gggtgacgtt ggcctgccgg    32460
ggaacccctg ccaaggtgcc tcccatgccc ccatcgtcct ctgcctttga gtccactctg    32520
cccctcaagg ttccctctg gctcggccag gggcagggcg gtcagggagg cctccagctc     32580
cagcccctcc ctcatctcca tcctcagccc ctgcaccgc ctcatctcca gcccagccc      32640 cttgcagcct caggctcggg cttctgagaa tcctttgcag atttcagggc tggttatttt    32700
tttattctgg caaaatatac atccataaag ctttgtttcc tgagatgatc tcaccctgtc    32760
gcccaggctg gagtgcggca gcgtgatcat ggctcactgc ggcctcagcc tcctgggctc    32820
aagtgatcct cctgctccag cctcctgagt agctgggacc acaggcatgc accatcatcc    32880
ccggctaatt tttgaatttt tttgtagaga tggggtctct gtgttgcctg gtctggtctc    32940
gaactcctgg gctcaagtga tccgcctgcc ttggcctccc aaagtgctgg gattacaggc    33000
ctcagccacc acacccggcc taaagtttgt cacgttagcc gcattgaagg gcacaggtca    33060
gcagcggtaa gcatgttcgc attgttgtgc agccatcact gacacccatc tctagaactt    33120
cttcgttttc ccaaaggaaa ctgcacgcac ggcaccacct ccctggcctc cccacagcct    33180
cagggtctgg tgaccttcat ccccaggacc tacgcttctg actccaggag ccctgcctgg    33240
tgtccacacc acactaaggt gccctgccac gggcttcgaa cccaaccctg gtgcacttgt    33300
tgagcattgg acgttcctgg caggtcagac cgtgagctcc tctgctctga cggatgcatg    33360
gacggctgcc acctggctgg acaggtgcag aggggaggtg ccaccttctc tggggacagg    33420
actggggcag aactcacccg gctgaaaagt gcagctgtgg agaacttcag aacttcagaa    33480
gcctttgctg tgaatgcatt ttcctcctgc ctcttgggcc agatcttagg gattttttt     33540 ttttttaatg aaaatgtata atcgtcaaaa aactttagat ttaaaagcat ggagccgatg    33600
gctatgcttg gtgcgttaat gggaggaaga ggggatctta acttcaggga gggctcctgg    33660
gggagctggg ggaggctgct gtgtccagca gggcgggcgg tgcccccgg agccggcac      33720 tccgcgatgt gtgcgctaag ccgaggccgc cttgagcccg tagcagcgcc gagcgcgatt    33780
ctttcgtgtc tgcttccggg agggtggaag ggtgaagctg ttgagagtgg aagggaggg    33840 gctgtgcttc ttgagttttgc cgtgtgcccc tgaccctttc aggtgcaagc gtcagctcca    33900
cggtgccaat ggggagatgg gtctggaggc cccaccaggc tgtgaaaggc ccggcctcct    33960
```

```
gtgctgtccg tggaggtcgg ggtctccctc tgccctgcgc ctcctctaac ttgccctgcg    34020
ttttccgtgc ccctggtcta gggtgaggct cgggtcttgg ggactgaggg gcaggtgggt    34080
gtcaaggtga gagctgggct gggctgggcc tccctccaga agacttcccg gggctccttt    34140
ggcaccaagg atggggcaga tggtggcacg catggcctcc cctgggcaca gagccagact    34200
atggagggat ctcgttggct acatcctggc tggggctttg gggtcatggt gggagcagca    34260 gccagggtc tcgcttggac acgggtctga gctcactgtg gcctccttcc tcagcctcct    34320
gaccggggtc ctgaggctgg agggtgggtg gagggtggag ggtgggtgga tagtgggctg    34380
gaggatgggc tgctggcgcc ccttaggcag catgaggcgc cttccagtc ccagtgtcct    34440 ccctggtagc cccggaaagg ctgagtggtc cctcaggtcc cctgcgagga gacgacatca    34500
ggccccaccc ctcatctcct gacaaacctc acattcctag gaggaagcag gcctggctag    34560
cacgtggcag gcacagcctc cctgactcca gaccttatca gatcagtgca agtgccaggg    34620 agacccggg tgggagctgt gtggttggga ctgatgcagg cactggccgg actctcagga    34680
tgagggtggg aggccaggcc ccgggacctt ctggacagg caggagggca gacacgggac    34740
atggtgtggg ggctgtggcg agtgcggcca cgcagagcat ttgggctgaa ggcgcgctgt    34800
gtcccactgc cccatacgtg tgcggggct cccagacacg tgctggggc aggaatcata    34860 gcattttttt gtttgattgt tttttgagat ggagtctcgc tctgtcgccc aggctggagt    34920
gcagtggctc aatctcggct cactgcaacc tccacctccc gggttcaagc gattctcctg    34980
cctcagcctc ctgagtagct ggaattacag gtgcccgcca ccacacccag ctaattttg    35040 tatttttttg tcaagacagg gattcaccat attggccagg ctggtcttga actcctgacc    35100
tcaggtgatc ctcctgctgc agcctcccaa actgctggga ttacaggcgt gagccaccac    35160
acccagccaa gaatagcatt ttctttcttt ctcttttga ggcggagtct tgctctgttg    35220
cccaggctgg agtgcagtgg tgccatctca gtgtaacctc cgcctcccgg tttcaagcaa    35280
ttcttctgcc tcagcctccc gagtagctgg gattacaggt gcccgccacc atgcccggct    35340
aatttttgta ttttcggtgg agacagggtt tcaccacgtt ggccaggctg gtcttgaact    35400
cctgacctca agtgatccgc ccgccttggc ctcccaaagt gctgggatga caggtgtgaa    35460
ccactgcacc cagcccaaga atagcatttt taaaggaaaa aaagcaaggt agaaagatgg    35520
gtcaaaaccc cagcgccccg ctgggaggct ggtgccgtg tcgtggcgtg tgtgagatat    35580
gtacggaagc gcgaggcggc ttccacggct ctggctcagg gcagcactca cagggcacac    35640
ggcctcggcg gtgtgacgag ctgggccgtg ggtgcgctgt cctctggggt ggggctggcc    35700
atcctctgtt ggcgacctag ttaacgccca tctccccgca gcctgcctgc tccgcttcag    35760
cggactctcg ctggtctacc tgctcttcct gctgctgctg ccctggttcc ccggccccac    35820
ccgatgcggc ctccaaggta aggccagggg accctgccca cgctctcagg gtgggagggg    35880
gtgggcattc gtttgggcc aaaattcgta cagctttcct caccttaac agcccggggt    35940 ggaagatgag gggtcccgaa ataaaatttt ttttttttt tgagacggag tctcgctcag    36000
tcgcccaggc tggagtgcag tggcgcgatc tctgctcact gcaggcttcg cctcccaggt    36060
tcacgccatt ctcctgcctc agcctcccgg gtagctggga ctacaggcgc cgccaccac    36120 gcctggctta ttttttttg tattttagt agagacgggg tttcaccgtg atagccagga    36180
tggtctcgat ctcctgacct tgtgatccgc ccgcctcggc ctcccaaagt gctgggatta    36240
cagacgtgag ccaccgcgcc cggcttttt ttttttttt ttttttttga gaccgagtct    36300
cgctctatct cccaggctgg agtgcagtgg cacaatcttg gctcactgca acctccgcat    36360
```

```
cccaggttca agtaatcctc gcatcccagc ctcccaagta gctgcaatta caggtgtgag    36420
ccaccacgcc cagccatcaa agtttcttat tttcattgta gacccaagc taagctcaga     36480 atcttttctg atccgtgttg caggggctgt gaggggcgag gagggtcatg ggggtggagt    36540
ctctgtgtcc cttgggaggc cacagggagt ggatgggccc caactgccca ctctctgcag    36600
gctccaggca cgtttcctgc ctgctgaggc tctggcagcc tgggagttcc agccgcctgg    36660
accgccctcc cgctgcccgc tgtggggttg gacctcagtt gactttgatc cacttgtgcg    36720
gggggggggg ggagctgaga ccccccttgg gaaccacctt ggggtctgag ctgggccagg    36780
actgtgttgc tctcccgtat cctccaaaca gagggcggtg aggccacgtg ccaagcctgc    36840
agcctgggtg acgagggtag cagcaaaccc tccatcctgt gacatgtcac ctacctgccc    36900
tgtggggggc atgtccattt tgtgcccacg ttttaggaga gcgcgttttg gagcaaacac    36960
tcagagacct gtccccaaag gccatgggcc aaacgtgggt ggggccgggc cctccgctgg    37020
tctttgggtt tggagggtga agagccactg aaaggaagga aggtcccccag ggagggcaag   37080 tgtaggcagc aagagacctt ccccagcaga gggcagagag gaggccaagc aggaccaggg    37140
ggcgtgactg tggagacagg ctcttgggtg ccgcccttct gggaggtgct ggacgcatca    37200
ggctggcagc gtcggggcct gtccatggct acgaggtgtc caccgggctg cgttttttcca   37260 ggggactctg ggaggatct gcttcctctt ccagctgctc caggtgccta ccttcctggg     37320 cttgggccc ctccctccat ctccagagcc ggtggggtgg ggtcaggatc acaccctgtc     37380
tctcctgctc cctctcccct gcggtaaccc tgtggcttcg tcccatctgc ctccccggct    37440
aatccaggcc gacttccctg gtttaaggtc agctgttggg cagccccat ttcctctgct     37500 gcctggactc gcctctgcat gtgagcttct gcgttcacag attctgggga ctggggtgca    37560
ggcatcattg gggtccatcg ttctgccagc tgcaggtgga aggtcgctct ccggcctcgc    37620
gacatctggc tggaagcatc ccagaggctc ctcctagctc gtggtgctgt ggggtgggca    37680
atggtctttt ttatttattt tttttgagat ggagtctcac tctgtcaccc aggctggagt    37740
gcaatggcac gatctgggct cactgcaacc tccgcctcgc gggttcaagc gattctcccg    37800
cctcggcctc ccgagtagct gggattacag gcgcccacca tcatgcctgg ctaatttttg    37860 tgttttgta gagacagggg ttttaccatg ttggccaggc tggtcttgaa ctcctgacct     37920
caggtgatct gcccacctcg gccgagacta caggcatgag ctaccgtgct ggctttttt    37980 tttttttttc gagtgggggt cttgcttggt tgcccaggct ggagagcagt ggcatgatca    38040
tggctcactg cagcctccac ctcctgggct caagcgatcc tcctgcctta gcctaccaaa    38100
gtgctgagat tacaggtgtg agtcactgtg cccagcgcag gcactgatct tggatcatgg    38160
gtagaattca ggggtgcaga gaggcatttt gggagggggcc cagtgcggcc gagtgctggg    38220
agtcgctggg gcccgaggcc caaacccctc caggatgcat ggctggggtg ggtgggcacc   38280
cccactcccg gtccctatcc tgggcctccc ctttgctctg tggagccggt tctgtctgtt    38340
cccaggcccc tggcgtttcg ccgtttgttc cgtaaatatt tcatgcccag ggcgcaattg    38400
gaaacacttt cctttaatca gcagtggggg aaggcaggcg cccagccagg ccaggggagg    38460
agctggggtg ggaagatttg gagaggaccc gggaggactt ccctgcctga gcctcgtcag    38520
aggcccttca gagacggaga tgctgcccag ttttccggga gggagagagg aaagtgtgag    38580
gcttgcccga gccgagtgcc cggggctttta tgatttgtgc agctgctggg cttggcgtgg    38640
ccctggtgga agctctgacg ccatctgagc cttggtcccc ttgtaggcgt cagcctgatc    38700
```

-continued

```
cttgggggc tggaggttga gctcagactg aacagggagg agagggggtag gggctgggc    38760
tggggcagag ggaacagacc ctggtgctcc aggcagggct gcaggcagag ccacagggggg  38820
tggctcccag agacctgctt gtcatttagg gactcagaag ccccatcctg ccttaggata   38880
aaacccacct ccaagactga ccctgctgtc tggagagaga tcacccccca cctcttacca   38940
tgccccgtgc agggaggccc tgccaccctc tccagcttca ctggtccccc ggctctgcca   39000
gccttgtgta gtctccatcc tctgtctcaa aaggcccctc tcgtggccct accccgcagc   39060
tcagccctag ctgtcgctgg gtgggcctca tggctcagcc tcaaggcacc ctgggtccct   39120
tggctggtcc catgcacacc ccatggatca ggttccaggg ggctcccatg cacacccccac 39180
ggatcagact cagggcaact ccacactccc cacagaacaa tcaggcccag cccttgtccg   39240
gcaggtgtgg ggatggtggc tatgaccac gcatcaggat gctgccgtgg tgggggcccct   39300
cagcctttgc aggccgtgcc ggggtccaag ggctccggct ctggggagg tccatgctct    39360
gtcaaccatc cggtctgcaa taccctgggg cctccccgcc ccttcctgtt tcctcctgag   39420
agccctgcaa gctggagggg gagccccggc ccctttttttt tttttttttt ttgagacgga 39480
gtcttgttct gttgcccagg ctggagtgca gtggcgcgat ctcaactcac tgcaacctcc   39540
gcctcctggg tttaagtgaa agtgattctc ctgcctcagc ctcctgagta gctgagatta   39600
caggtgccca tcaccacgcc tggctaattt ttgtattttc agtagaaaca gggtttcacc   39660
atgttggcca ggctggtctc aaactcctga cctgaggtga tccacccacc tcggcctccc   39720
aaaggtgtga accaccacgc caggccccct gcaccttctt ctgggtgggc aagagccatg   39780
ctgagcccct cccctgccat ggataggggt ggcaagaata gtccattccc catgggctcc   39840
ctccggcagg cagcggatgg gttggggccc acacagtggt tcaggaaagg ctgaagggcg   39900
gttgccggcc agagctgggc gggtccctgg cctgagcctc ctctcactcc ctttcccagg   39960
atggaaaggc cactgtgagc tgggtgtgtc ctgccaggag ggagttggag tcggggcag    40020
gagacccact gggtctcctg ggctcctgga agaggcagca gtgggtccct gcggaggtgg   40080
cctgatcccc ggctcagcct ggttttccca gctttgcatt tgggggtggg acctgcaggg   40140
ggagagtgac ggggtgggcg gggacagggg ctgcaggtgg aggcacgaga aagccacccg   40200
accccttgag gtcatgctgt ttgcgtcgga gaagagggcc ggtgtcaggg tgcccccctcg  40260
gcctctgtgt gcacctcccc gctccccgcc ccgtgcaggt cagcagagcc tcgatccctc   40320
tgcacgttcc ggccccctcc catctccagc agcgtctctt cccggggtgc ccctcggact   40380
ctcagctccc tagtctgatc cagcccaggc agggagcggg cgtgccacgt ggccaggagt   40440
ggcctccagg cccagctgcg gccccttcga ccctgcggag ggatcatggc ccagctgttc   40500
taacatggcc agaccaggac actctggccg gcccgagaac tgaaccggga aggaggcagg   40560
gaaaggggag ggaggaagac aatggggaag cagtgacatc cgagatgtag ccagagacgg   40620
acatcctgga ctgtcgtgca gggcaaggcg ggtgggcggg agccaggtgg cctgagagcc   40680
cctccctgcc caggggtctc tggtcaggca gttccttccc gggctgctgg atcgtgtgtg   40740
cagggaaccc gtcagcctgg ctgcccaagg gccagatgt cctctcagtg cccgggggtc    40800
cttgacagcc ccagcaggag ccccacgtgc cgtgggggca ggcccgcag gtccctctct    40860
gtaggactca gaataccttc tccaatgcca cgtgctctcc ctgagtgccc agtgccacag   40920
agggccccgc tggcgaggtt acttcaacgt caggctagag ggtgcagcga gcaggactca   40980
cagcccaggt tccaggcag gtgtggcagg agcccattcc ctgggtcggt gttctcatgt    41040
caccccacgg tgaccctgct gtacagaggc ggggcgcgg ggcccctggc tggtgccctc    41100
```

```
ctgctgccag acttgtgctc tgctgaagag gggctggcgc ggcaggtatg agcccggcac   41160
ggaggtcgtg agcagtgaga agcctggcac ctatgggttc ggggcaggga ggccctggaa   41220
ggtcctgtcc tccgggagcc ctgcacagca cccctggtg gtggctcctg ttcgtgtcgg    41280
ggctgcagcc tcccttcctg gacggttttc cattcctcct tcccactctc cctgctgctc   41340
acccctccca tcctccacag gtcagaggtc atagctgcag ggtcagcagg tcagggcctg   41400
gggcaaccct aggaaggtgt gagtgtgaga agctggtcca aacctgcctc ggctgcctgg   41460
tggtgcggac agggagtcct gggcatccgt gagggctgct tcacggtcag gcttagggat   41520 gtgcaggggtg acttggacgt gggtcatgag tctttgctcc agaaagaggg ggctgagtgt   41580
ccaaggccaa tcccgagtct gtcacctaac accatttgtg ctcaaaaaac tgaacagagt   41640
ggacacaggc cctgagtttg cgccccgagg ccgagagagg gcagatgtgg tggtgacatt   41700
caccaccttg gacccagacc cagatgctac ctgtccctga gctccaggaa gttgtgagaa   41760
gggcctgagc tgttctgcac tttctcgtgg ccgggcgtgg ctggtggtgc aggagttgct   41820
gccccagggt gagggcccgg aagctcctgc cagcacgtgc cggggtggaa agggaagctg   41880
tccacagccc tgtcaggact cagaaccgg tgggtcaagg actttggtcc ggaccccctgc    41940 tgaagggtga gctgtccaca tgtgcgccga gagcagaggt gaagccaggg ctcctgagtg   42000
cccccagcca cagggtgcgc ccgcccagcc cctgccctgc agccgaaggc ctccctgctg   42060
gggggctgag tccagtgggg ccacaggcag ctgggagcag acaaggctg ccaggcaacc    42120 agatggtgct gccgcttcct gccaggtgtg ggtgcacaga gagagagagg atgccggtct   42180
ggggcctgac ctggtgcaca gcaggtgcct gaaatgccag ggtggccatg gggactgggt   42240
accatgcata ggccatgcat cgggatgcaa cttctccttg cagcccctca gccccaggga   42300
ggcagctgcc tgccccactt ttctccagag ccatcatggc cctgctccca ccccagccac   42360
ggctgctcag gggcgctccg catgctctgg tctccatcca cctgcagccc ccactggggt   42420
gaggtggagc ttcttgcctc tccttgtgtc tatttcctct gcttccacaa ctgaacggtg   42480
acaggtattt gctggatgag ggagcacacc ccaggtggtt tcctctgagc ctgggaggcc   42540
ttttcctgcc tgtgggcccc aggcccatcc tgctgccacc cccaggagga tgcccggctc   42600
cttgtgacaa gagtgaccct cgggaggcgt ggggagtggg gctggccggc ctgcctgatg   42660
gggtcctgag tccatggcgg gttttcatct caggcctctg ggctctggcc gggctggggg   42720
ctattgtccg gctgagcggc ctgggctgcg gccctcccc gtccccggga ccagcctcac    42780
ccactcgctc tgccgcaggt cacacaggcc gcctcctgcg ggcattgctg ggcctcagcc   42840
tgctcttcct ggtggcccat ctcgccctcc agatctgcct gcatattgtg cccgcctgg    42900 accagctcct gggacccagc tgtgagtcgc tgaggggggcg gggtagggat agccatcctg   42960
ggggtcaggg agagggccct gcagtgaccc cgagtctcct ggggggttg actcagcctg    43020 atttatgtct ggcctggatg gtccaggtga aacgctccag ggatgaccag gccacggtgc   43080
tggctgggca gagcctgacc tgggttcccc cgtctttctc tgcaggcagc cgctgggaga   43140
ccctctcgcg acacataggg gtcacaaggt aagaccattc ctcccacccc caaccagcaa   43200
gcctcccttg gggatttcag gccccaggaa gtgggggac ccaggaggga cagagggga    43260 cctggagact catccacact cccacccaca cctggagacc catccacgct cccacccaca   43320
cctggagacc catccacact ctcacccgca cctggagacc catccacact cccacccgca   43380
cctggagacc catccacact cccacccgca cctgcagacc catccacact ctcacccgca   43440
```

```
cctggagacc catccacact cccacccgca cctggagacc catccacact cccacccgca    43500
cctggagacc catccacact cccacccgca cctggagacc catccacact cacacccaca    43560
cctgtcctct tggtctgacc gcggctgctc cctgctctcc gcaggctgga cctgaaggac    43620
atccccaacg ccatccggct ggtggcccct gacctgggca tcttggtggt ctcctctgtc    43680
tgcctcggca tctgcgggcg ccttgcaagg aacacccggc agagcccaca tccacgggag    43740
ctggtgaggg cagctgcgtc acccgtgtgt caggaggtc attcgagagc tgtggtctca     43800
gccattttga gggttatttt aatctttta aaacagatgt agacgttttg gttgtaagtt     43860
ggtgttaaag agaggaggaa gttccaaatc ccaccccggg gcccagcctg cagttccatc    43920
cgttcagacc tgtttctact cgggctctgc ctctagtcag aaacctccac gccccgacat    43980
ggcatctgtg cccttaggaa ctcttcacag gggaattatt tggggccacg cggtggtgga    44040
aacctgcagt gctgggcagt gggtctggct ggagagccac tgcagaaggg ctgagaaggg    44100
gcggccccag caggcccat gcacttacag gcaaacaggc tgtcggccca gagcccagc      44160 aggggcctgg accccaggag cgacgggcct gaagcagggc ctctgtcctc ggagtgggag    44220
gcagagtgaa ctttagctgc tacaagactt ggaggtccgg ccccgggaat ctctgagcta    44280 tggcccctc acacgacag gcatgagct ggggcctgcg acacccaacg ttgactgctc       44340
agaccctctc gtccctgcct gggcccacac ttgccatccc caggctcagc caggatttat    44400
ggccacctgg gtgtcctggc ccacgaactc cctgccccgg gcacccagcc tcctcccacc    44460
tcaccctccc agtgcccact cgtcagatag ctgatgctcg ccacgcacat gggcctcaac    44520
ttctagagga gtcccgagag ggaaaggggt tccccaagcc acacggtagg tcgagtacac    44580
ctgctcagcc tgcagaggcg gcctgccctc ctgcctgtcc tgtcgccacc ccatggggca    44640
aggctggtgc ccgcatttca gaagtgggaa cggggacctg gaggtcaagt ggcttttccg    44700
ggcatttgag ggggtccagc gctcatgagg actgtgctgc tgcctgtcct ccaagagacc    44760
cgcccctccc tcgtcagccc ctccatgctg atggggcat ggggcatgag cttcctagag     44820
tttggctgct gggaagggc tgggtggctg gactctggtc atcttcatct tggtgtgatg     44880
ggagcctgag tgtgcagctg cgccctgggc ggccagcgtg cagacagactttc agagtgagct 44940 ggggcacca ggcacctgca ggataccgtt ccgaaagatc tagaagcccc atgacccggc     45000
ctggcagggc cccgggcga ccctcactcc cacatatggg caacacacac acgtgtttgc     45060
aggcatgcga cggagtgtgc cagccagccc gaggggtgct ggccgctaga ggagggtgag    45120
gggcgtctgc agcatggctg cggcacgtgg ggcccaagtc agggccgggc ctgcccctcg    45180
gtggcctcac accccaagtc agggccgggc ctgcccctcg gtggcctcat accccaagtc    45240
agggccgggc ctgcccctcg gtggcctcac acctgttctc tcacagcagc tgcctctgtt    45300 cttttccactc ccagaaatgc tcattttca cggctctgct cagaagattt cccagggcca    45360 gggcagggc caggctgtgg gtggggtgag cgatggcgcc ctgcgttctg atccagcctc    45420 gccccccagct gctgtgtggt ctctgagagg ggtgggctca gggcctgggc ctctcctgcc   45480
ctgatctccc tgttaccctg gcctcggagc ctcccagcag ccctgcagc cctggaggcc     45540 tgtgaggaca ggactggtct ggttcatctg tcccgtcaag ccccatccc atttgacaga     45600 agggaatag gctccgagag gctgtgactt gcctcggcct gcagagcacg gagactgtca     45660
gagctggggt ggggcctatc gtccagcccc acagcctgcg gtctcagccc ggcacctgg    45720 cgcctcagcc accaggagag ccccgagtc acagatgggg acactgggcc ggtggcagcc    45780
aggccagagc cagggcatct gacgacagcc gtgttctttc caccacacct ggctttccct    45840
```

```
ggtgtttggg aaatggctgt gttctgggaa atctttagtc aggtccaggg aaaacaggcc   45900
cggcaggtct ctctccccag ccccaggccg gcctgtcact tcttctaggc agctggccac   45960
ctctgtcccc ccagaggctt ggggagggca ggagtaccac ccctatcttc caggcagagc   46020
cacccagaag gctggcaggg gtacacagga gaccctggag cctggccatg tccctcaggc   46080
ccccttggtc tctagagacc ccccggggta tagacagggc cccgctgctc cctgggtgcg   46140
tggttcgggg agatgaggtg gtataggaca gtctgtggtc tgtctgtacc tggcaaggtc   46200
atcacgtgcc tgggcttggc aggacagacc ctgggtcttc ggccagggtg ggagctgcta   46260
ccaggaaggc ctgcaggaac tgtgagcttg agtgaggaag taggaaggtg tcaggcagac   46320
ctcagggacg gctggggcct gtcccgggg aggctgtcct gtggccctca gaggagcagc   46380
tgtggatgtg gccgcctccc acgctcctgg ctgggcaggt gtgggctgga gaggtggcgt   46440
cagtgcgata cacctgacct tgcccctgtc cgtgaccttg gcaggatgat gatgagaggg   46500
atgtggatgc cagcccgacg gcagggctgc aggaagcagc aacgctggcc cctacacgga   46560
ggtcacggct ggccgctcgt ttccgagtca cggcccactg gctgctggtg gcggctgggc   46620
gggtcctggc cgtaacactg cttgcactgg caggtacgca ccgaggcagg gggcactggc   46680
agtcacactg ggagggtct tgggagttcc ctgatgactg tggagacagc gggacacatg   46740
gcactggcca ggtaccaccc tgtgtgcccc tgccccgcag gcatcgccca ccctcggcc    46800
ctctccagtg tctacctgct gctcttcctg gccctctgca cctggtgggc ctgccacttt   46860
cccatcagca ctcggggctt cagcagactc tgcgtcgcgg tggggtgctt cggcgccggc   46920
catctcatct gcctctactg ctaccagatg cccttggcac aggctctgct cccgcctgcc   46980
ggcatctggg ctaggtaacg gcttgccaca cagccccttt ttcctgccac cctggtcccg   47040
cccacctggc tcgtctagcc cctgtggccc cactgcctct ggggtggtag gctgtgacgg   47100
gtcttctctg gacagggtgc tgggtctcaa ggacttcgtg ggtcccacca actgctccag   47160
cccccacgcg ctggtcctca acaccggcct ggactggcct gtgtatgcca gccccggcgt   47220
cctcctgctg ctgtgctacg ccacggcctc tctgcgcaag ctccgcgcgt accgcccctc   47280
cggccaggtg agcacctgcc acccatggtg ggtgggctga ggccaggcca tggggctggt   47340
ctcaggacct cctgcctctg ggtggggtgt ggagctggtt tgggctcaag acgctggtct   47400
ctgcagagga aggaggcggc aaaggggtat gaggctcggg agctggagct agcagagctg   47460
gaccagtggc cccaggaacg ggagtctgac caggtgagca gccaggcagg tggagacgcc   47520
agcgtggggg gcgcccggcc agcccgtgca tggctcagcc ctgcttgccc acagcacgtg   47580
gtgcccacag cacccgacac cgaggctgat aactgcatcg tgcacgagct gaccggccag   47640
agctccgtcc tgcggcggcc tgtgagtac cgcacactgc aaggtatggc tgggtgcggg   47700
gggcggggcg gaggccggtg ctgccccctg gtggccgcct ggcgctctcg catgctcgcg   47760
ccgcacctct gcctgccgcc ccctcggggg cccaggacat ccacgggtcg gtgtcagtga   47820
cccccgagac ccccagggca gccgagtggc catgtcactg accaaccccc aagacccca    47880
gggcagctga gtggccgcgt cgttgatccc caagacccca tgggggggcct ccaggtcccc   47940
caaccctcc ccagagaatg tggctatgct gtcttgtgct gttagctctg ggagctgctc    48000
caggtggccc agtggcccca ggaggccgct cgtccagggc aggggctggc ctgggaactc   48060
tgtgttggcc acgtcgcctt gggagggcct ggggctctt tctggctact ttctttcttt    48120
accctaaccc ttgattttcc attttgcaat gtgtttctga atgaagcaaa tgaagccacg   48180
```

```
gccctggggt gggggtcctg agagtcttca ggtgcgcaga gctggaaagg gggtcagggc   48240
cacctttccc acccttttcaa ggaaagtgag gcccagagaa cggcaggtgc tggcagggcc   48300
atccctgacg ctcagggacg tgtcagccc aattgccgga gccctcgtgt tctgcccata    48360
gcccaccggg ggcctgtctc tcctgctgtg tgcttgccca gggcccagat tttagggcat   48420
agtcagggtg gggaggcctg cagatcaacc tgccgaagct gaccgctgtc cccacctgca   48480
gtgcggccca agcgggctga gcccagggag gcgtctccgc tccacagcct gggccacctc   48540
atcatggacc agagctatgt gtgcgcgctc attgccatga tggtaggcgg ctgtgggggt   48600
tggggtgggc ggcccctct gccgcgcagg tgtgggcat cgcctgggtg gggtgcgctg     48660
ggcagctgtg cagcccctc tgccgcgcag gtgtgggca tcgcctgggt ggggtgcgct     48720
gggcagctgt gcagccccct ctgccgcgca ggtgtgggc atcgcctggg tggggtgcgc    48780
tgggcagctg tgcagccctc tctgccgcgc aggtatggag catcacctac cacagctggc   48840
tgaccttcgt actgctgctc tgggcctgcc tcatctggac ggtgcgcagc cgccaccaac   48900
tggccatgct gtgctcgccc tgcatcctgc tgtatgggat gacgctgtgc tgcctacgct   48960
acgtgtgggc catggacctg cgccctgagc tgcccaccac cctgggcccc gtcagcctgc   49020
gccagctggg gctggagcac acccgctacc cctgtctgga ccttggtgcc atggtgagtg   49080
tgcaccacca catccggggg tgcctgggtg cgcagaccca tcaggggtgt cgtcctgttc   49140
aatgtccact tgcccgggg agtggcagcg ccaagaaggc agatgtgtct gtctgtcccc    49200
ttctgcccac ccagagccag cccagagtag cttctcagtg agcgtttgtt gactgaataa   49260
acagacaacc ttgtgttggc acgggcacca ccctgtgcc ctgacactgt gtgagcgtgg    49320
gctctgttgg cacgggcacc accctgtgc cccgacactg tgtgtgagca tgggctatgc    49380
ccattggcac aggcaccacc cctgcgcccc tgacagtgtg tgtgagcgtg gctctgccc    49440 attggcacca tgcacagccc tgggtctcag tgacaagctg tgcaggccat gtgttcacag   49500
ggtgcctgcg tgtccatgtg aaacgggtgc cagcatcgtg tctggacacc tgtttgcagg   49560
ccagtgggtc tcatcttgtg aaacttgtga gcctgtgtgc caacatatgc acctgtgagc   49620
ttgtgtgcat atgtgagcac gcatgtgggc aaacatgcac tccagcatgt ggacatgtgt   49680
gcaggtgcgt gcatggatct gtgcccacgt gaactagtga acccgtgtgt gactctgcgt   49740
gtgagcgcaa gtgaacccat gcactcatcc atggatgtga gagtgtgtgc tcgtgtgcct   49800
ctgagtgggt gtgagcgaga gggtgttcgg tgcctgtggg gaggctgcgg tggatgggct   49860
ggtgccagcc gcctgagagc tcttgccccc tgctatagga gggtgctggg tccccggct    49920 gtgggagggg tgctgggccc cccggctgac tgtgacaccc tgcgcttgtc acagttgctc   49980
tacaccctga ccttctggct cctgctgcgc cagtttgtga aagagaagct gctgaagtgg   50040
gcagagtctc cagctgcgct gacggaggtc accgtggcag acacaggtga gtggtgggcc   50100
agaggcgggg gttgccctcc tgcctgcccg ccctgatgcc atcgcctgcc cctggcttgg   50160
cccacagagc ccacgcggac gcagacgctg ttgcagagcc tgggggagct ggtgaagggc   50220
gtgtacgcca agtactggat ctatgtgtgt gctggcatgt tcatcgtggt cagcttcgcc   50280
ggccgcctcg tggtctacaa gattgtctac atgttcctct tcctgctctg cctcaccctc   50340
ttccaggtgg ctgggggcc gggatggggg ctggggcacg gaccctcccc gcggtcctca    50400
ccacccccac ctcacccggc aggtctacta cagcctgtgg cggaagctgc tcaaggcctt   50460
ctggtggctc gtggtggcct acaccatgct ggtcctcatc gccgtctaca ccttccagtt   50520
ccaggacttc cctgcctact ggcgcaacct cactggcttc accgacgagc agtgagtcca   50580
```

```
ggctggggcg gtggggcagg ggcgccgaaa ccccgtgcac ttccccgggg ctgcagcggc   50640
tctgccgggg gccgggccgg tgctgatgct gcccctccac aggctggggg acctgggcct   50700
ggagcagttc agcgtgtccg agctcttctc cagcatcctg gtgcccggct tcttcctcct   50760
ggcctgcatc ctgcagctgc actacttcca caggcccttc atgcagctca ccgacatgga   50820
gcacgtgtcc ctgcctggca cgcgcctccc gcgctgggct cacaggtgcg gccccgccct   50880
ccctgtccgg ccctggagag gtgtagcctc ctgggccagg gagggagcca ggtgggagtt   50940
ggacaggagc cacatcttcc accttcagat cccaaggggc atttgctcat accaagggga   51000
tggcagtagc gtggaggtca cagggacagt gggcatgagt tgcgacacag ctgtgcacct   51060
gaactggcag ctgcagcaga agcggtgccg acagggcttc ttccagcccc aggaaatgag   51120
gggcaggaac ccagttggga gatgacattt tcggaccctc tcccaggcag gatgcagtga   51180
gtgggacccc actgctgcgg gaggagcagc aggagcatca gcagcagcag caggaggagg   51240
aggaggagga ggaggactcc agggacgagg ggctgggcgt ggccactccc caccaggcca   51300
cgcaggtgcc tgaaggtggg ttgggcgggc agagcacagc tgccacccag tctgctgtgc   51360
catgtcccag ctcgggggc gttggcagag tccctctgg gctccagagc ctcttcctca   51420
caggggaccc gggaatcccc gtttgtgccc cgcactgacc ctcacaccat cacaggggca   51480
gccaagtggg gcctggtggc tgagcggctg ctggagctgg cagccggctt tcggacgtc   51540 ctctcacgcg tgcaggtgtt cctgcggcgg ctgctggagc ttcacgtttt caagctggtg   51600
gccctgtaca ccgtctgggt ggccctgaag gaggtgagtg tggcaggcaa ctcagcttcc   51660 catctgggt ggggtcgctc tggcctgccc agctggcctc cccaagccca gccccacgtg   51720
cccactgccc tccccaagcc cagccccacg tgcccactgc cctcaggtgt cggtgatgaa   51780
cctgctgctg gtggtgctgt gggccttcgc cctgccctac ccacgcttcc ggcccatggc   51840
ctcctgcctg tccaccgtgt ggacctgcgt catcatcgtg tgtaagatgc tgtaccagct   51900
caaggttgtc aaccccccagg agtattccag caactgcacc gaggtaccgg cccccgaggg   51960
ctgggacggg aggaagctcc aggcaactct gtattcgcag cccgaccctc ctggggcagc   52020
tgcctcagtg cagtggggcc agcaatggag atggaggact ctccctggg ggcgccaagg   52080 gggcttcctg gaggcagcat ccttcgacct caactgtgga ccaggggcgc actccctgca   52140
cacaagggtg tccagtaggg gcggagtccc agggtctccg gcagtgagga cgggagggcc   52200 ccaccctgg acaggagag acagtcaggc atctctgcct gggaccttct cgcacatccc   52260
tccttctccc tggacctctc ttcactcccc cagcccctgc ccgtggtctc cctgtttctc   52320
aaacacctgg tccccttccc cgtgaaggtg gctccaaggc tggcagcccc cgtgtccctg   52380
gctggggagc agtggacctg ccccagagct gtggctgtgg tgggctccgg gcagggccag   52440
ggggcactgt ggcctgggag ggggcactga tgcctggcct cttgccagcc cttccccaac   52500
agcaccaact tgctgcccac ggagatcagc cagtccctgc tgtaccgggg gcccgtggac   52560
cctgccaact ggtttggggt gcggaaaggg ttccccaacc tgggctacat ccaggtgagt   52620
tgaagggctg gtgggcggct gggcgggcga gtacccggct gcccctgac ccttgccctc   52680 cgcagaacca cctgcaagtg ctgctgctgc tggtattcga ggccatcgtg taccggcgcc   52740
aggagcacta ccgccggcag caccagctgg ccccgctgcc tgcccaggcc gtgtttgcca   52800
gcggcacccg ccagcagctg gaccaggatc tgctcggctg cctcaagtac ttcatcaact   52860
tcttcttcta caaattcggg ctggaggtga ggcaaggaca ttgcctcccc ctggggcagg   52920
```

-continued

```
gcttggcctt cgggagggag ggacggctgc accgtgcagg caccgcaagc ctggccccac    52980
ctgggtttgc ctgggccaca gagggtgggg gactcagggc caggcacggc ttccctggac    53040
tcctgtggtg tgtcggtgct gacaacaggc aggggggccaa gttagatctg ctctactgta   53100
cagcccacct cctggagcct cagtttcccc tgcacgatgg caactgccag ccactcctgc    53160
cctcttgaca gcgccgctgg ccctgtcctt gcttgatgcc cgcagcctcc aggcagggct    53220
gctgcaagcc tgaggcctgc tgggtgggac aagaaagtcc ctcccccag actcagtgca    53280
tccccacacc ccgccctctc ccctccccag atctgcttcc tgatggccgt gaacgtgatc    53340
gggcagcgca tgaactttct ggtgaccctg cacggttgct ggctggtggc catcctcacc    53400
cgcaggcacc gccaggccat tgcccgcctc tggcccaact actgcctctt cctggcgctg    53460
ttcctgctgt accagtacct gctgtgcctg gggatgcccc cggccctgtg cattggtgag    53520
gggcacgtgg cttgggtggg agtgggcttt gtggcttttgt ggatgcccgt gggggtgttt   53580
cccgcctgcc ccagactcct gtccacccctc ctagacttag ccttggcctc ctccagtccc   53640
tcctctctgc tccacatcct acccaggcgc catcacctgc atcctgtctc tcgggggcgg    53700
cctggccccc tccaggctct gctgttctct tttccttttt tgcccagtat tctatcttga    53760
aatatttcaa accttcagga aagttgtgag tcacacaagg agcactgcgt cctctccggg    53820
ccccgtgcgg gtcggccgtg atgcctcaca cccaagtgct gcctcgagca tgcgtctcct    53880
gggtgagggt gtctgagccc acagcccccac acccgtggtc ccgtctcctg gcagtgccat    53940
cgtcaaacgt gtcctctgca ttcaaacagc cccggcctca gcaccctttct ttgtggccat    54000
ttggttttca gacgggatct ggtctgatgt ttgctctagt ctcttgtctt gggtctaagc    54060
cgcccccgcc tctcctgtct cttgggaagt tccggaggga ggccggtagc gttgctgacg    54120
ccgtgagact ggatttgcgt ggctgtcctg gtgctgcagg tctgctcaag gcacacagca    54180
ccctgcggtc tgagatgggg agtcacattt gtgcacgtgg ccggctcagg ggcgtcccac    54240
ctgccccaca gtggcaccca gcctgttggc actggtgggc tgtgtggggt cagccttgtg    54300
gttttacgaa acagactttc tctctgctgt ctctgtgtgt ctgtcagctg ggattcccat    54360
caaggacagc tgccatttgt tactggctgc tttccaagaa ttctgtcatc cgcagaccct    54420
gggcctcccc tctgctgagt gggtcctggc ccctccggcc acacactgtt acatcatctc    54480
cccgtatttg gctgggcatg gtggttcacg cctgtgatgc cagcactttg ggaggctgag    54540
gcaggagcat cccttgaggc caggagtttg aaaccactct ggtcaacata gcaagaaccc    54600
ttttttttttt tttttttttt tttgagatgg agtcttgctc tgtcacccag gctggagtac    54660
actggcacaa tctcggctca ctgcagcctc cgcctccgg gttcaagcaa ttctcctgtc     54720
tcagcctccc tcgtggctag gattacaggc aagcaccacc aggcccggct aattttttgta   54780
ttttagtag agacggggtt tcaccatctt ggccaggctg gtcttgaact cctgacctca    54840
ggtgatccac ccgcctccca aattacaggc ctccctcctg ggattacagg cgtgagctgc    54900
cacgcccggc ccgtcttgt tttctgctcc caggcgctgc tgcctcatct tctgctaccc     54960
aggcccagcc ttgtgctcac agccattgct ccagggagcc caatcgagtt ctaggagcgt    55020
gaggtttaga gccggggtc tgggcgctgg gtgtgcctgt tgctacaggg ctgcctcagc     55080
ctctgggccc tccagctctt ccttgttgaa acatctgctt tcgagcatca ccgaggccag    55140
ctccccgtct cctgtccacc tcttccttgt tgaaatacct gctatcaagc gtcacctagg    55200
ccagctcccc ttcttctgcc tccttccacg cggctgcgcc atgcagtcgc catcctgtga    55260
gatcagcatg tcctgggttc cccaacatcg agggtaactt tgttttttgta tcgtgaggtt   55320
```

```
ccctctgtgg cagatggggc tgtgggttca gcatgtcctg ggttccccag catcgagggt    55380
cactttgttt ttgggtcgcg aggttccctc tgtggcagat ggggctgtgg gttcagcatg    55440
tcctgggttc cccagcatcg agggtcactt tgttttttgtg tcgcgaggtt ccctctgtgg    55500
cagatggggc tgtgggttca gcatgtcctg ggttccccag catcgagggt cactttgttt    55560
ttgggtcgcg aggttccctc tgtggcagat ggggctgtg gttcagaat gtcctgggtt    55620 ccccagcatc gagggtcact tgtttttgg gtcacgaggt tccctctgtg gcagatgggg    55680
ctgtgggttc agcatgtcct gggttcccca gcatcgaggg tcactttgtt tttgtgtcgc    55740
gaggttccct ctgtggcaga tggggctgtg agatcagcat gtcctgggtt ccccaacatc    55800
gagggtcact tgtttttgg gtcgcgaggt tccctctgtg gcagatgggg ctgtgggttc    55860
agcatgtcct gggttcccca gcatcgaggg tcactttgtt tttgggtcgc gaggttccct    55920
ctgtggcaga tggggctgtg ggttcagcat gtcctgggtt ccccagcatc gagggtcact    55980
ttgtttttgg gtcgcgaggt tccctctgtg gcagatgggg ctgtgggttc agaatgtcct    56040
gggttcccca gcatcgaggg tcactttgtt tttgggtcgc gaggttccct ctgtggcaga    56100
tggggctgtg gttcagcat gtcctgggtt ccccagcatc gagggtcact ttgtttttgg    56160
gtcacgaggt tccctctgtg gcagatgggg ctgtgggttc agcatgtcct gggttcccca    56220
acatcgaggg tcactttgtt tttgggtcgc gaggttccct ctgtggcaga tggggctgtg    56280
agttcagcat gtcctgggtt ccccagcatg gagggtcact tgtttttgt gtcgcaaggt    56340 tccctctgtg gcagatgggg ctgtgagttc agcatgtcct gggttcccca gcatggaggg    56400
tcactttgtt tttgtgtcgc gaggttccct ctgtggcaga tggggctgtg agttcagcat    56460
gtcctgggtt ccccagcatg gagggtcact tgtttttgt gtcgcgaggt tccctctgtg    56520
gcagatgggg ctgtgagttc agaatgtcct gggttcccca gcatcgaggg tcactttgtt    56580
tttgtgtcgc gaggttccct ctgtggcaga tggggctgtg agatcagcat gtcctgggtt    56640
ccccaacatc gagggtcact tgtttttgg gtcgcgaggt tccctctgtg gcagatgggg    56700
ctgtgggttc agcatgtcct gggttcccca gcatcgaggg tcactttgct tttgggtcgc    56760
gaggttccct ctgtggcaga tggggctgtg agttcagcat gtcctgggtt ccccagcatg    56820
gagggtcact tgtttttgt gtcgcgaggt tccctctgtg gcagatgggg ctgtgggttt    56880
cgcagatgcg tggagtcaca tccatgccct cagtccttag ggaccgaccc tccctgcctc    56940
acacgcctcc caggaagtgt ggccggggc cggcagtgcc acggctccct ccccagcagg    57000
ccccggccgc tcccatcccc agcacgtggt cctatcagaa cgccacgtca gcaggactcc    57060
cagcaggtgg cctttaggtc tggcttcttt cacttggcag agcacactga ggtctgtcta    57120
ggctgtcgca tggatcccgg tcccacgtgc tgagcagcgc gttcccagct gtggttgctg    57180
caggttgaac ttttcctggc tgcaggcgtc cgtgcagctt ctggccgttg ttttcagagc    57240
tgtcctatca cacgcactgt cctatcatgg aatatgacgc cgtgtgggcc acaactcagg    57300
cccagcagcc cccaccccg tgctctctgg cctcctgctc agttccttg cccccagggg    57360 cttggtgcag agttgaagga atctgtgtgt gtgaacacac aggacactag agctgtcagt    57420
tctcgagaca ccaggtgtgc gcgaggtgat cccatggac cctgagggct ggtgatagac    57480
tcgggtcaac gggtggggac cgggtgtctc aggccccagg caggcccggc cttcctgac    57540 atgacaccc ttccccaga ttatccctgg cgctggagcc gggccgtccc catgaactcc    57600
gcactcatca agtggctgta cctgcctgat ttcttccggg cccccaactc caccaacctc    57660
```

```
atcagtgagt gccccccacc accccgcct ctgcagagga ccctcagagt acattcacgc   57720
ccccaaatct gctcacaagt gtgcacacag gcgtgcacgg gcggaggtgt ggtcaggcac   57780
atggcggcct gcaggccctg acctcgcacg cacgcacgca gacctcagcc tgtgtgcacg   57840
gcagcccttg tgcagatgcc ctcacaccgg ggctccccca gggacacccg gccactcacc   57900
caggcagacg tgtgtccgct cccagcggct gcacgccgac aggcctgggg tgggaggtgg   57960
gatttatgcg ccgtgcccac ctcgtgtggg tccccgtgtg gcacagcggc ggctcctgtg   58020
tcctgcaggc gactttctcc tgctgctgtg cgcctcccag cagtggcagg tgttctcagc   58080
tgagcgcaca gaggagtggc agcgcatggc tggcgtcaac accgaccgcc tggagccgct   58140
gcggggggag cccaaccccg tgcccaactt tatccactgc aggtgggttc cacgtcaccc   58200
tccacgggga accttctggg aggggtggcc ggggcgcccg ccctgacgct ccggcctggc   58260
aggtcctacc ttgacatgct gaaggtggcc gtcttccgat acctgttctg gctggtgctg   58320
gtggtggtgt ttgtcacggg ggccaccccg atcagcatct tcgggctggg ctacctgctg   58380
gcctgcttct acctgctgct cttcggcacg gccctgctgc agaggacac acgggcccgc   58440 ctcgtgctgt gggactgcct cattctgtac aacgtcaccg tcatcatctc caagaacatg   58500
ctgtcggtga gcctccggcc ccccgcacc caccgccctg ggccccgct ggccccgctg   58560 accctgctct cccccagctc ctggcctgcg tcttcgtgga gcagatgcag accggcttct   58620
gctgggtcat ccagctcttc agccttgtat gcaccgtcaa gggctactat gaccgtgagt   58680
ggccaggacg gtggcggggg agggcgtggg gaagcccct gctcctgggc cctgggcctg   58740
acccttgccg gtgcctgcct tgcagccaag gagatgatgg acagagacca ggactgcctg   58800
ctgcctgtgg aggaggctgg catcatctgg gacagcgtct gcttcttctt cctgctgctg   58860
cagcgccgcg tcttccttag ccattactac ctgcacgtca gggccgacct ccaggccacc   58920
gccctgctag cctccaggca agcttgggcc cagacacagc ccagagctcc cgtcttgggg   58980
ctgggagggg gcaatgggag gttcctcact gtctcaggcc ccggcccgtg gagggcaggc   59040
tctgccactc tgtgacatgg gcgtgtcatc tagagggaga atgaaggccg gcagatcccc   59100
ggcaccatca cactctgccc cagtgctggg tctgtcagag accacaggct gcagtgctga   59160
cggtggctgg tgtctcaccc ccagccaact ttcccactaa gggctaagtt tctccaccag   59220
cgggagggcc actgtgtggt gtcacgactg ccccagggag gggttctggc ttggggccag   59280
ctttgccttc ttccctgcag ctgtggtggg gtgggtgcca ccagacgccc ctgcatctgt   59340
acggcagaag ggcctgtcct cgccgcagac agcacggagg gtgggggcag cagatgcctc   59400
ccccgtgggt gcctcttgtc cagcgtgggc agagaggagc aggctgagct gtcccgggct   59460
gagcggggag cggcggctgc ccatgttgct ggggtcgagt gcctggtgct cacacccccat   59520 ccccgcctcc ctacagggc ttcgccctct acaacgctgc caacctcaag agcattgact   59580
ttcaccgcag gatagaggag aagtccctgg cccagctgaa aagacagtag gtgcctctgg   59640
ggcggggact ccccggctcc tcccccaat gctcagcata ccccacctt cccaccaca   59700 ggatggagcg tatccgtgcc aagcaggaga agcacaggca gggccgggtg gaccgcagtc   59760
gcccccagga caccctgggc cccaaggacc ccggcctgga gccaggtgag tgcagctgga   59820
gtcgggcacc cagggccccg tgtccagcat gtctgtgcct gctggcgtgt gctgcgtctg   59880
tgcccatgtg acgtcccaca gggctcccag cccgcctgtc ctgtccgcat gatcaccctc   59940
tgtctggcag gccccatggc cgccctgtga ctgtccgtcc acgcacatgg gctctgagcc   60000
ccatggcccc acacggcccc cgtcactgtg ggtgtccgtg tctgtctcca cctatcctgt   60060
```

```
ctccaagacg ggagcactca cagccccgac ccctcctggt ggcttgactg ctgcctcatg   60120
ctcaccctgc ccctccacag ggcccgacag tccaggggc tcctccccgc cacggaggca    60180
gtggtggcgg ccctggctgg accacgccac aggtaccccc aattaggccg cctgtggcca   60240
ccctctcagg ccctctgtgc ccccatctgt cctctgcctg gcctgctatc ttcccctccc   60300
ttcccccgac tcccaggccc tgagcgtcag gacgtgctca ggcctcctgg gtcgggggt    60360 gcctcactgg ctgcagaccc ctgggctgac tatgtcctct cctggctatg ccccagccct   60420
tccaacagtg ggagtctcgg agcttgcccc gatgacacat ggtggtcgag cagcgatctc   60480
acctgggacc cagcagcact gcgttattct gttttgtttt cttttgaga tggagtctcg   60540 ctctgtcact gcaggctgga gtgcagtggc atgatctcag ctcactgcaa tctctacctc   60600
ccgggttcaa gtgatcctcc tgcctcagcc tcccaagtaa ctgagactac aagcatgtgc   60660
cccactccag gcctttttt tttttttttg gagacggtgt cttgccctgt cgcccaggct    60720
acagtgcaat ggcgtgattg cggctcacta caaccccac ctcccaggtt caaaggattc    60780
tcctgcctca gcctcccaag tagctgggat tacaggtgcc cgccaccacg cccagctaat   60840
tttcgtattt ttagtagaga tggggtttca ccatattggc caggctggtc tcgaacctct   60900
gacttcaggt gatccgcccg cctcagcctc ccacagtgct gggattacag gcgtcagcca   60960
ccgtgcccgg cctgttctgt ttttctaact ctcacacagc ctcctgggtt ttccccggtc   61020
ctctgcagtc ggcccactct gcaccccagc ccgcgctggc tctgctcctc agctgccctg   61080
cccacctctg tcttgtccca ccgcgctggc ctgtgtcttg tgcctgcact gctcccggct   61140
actccgcatg ggaagggtgg ctctcgggcc ttggcccatg caggcggagg gggtctggct   61200
gggagtctcc ctgcatggaa ggctggctct cagtgctgcc tgcccacagt catccactcc   61260
ggggactact tcctgtttga gtccgacagt gaggaagagg aggaggctgt tcctgaagac   61320
ccgaggccgt cggcacagag tgccttccag gtgaggtggg agagcccgt cggccccact    61380 ccaaccacag agcttgtggt cctggaccag ggcagcatag agggtgtcag atgcccccag   61440
ggcctgggag ccgagctcct ccacctccag ttagcccacc ccgccccatc caggcctccc   61500
aagtcccatg ggaaaccagg ctacaggac atgggtcatg tgtagcctgc tgccccacgg    61560
tcttggctct gaccacccag gttctggtgg ctgcccgtgg cctgacctgt gagaccggcc   61620
caacaccttt gtgctggccg cctggctgtc ctgggtccat cttgggccc ctggctcttg    61680 gtgttagacc agcccaccca actcctgaat gggtgggagt cttccccac agcccctcag    61740 ggtccccatc cggagggggc tcaggacac ggaggtccct gggagacaca gagcagggat    61800
ctggatctgg cgcccggctt gcccaacccc agcttcccgc ctgggtctga tggctcggga   61860 ggcccgggtcc taaccgggg gctggccgac agctggcgta ccaggcatgg gtgaccaacg   61920
cccaggcggt gctgaggcgg cggcagcagg agcaggagca ggcaaggcag gaacaggcag   61980
gacagctacc cacaggtgag ctgggggcg tgggactct gaggggaagc cgcgggactg     62040
ccagtcactc accagcatcc tgtgcccagg aggtggtccc agccaggagg tggagccagc   62100
agagggcccc gaggaggcag cggcaggtac gtgggcccgg ggctggggag tgggaggtct   62160
ctcttggccc cacaggctgc ccctccacgc ccccctcccg cctcccgca ggccggagcc    62220 atgtggtgca gagggtgctg agcacggcgc agttcctgtg gatgctgggg caggcgctag   62280
tggatgagct gacacgctgg ctgcaggagt tcacccggca ccacggcacc atgagcgacg   62340
tgctgcgggc agagcgctac ctcctcacac aggagctcct gcaggtgagc ctgcccgtgc   62400
```

```
accacgctcg tccctgctct gcctgactac gcccctgcct gcttaacagc ctagtcccgc   62460
gcccactgca cgaaaccccg tgtggggaca agagctggac gcagcccctga gcccctgct   62520 gtgccctgca gggcggcgaa gtgcacaggg gcgtgctgga tcagctgtac acaagccagg   62580
ccgaggccac gctgccaggc cccaccgagg cccccaatgc cccaagcacc gtgtccaggt   62640
aggtgcgggg gtgacccgag ccccagctgc tgccctggt gtgtgggcat cgcctagcca    62700
tccccgaccc tcgccattcc cttgtacccc aaaggaccgt gggcacttc caccctgacc     62760 ctccctgtag cctggggtca ggccatagag caggattctc tgtgactcgg cttccctccc   62820
cagtgggctg ggcgcggagg agccactcag cagcatgaca gacgacatgg gcagccccct   62880
gagcaccggc taccacacgc gcagtggcag tgaggaggca gtcaccgacc ccggggagcg   62940
tgaggctggt gcctctctgt accagggact gatgcggacg gccagcgagc tgctcctgga   63000
caggtggggg cgggacgcgc acaacaccag cctcaccatg gccctcgggg agcagccgaa   63060
caggggcagg agactgactg tgaccggcaa cagatcgggc cgtcatgcct tcgggcagtc   63120
ccagactccc ccaaacacgc gggtctccct gtaggcgcct gcgcatccca gagctggagg   63180
aggcagagct gtttgcggag gggcagggcc gggcgctgcg gctgctgcgg gccgtgtacc   63240
agtgtgtggc cgcccactcg gagctgctct gctacttcat catcatcctc aaccacatgg   63300
tcacggcctc cgccggctcg ctggtgctgc ccgtgctcgt cttcctgtgg gccatgctgt   63360
cgatcccgag gcccagcaag cgcttctgga tgacggccat cgtcttcacc gaggtgggcc   63420
gaggccgcgg gggagggggc gcccggccca ccgcgccgtg accctccccg cgtgctgagc   63480
cccctccccc acagatcgcg gtggtcgtca agtacctgtt ccagtttggg ttcttccct    63540 ggaacagcca cgtggtgctg cggcgctacg agaacaagcc ctacttcccg ccccgcatcc   63600
tgggcctgga gaagactgac ggctacatca agtacgacct ggtgcagctc atggccctt    63660 tcttccaccg ctcccagctg ctggtgagtg tgagccttgg ctggcaatgc ggggctgggc   63720
aggccctctg gcacctgtg ctctccacca gggaggcaag gccccctcac cacaccctcc    63780
cgcccctcag tgctatggcc tctgggacca tgaggaggac tcaccatcca aggagcatga   63840
caagagcggc gaggaggagc agggagccga ggaggggcca ggggtgcctg cggccaccac   63900
cgaagaccac attcaggtgg aagccagggt cggacccacg gacgggaccc cagaacccca   63960
agtggagctc aggccccgtg atacgaggcg catcagtcta cgttttagaa gaaggaagaa   64020
ggagggccca gcacggaaag gagcggcagc catcggtata agcgccctgc ctcacaacct   64080
cctgcctacc cagttttctg agtggggcta ctgcagggag ggtctttctc agatgagacg   64140
gccaagccca gtgcgaggcc cacctggatc ccaggaaggt gccacttctg agccacagct   64200
cccggctctg cctacagagc cgtccctgac tgctgccccc ggggatgctc ccacgtgta    64260 gggtgactgt tggcctgggc tggcccctca cagttgcccc agacagagga cacagcccca   64320
gctgtctcct tgccagtgac actgggagct ttcctgtgct ccgtctgctt gtctgtcaaa   64380
cagggagaat gccagcctct tagggtggtc aggagccatg agccaggccc agtccccagg   64440
gggcccaggc agaagtcagc ttttccctac agaagctgag gacagggagg aagaagaggg   64500 ggaggaaagag aaagaggccc ccacggggag agagaagagg ccaagccgct ctggaggaag   64560
agtaagggcg gccgggcggc ggctgcaggg cttctgcctg tccctgtgag tgatggcggc   64620
cgggggcagc tggggagtgg gggtggggag gcgggtactg ggcccaggct gagcgccccc   64680
ttccgcaggg cccagggcac atatcggccg ctacggcgct tcttccacga catcctgcac   64740
accaagtacc gcgcagccac cgacgtctat gccctcatgt tcctggctga tgttgtcgac   64800
```

```
ttcatcatca tcattttttgg cttctgggcc tttggggtga gccaggcccg ggacccaaac    64860
ccagtgtacg cagagctcag cagccaccca catcccctgg gcttggctcc ccctgacctg    64920
tgctctcctg gccacagaag cactcggcgg ccacagacat cacgtcctcc ctatcagacg    64980
accaggtacc cgaggctttc ctggtcatgc tgctgatcca gttcagtacc atggtggttg    65040
accgcgccct ctacctgcgc aagaccgtgc tgggcaagct ggccttccag gtggcgctgg    65100
tgctggccat ccacctatgg atgttcttca tcctgcccgc cgtcactgag aggtgggccc    65160
acgcgtgggg gcgctcggtc tccaggggcg gggcagtgca ggctggggc cctgcggggc    65220 tgtttctgat ggggtccttg acctggccat cccgccccag gatgttcaac cagaatgtgg    65280
tggcccagct ctggtacttc gtgaagtgca tctacttcgc cctgtccgcc taccagatcc    65340
gctgcggcta ccccaccgc atcctcggca acttcctcac caagaagtac aatcatctca    65400
acctcttcct cttccagggg tgagtgcagg tccgccgggg tggggtcac ggcccgggca    65460 tgagggagcc cacctgacgg gaaccctggc tgtgggcagg ttccggctgg tgccgttcct    65520
ggtggagctg cgggcagtga tggactgggt gtggacggac accacgctgt ccctgtccag    65580
ctggatgtgt gtggaggaca tctatgccaa catcttcatc atcaaatgca gccgagagac    65640
agagaaggtg cctgggccca gggcgggggc cgggacaagg gccagggata tgccctctcc    65700
ctaagacaga ggcactgctg ccacgagaac ccgtggtgct ggaggccctc ccagggctcg    65760
gagcccatgg ggacatgagg cgagcccacc cactagctga tcacgaggcc agtgatcttg    65820
gcagctgcga gtgagtgctg ggcgcagaag tgggcagcgg agttggtcct gttccaggca    65880
ggctggcagc agagcagggc ctggtgcagg gaggaccgga cagccactgt ttgctgcatt    65940
cttgtttaat ggccttttctc agagagaatt cgtgcgtcag accactcccc cacgtaaaaa    66000
gtacaactca ggggtttcta gtggattcac agttgagcat ctgccttctc accacttcaa    66060
aaagaaaccc cgggccgggc acagcggctc acccctatca tcccagcact gtaagagacc    66120
caggagggag gtactgctca aggccaggag ttcaagatct gcacggccac aagcgagacc    66180
ctgcctcagc aaatgtaaaa ataaaacaat tagctggcaa tggcagctca tgcctatggt    66240
cccagcactt tgggaggcca aaggaggagg atcagttgag gccaggagtt ttaagaccag    66300
cctgggcaac atagtgagtg agactctctc tacaaaaaaa taaacgttag ctgggtgtga    66360
tggtgcacac ttgtgctccc agctactctg gaggctgagg tgggaggatg gcttgaggcc    66420
aggagtacag ggctgcatta agcctgatca caccactgca ctccagcttg gcaacagag    66480 tgagaccctg tctctaaaaa agtaaaaaga agaaacccag tgcccattgg ctgtcactcg    66540
gtttcccctc ccctggcccc tagtaacccc ttgtctaggt cctggttcta tgagatttgc    66600
ctacagtgga tatttcatga aaacaggctc agacagcgtt tgtccttttg taatcagctt    66660
tccttgctca gcatggtgtc tctgaggtcc acccacgtgg cagtatggcc ttcctgttta    66720
tgggcaaatg atattctgtg gcatggatgg accacaacat gctcatcgt tgatgggctg    66780 ttgcccgtga tgctgccagg cacgccggtg tacacgtctg tgtgcccgtg ccctggtcc    66840 tgtggctgca cgccagggcc ggaagtgctg gtgtgttt ccatcatgag gagctgctgg    66900
ttttccatag cagctccacc atctaaggtt cccaccacca acacgaggtt gcggtttctc    66960
cacatcctca acaacctgtt actatgtctt ttttgttctg gccatgctgc tgaacgggtg    67020
gcttgctgtg ggctcttctc agttcccctgt gaccgacgc tgagcgtctt ttcatgtgct    67080
tggccatttg tgtatcttct ctggggaaat gtctattcaa atcctttctc catagtttag    67140
```

```
ttgggctttt gagataggat ctcaggctga agtgcagtgg catgaccttc actcactgta    67200
gcctctgcct cccaggttca agcgattctc ccacctcagc ctcccgagta gctgggacta    67260
caggtgtgca ccaccaggcc tggctagtct tttgtatttt tggccaggtt cgtctcaaac    67320
tcctgacctc aaagtgctgg gatgacaagt gtgagccgcc acaccagca gttgggttgt     67380 tttttattag agttttttct gttttctgc agatacattg gctagaaatg actgaattgg     67440
aagaattctc tgtattctct ggttgctaga accttatcaa ttaaaatttg cagaaaattt    67500
ctccaattct atggactgtc tcttaaattt tcttggtgtc tttggaagca caaagtattt    67560
attttggtaa tatctggttt actttgtttc cttcgccaaa tccaggttca tgaagatttg    67620
cccgttttct tctaaaagtt ctatagttt agctctgaag tttcgctctt tgatccactt     67680
tgaggtaaat tttggcacat ggtatgaggc aggagttgcg tttcattctc ctgcctgggg    67740
cggtgcctgc accgtgttga aaaggttgt ccgttcccac tgaacggtca cagctccctt     67800
gtctaagatc aacgacccct gaacatgagg gttccaactg gactcttagt tctactccac    67860
tggcctgtgt ctgcccacca ttactaccgc tgtgccatac tgaggtcagg ctggggcttt    67920
tctgggctgc tgggtgagct ggagaatgcg gttgtgtgac ccgcaggaag ggcagagctg    67980
agcgtatgac ctgtgtcgtt cccctccaga aatacccgca gcccaaaggg cagaagaaga    68040
agaagatcgt caagtacggc atgggtggcc tcatcatcct cttcctcatc gccatcatct    68100
ggttcccact gctcttcatg tcgctggtgc gctccgtggt tggggttgtc aaccagccca    68160
tcgatgtcac cgtcaccctg aagctgggcg gctatgaggt gagcatgtgt gggtccgcct    68220
gtccattccc atccctgggg ggttctggcc aaggtggtgc accaccccca gccgctcctc    68280
cacgctcatc ttcgtggccc cgtgtccccg tgcctgcccc agccgctgtt caccatgagc    68340
gcccagcagc cgtccatcat ccccttcacg gcccaggcct atgaggagct gtcccggcag    68400 tttgacccc agccggtaag tggcctctgc cctgtgaaag ctggtgtggg gaggcggctg    68460
cagtcactga gggtgtcact tgtacccagc tggccatgca gttcatcagc cagtacagcc    68520
ctgaggacat cgtcacggcg cagattgagg gcagctccgg ggcgctgtgg cgcatcagtc    68580
cccccagccg tgcccagatg aagcgggagc tctacaacgg cacggccgac atcaccctgc    68640
gcttcacctg gaacttccag aggttcgtcc tggacttggg gcagtgcctg ggtgggtgga    68700
cccactacag tgggtcacgc tgtgttccca ccccaggga cctggcgaag ggaggcactg    68760
tggagtatgc caacgagaag cacatgctgg ccctggcccc aacagcact gcacggcggc     68820 agctggccag cctgctcgag ggcacctcgg accagtctgt gtgagtgaag ggcccgggtg    68880
gtgggcagga gggctgtgcc aggttggctg gccaggcct gacctgccag cacctccctg     68940
cagggtcatc cctaatctct tccccaagta catccgtgcc cccaacgggc ccgaagccaa    69000
ccctgtgaag cagctgcagc ccagtgagta tgggcgtggg ggttggggga ggctagagag    69060
gggtgacctg cggcctcaac gatcttctcc ctccatccca gatgaggagg ccgactacct    69120
cggcgtgcgt atccagctgc ggaggagca gggtgcgggg gccaccggct tcctcgaatg    69180
gtgggtcatc gagctgcagg agtgccggac cgactgcaac ctgctgccca tggtcatttt    69240
cagtgacaag gtcagcccac cgagcctcgg cttcctggct ggctacgggt gagtgagtgg    69300 ctggggggc accccgcagc tcgggggct ccgggcggcc ccaggactca ccagcttccc     69360
ccgcagcatc atggggctgt acgtgtccat cgtgctggtc atcggcaagt tcgtgcgcgg    69420
attcttcagc gagatctcgc actccattat gttcgaggag ctgccgtgcg tggaccgcat    69480
cctcaagctc tgccaggaca tcttcctggt gcgggagact cgggagctgg agctggagga    69540
```

| | |
|---|---|
| ggagttgtac gccaagctca tcttcctcta ccgctcaccg agaccatga tcaagtggac | 69600 |
| tcgtgagaag gagtaggagc tgctgctggc gcccgagagg gaaggagccg gcctgctggg | 69660 |
| cagcgtggcc acaaggggcg gcactcctca ggccggggga gccactgccc cgtccaaggc | 69720 |
| cgccagctgt gatgcatcct cccggcctgc ctgagccctg atgctgctgt cagagaagga | 69780 |
| cactgcgtcc ccacggcctg cgtggcgctg ccgtccccca cgtgtactgt agagttttt | 69840 |
| ttttaattaa aaaatgtttt atttatacaa atggacaatc aga | 69883 |

<210> SEQ ID NO 2
<211> LENGTH: 8089
<212> TYPE: DNA
<213> ORGANISM: homo sapien

<400> SEQUENCE: 2

| | |
|---|---|
| gggagccgcc guccggccca gcucggcccc agugagccga gcgcugcgcu ccgccgaggg | 60 |
| gcagggcggu cgccugagcg agcgcgggcc cgggacgucg gcaccggcgg ggcggccgaa | 120 |
| ggagaaggag gaagaggaga aggcggcgcg cgggucccog cgggucagcc auggcgcgcc | 180 |
| ggccccgggg cccccgcacc gccccauagc gccgcggcgu ccgcucgguc ugggccgggc | 240 |
| ccugggcccu ccagccaugg agccgcacgu gcucggcgcg guccuguacu ggcugcugcu | 300 |
| gcccugcgcg cugcuggcug ccugccugcu ccgcuucagc ggacucucgc uggucuaccu | 360 |
| gcucuuccug cugcugcugc ccugguuccc cggccccacc cgaugcggcc uccaagguca | 420 |
| cacaggccgc cuccucgggg cauugcuggg ccucagccug cucuuccugg uggcccaucu | 480 |
| cgcccuccag aucugccugc auauugugcc ccgccuggac cagcuccugg gacccagcug | 540 |
| cagccgcugg gagacccucu cgcgacacau agggguucaca aggcuggacc ugaaggacau | 600 |
| ccccaacgcc auccggcugg uggccccuga ccugggcauc uuggugguu ccucugucug | 660 |
| ccucggcauc ugcgggcgcc uugcaaggaa caccccgcag agcccacauc cacgggagcu | 720 |
| ggaugaugau gagagggaug uggaugccag cccgacggca gggcugcagg aagcagcaac | 780 |
| gcuggccccu acacggaggu cacggcuggc cgcucguuuc cgagucacgg cccacuggcu | 840 |
| gcugguggcg gcugggcggg uccuggccgu aacacugcuu gcacuggcag gcaucgccca | 900 |
| ccccucggcc cucccagug ucuaccugcu gcucuuccug gcccucugca ccugguggc | 960 |
| cugccacuuu cccaucagca cucgggggcuu cagcagacuc ugcgucgcgg uggggugcuu | 1020 |
| cggcgccggc caucucaucu gccucuacug cuaccagaug cccuuggcac aggcucugcu | 1080 |
| cccgccugcc ggcaucuggg cuagggugcu gggucucaag gacuucgugg guccaccaa | 1140 |
| cugcuccagc ccccacgcgc uguccucaa caccggccug gacuggccug uguaugccag | 1200 |
| ccccggcguc cuccugcugc gugcuacgc cacggccucu cugcgcaagc uccgcgcgua | 1260 |
| ccgcccuccc ggccagagga aggaggcggc aaaggggnau gaggcucggg agcuggagcu | 1320 |
| agcagagcug gaccagugc cccaggaacg ggagucugac cagcacgugg ugcccacagc | 1380 |
| acccgacacc gaggcugaua acugcaucgu gcacgagcug accggccaga gcuccguccu | 1440 |
| gcggcggccu gugcggccca gcgggcuga gccaggagg cguccccgc uccacagccu | 1500 |
| gggccacccu aucaugggacc agagcuaugu gugcgcgcuc auugccauga uggauggag | 1560 |
| cauccaccuac cacagcuggc ugaccuucgu acugcugcuc ugggccugcc ucaucuggac | 1620 |
| ggugcgcagc cgccaccaac uggccaugcu gugcucgccc ugcauccgc uguaugggau | 1680 |
| gacgcugugc ugcuacgcu acgugugggc cauggaccug cgcccugagc ugcccaccac | 1740 |

```
ccugggcccc gucagccugc gccagcuggg gcuggagcac acccgcuacc ccugucugga    1800
ccuuggugcc auguugcucu acacccugac cuucugcgcuc cugcugcgcc aguuugugaa    1860
agagaagcug cugaaguggg cagagucucc agcugcgcug acggagguca ccguggcaga    1920
cacagagccc acgcggacgc agacgcuguu gcagagccug ggggagcugg ugaagggcgu    1980
guacgccaag uacuggaucu augugugugc uggcauguuc aucguggcuca gcuucgccgg    2040 ccgccucgug gucuacaaga uugucuacau guuccucuuc cugcucugcc ucacccucuu    2100
ccaggucuac uacagccugu ggcggaagcu gcucaaggcc uucuggugcg ucugguggc    2160 cuacaccaug cuggccccuca ucgccgucua caccuuccag uuccaggacu ucccugccua    2220
cuggcgcaac cucacuggcu ucaccgacga gcagcugggg gaccugggcc uggagcaguu    2280
cagcgugucc gagcucuucu ccagcauccu ggugcccggc uucuucccc uggccugcau    2340 ccugcagcug cacuacuucc acaggcccuu caugcagcuc accgacaugg agcacgucuc    2400
ccugccuggc acgcgccucc cgcgcugggc ucacaggcag gaugcaguga gugggacccc    2460
acugcugcgg gaggagcagc aggagcauca gcagcagcag caggaggagg aggaggagga    2520
ggaggacucc agggacgagg ggcugggcgu ggccacuccc caccaggcca cgcaggugcc    2580
ugaaggggca gccaaguggg gccugguggc ugagcggcug cuggagcugu cagccggcuu    2640
cucggacguc cucucacgcg ugcaggugu ccugcggcgg cugcuggagc uucacguuu    2700 caagcugguc gcccuguaca ccgucugggu ggcccgaaag gagugucgg ugaugaaccu    2760 gcugcuggug gugcugugg ccuucgcccu gcccuaccca cgcuuccggc ccauggccuc    2820
cugccugucc accgugugga ccugcgucau caucgugugu aagaugcugu accagcucaa    2880
gguugucaac ccccaggagu auuccagcaa cugcaccgag cccuucccca acagcaccaa    2940
cuugcugccc acgagaauca gccaguccccu gcuuaccgg ggggcccgugg acccugccaa    3000 cugguuuggg gugcggaaag gguucccaa ccuggggcuac auccagaacc accugcaagu    3060
gcugcugcug cugguauucg aggcaucgu guaccggcgc caggagcacu accgccggca    3120
gcaccagcug gccccgcugc cugcccaggc cguguuugcc agcggcaccc gccagcagcu    3180
ggaccaggau cugcucggcu gccucaagua cuucaucaac uucuucucu acaaauucgg    3240 gcuggagauc ugcuuccuga uggccgugaa cgugaucggg cagcgcauga acuuucgggu    3300
gaccucgcac gguugcuggc ugguggccau ccucacccgc aggcaccgcc aggccauugc    3360
ccgccucugg cccaacuacu gcccucuuccu ggcgcuguuc cugcuguacc aguaccugcu    3420
gugccugggg augccccggg cccugugcau ugauuauccc uggcgcugga gccgggcgu    3480 ccccaugaac uccgcacuca ucaaguggcu guaccugccu gauuucuucc gggccccaa    3540 cuccaccaac cucaucagcg acuuucccu gcugcugcuc gccucccagc aguggcaggu    3600
guucucagcu gagcgcacag aggaguggca gcgcauggcu ggcgucaaca ccgaccgccu    3660
ggagccgcug cgggggagc ccaaccccgu gcccaacuuu auccacugca ggucccuaccu    3720 ugacaugcug aagguggccg ucuucgaua ccguucuggg cuggugcugg ugguggugu    3780 ugucacgggg gccacccgca ucagcaucuu cgggcugggc uaccgcugg ccugcuucua    3840 ccugcugcuc uucggcacgg ccgcucgca gaggcacaga cgggcccgcc ucgucgug    3900 ggacugccuc auucuguaca acguacccgu caucaucccc aagaacaugc ugucgcuccu    3960
ggccugcguc uucggguggagc agaugcagac cggcuucuugc uggcaucc agccucucag    4020 ccuuguauugc accgucaagg gcuacaugga ccccaaggag augauggaca gagaccagga    4080
cugccugcug ccuguggagg aggcuggcau caucugggac agcgucugcu ucuucuuccu    4140
```

```
gcugcugcag cgccgcgucu uccuuagcca uuacuaccug cacgucaggg ccgaccucca    4200
ggccaccgcc cugcuagccu ccaggggcuu cgcccucuac aacgcugcca accucaagag    4260
cauugacuuu caccgcagga uagaggagaa gucccuggcc cagcugaaaa gacagaugga    4320
gcguauccgu gccaagcagg agaagcacag gcagggccgg guggaccgca gucgccccca    4380
ggacacccug gccccaagg accccggccu ggagccaggg cccgacaguc caggggcuc     4440 cuccccgcca cggaggcagu ggugggcgcc cuggcuggac cacgccacag ucauccacuc    4500
cggggacuac uuccuguuug aguccgacag ugaggaagag gaggaggcug uuccugaaga    4560
cccgaggccg ucggcacaga gugccuucca gcuggcguac caggcauggg ugaccaacgc    4620
ccaggcggug cugaggcggc ggcagcagga gcaggagcag gcaaggcagg aacaggcagg    4680
acagcuaccc acaggaggug gucccagcca ggagguggag ccagcagagg ccccgaggag    4740
ggcagcggca ggccggagcc augguggugca gagggugcug agcacggcgc aguccugug   4800 gaugcuggg caggcgcuag uggaugagcu gacacgcugg cugcaggagu ucacccggca    4860
ccacggcacc augagcgacg ugcugcgggc agagcgcuac cuccucacac aggagcuccu    4920 gcagggcgg gaagugcaca ggggcgugcu ggaucagcug uacacaagcc aggccgaggc    4980
cacgcugcca ggccccaccg aggccccaa ugcccaagc accgugucca gugggcuggg    5040
cgcggaggag ccacucagca gcaugacaga cgacaugggc agcccccuga gcaccggcua    5100
ccacacgcgc aguggcagug aggaggcagu caccgacccc ggggagcgug aggcuggugc    5160
cucucuguac cagggacuga ugcggacggc cagcgagcug cuccuggaca ggcgccugcg    5220 cauccagag cuggaggagg cagagcuguu ugcggagggg cagggccggg cgcugcggcu    5280
gcugcgggcc guguaccagu guguggccgc ccacucggag cugcucugcu acuucaucau    5340
cauccucaac cacaugguca cggccuccgc cggcucgcug gugcugcccg ugcucgucuu    5400
ccugugggcc augcugucga ucccgaggcc cagcaagcgc uucuggauga cggccaucgu    5460
cuucaccgag aucgcggugg ucgucaagua ccuguuccag uuugggguucu ucccuggaa    5520 cagccacgug gugcugcggc gcuacgagaa caagcccuac uucccgcccc gcauccuggg    5580
ccuggagaag acugacggcu acaucaagua cgaccuggug cagcucaugg cccuuuucuu    5640
ccaccgcucc cagcucugu gcuauggccu cugggaccau gaggaggacu accauccaa    5700 ggagcaugac aagagcggcg aggaggagca ggggagccgag gaggggccag gggugccugc    5760
ggccaccacc gaagaccaca uucagguagga agccaggguc ggaccacgg acggaccccc    5820 agaacccaa guggagcuca gggccccguga uacgaggcgc aucagucuac guuuuagaag    5880
aaggaagaag gagggcccag cacggaaagg agcggcagcc aucgaagcug aggacaggga    5940
ggaagaagag gggaggaag agaaagaggc cccacgggg agagaagga ggccaagccg      6000 cucuggagga agaguaaggg cggccgggcg gcggcugcag ggcuucugcc ugucccuggc    6060
ccagggcaca uaucgccgc uacgcgcuu cuuccacgac auccugcaca ccaaguaccg     6120
cgcagccacc gacgucuaug cccucauguu ccggcugau guugucgacu ucaucaucau    6180 cauuuuggc uucugggccu uugggaagca cucggcggcc acagacauca cgucuccccu    6240
aucagacgac cagguacccg aggcuuuccu ggucaugcug cugauccagu ucaguaccau    6300
ggugguugac cgcgcccucu accgcgcaa gaccgugcug ggcaagcugg ccuuccaggu    6360
ggcgcugcgu cuggccaucc accauggau guucuucauc cugcccgccg ucacugagag    6420
gauguucaac cagaaugugg uggccagcu cuggacuuc gugaagugca ucuacuucgc    6480
```

| | |
|---|---|
| ccuguccgcc uaccagaucc gcugcggcua ccccacccgc auccucggca acuuccucac | 6540 |
| caagaaguac aaucaucuca accucuuccu cuuccagggg uuccggcugg ugccguuccu | 6600 |
| gguggagcug cgggcaguga uggacugggu uggacggac accacgcugu cccuguccag | 6660 |
| cuggaugugu uggaggaca ucuaugccaa caucuucauc aucaaaugca gccgagagac | 6720 |
| agagaagaaa uacccgcagc ccaaagggca gaagaagaag aagaucguca aguacggcau | 6780 |
| gguggccuc aucauccucu uccucaucgc caucaucugg uucccacugc ucuucauguc | 6840 |
| gcuggugcgc uccgugguug ggguugucaa ccagcccauc gaugucaccg ucacccugaa | 6900 |
| gcugggcggc uaugagccgc uguucaccau gagccgccag cagccguccaa ucaucccuu | 6960 |
| cacggcccag gccaugagg agcuguccg gcaguuugac cccagccgc uggccaugca | 7020 |
| guucaucagc caguacagcc cugaggacau cgucacggcg cagauugagg gcagcuccgg | 7080 |
| ggcgcugugg cgcaucaguc cccccagccg ugcccagaug aagcgggagc ucuacaacgg | 7140 |
| cacggccgac aucacccugc gcuucaccug gaacuuccag agggaccugg cgaagggagg | 7200 |
| cacuguggag uaugccaacg agaagcacau gcuggcccug gcccccaaca gcacugcacg | 7260 |
| gcggcagcug gccagccugc ucgagggcac cucggaccag ucuguggca ucccuaaucu | 7320 |
| cuuccccaag uacauccgug ccccaacgg gcccgaagcc aacccuguga agcagcugca | 7380 |
| gcccaaugag gaggccgacu accucggcgu gcguauccag cugcggaggg agcagggugc | 7440 |
| gggggccacc ggcuuccucg aauggugggu caucgagcgc caggagugcc ggaccgacug | 7500 |
| caaccugcug cccaugguca uuucaguga caaggucagc ccaccgagcc ucggcuuccu | 7560 |
| ggcuggcuac ggcaucaugg ggcuguacgu guccaucgug cuggucaucg gcaaguucgu | 7620 |
| gcgcggauuc uucagcgaga ucucgcacuc cauuaugauc gaggagcugc cgugcgugga | 7680 |
| ccgcauccuc aagcucugcc aggacaucuu ccuggugcgg gagacucggg agcuggagcu | 7740 |
| ggaggaggag uuguacgcca agcucaucuu ccucuaccgc ucaccggaga ccaugaucaa | 7800 |
| guggacucgu gagaaggagu aggagcugcu gcuggcgccc gagagggaag gagccggccu | 7860 |
| gcugggcagc guggccacaa ggggcggac uccucaggcc gggggagcca cugccccguc | 7920 |
| caaggccgcc agcugugaug caucucccg gccugccuga gcccgaugc ugcugucaga | 7980 |
| gaaggacacu gcgucccac ggccugcgug gcgcugccgu ccccacgug uacuguagag | 8040 |
| uuuuuuuuu aauuaaaaaa uguuuuauuu aucaaauggg acaaucaga | 8089 |

<210> SEQ ID NO 3
<211> LENGTH: 8089
<212> TYPE: DNA
<213> ORGANISM: homo sapien

<400> SEQUENCE: 3

| | |
|---|---|
| gggagccgcc gtccggccca gctcggcccc agtgagccga gcgctgcgct ccgccgaggg | 60 |
| gcagggcggt cgcctgagcg agcgcggggcc cgggacgtcg gcaccggcgg ggcggccgaa | 120 |
| ggagaaggag gaagaggaga aggcggcgcg cgggtccccg cgggtcagcc atggcgcgcc | 180 |
| ggccccgggg ccccgcacc gccccatagc gccgcggcgt ccgctcggtc tgggccgggc | 240 |
| cctgggccct ccagccatgg agccgcacgt gctcggcgcg gtcctgtact ggctgctgct | 300 |
| gccctgcgcg ctgctggctg cctgcctgct ccgcttcagc ggactctcgc tggtctacct | 360 |
| gctcttcctg ctgctgctgc cctggttccc cggcccacc cgatgcgcc tccaaggtca | 420 |
| cacaggccgc ctcctgcggg cattgctggg cctcagcctg ctcttcctgg tggcccatct | 480 |
| cgccctccag atctgcctgc atattgtgcc ccgcctggac cagctcctgg gacccagctg | 540 |

```
cagccgctgg gagaccctct cgcgacacat aggggtcaca aggctggacc tgaaggacat    600
ccccaacgcc atccggctgg tggcccctga cctgggcatc ttggtggtct cctctgtctg    660
cctcggcatc tgcgggcgcc ttgcaaggaa cacccggcag agcccacatc cacgggagct    720
ggatgatgat gagagggatg tggatgccag cccgacggca gggctgcagg aagcagcaac    780
gctggcccct acacggaggt cacggctggc cgctcgtttc cgagtcacgg cccactggct    840
gctggtggcg gctgggcggg tcctggccgt aacactgctt gcactggcag gcatcgccca    900
cccctcggcc ctctccagtg tctacctgct gctcttcctg gccctctgca cctggtgggc    960
ctgccacttt cccatcagca ctcggggctt cagcagactc tgcgtcgcgg tggggtgctt   1020
cggcgccggc catctcatct gcctctactg ctaccagatg cccttggcac aggctctgct   1080
cccgcctgcc ggcatctggg ctagggtgct gggtctcaag gacttcgtgg gtcccaccaa   1140
ctgctccagc ccccacgcgc tggtcctcaa caccggcctg gactggcctg tgtatgccag   1200
ccccggcgtc ctcctgctgc tgtgctacgc cacggcctct ctgcgcaagc tccgcgcgta   1260
ccgcccctcc ggccagagga aggaggcggc aaagggtat gaggctcggg agctggagct    1320
agcagagctg gaccagtggc cccaggaacg ggagtctgac cagcacgtgg tgcccacagc   1380
acccgacacc gaggctgata actgcatcgt gcacgagctg accggccaga gctccgtcct   1440
gcggcggcct gtgcggccca gcgggctga gcccagggag gcgtctccgc tccacagcct    1500
gggccacctc atcatggacc agagctatgt gtgcgcgctc attgccatga tggtatggag   1560
catcacctac cacagctggc tgaccttcgt actgctgctc tgggcctgcc tcatctggac   1620
ggtgcgcagc cgccaccaac tggccatgct gtgctcgccc tgcatcctgc tgtatgggat   1680
gacgctgtgc tgcctacgct acgtgtgggc catggacctg cgccctgagc tgcccaccac   1740
cctgggcccc gtcagcctgc gccagctggg gctggagcac acccgctacc cctgtctgga   1800
ccttggtgcc atgttgctct acaccctgac cttctggctc ctgctgcgcc agtttgtgaa   1860
agagaagctg ctgaagtggg cagagtctcc agctgcgctg acggaggtca ccgtggcaga   1920
cacagagccc acgcggacgc agacgctgtt gcagagcctg ggggagctgg tgaagggcgt   1980
gtacgccaag tactggatct atgtgtgtgc tggcatgttc atcgtggtca gcttcgccgg   2040
ccgcctcgtg gtctacaaga ttgtctacat gttcctcttc ctgctctgcc tcaccctctt   2100
ccaggtctac tacagcctgt ggcggaagct gctcaaggcc ttctggtggc tcgtggtggc   2160
ctacaccatg ctggtcctca tcgccgtcta caccttccag ttccaggact ccctgcccta   2220
ctggcgcaac ctcactggct tcaccgacga gcagctgggg gacctgggcc tggagcagtt   2280
cagcgtgtcc gagctcttct ccagcatcct ggtgcccggc ttcttcctcc tggcctgcat   2340
cctgcagctg cactacttcc acaggccctt catgcagctc accgacatgg agcacgtgtc   2400
cctgcctggc acgcgcctcc cgcgctgggc tcacaggcag gatgcagtga gtgggacccc   2460
actgctgcgg gaggagcagc aggagcatca gcagcagcag caggaggagg aggaggagga   2520
ggaggactcc agggacgagg ggctgggcgt ggccactccc caccaggcca cgcaggtgcc   2580 tgaagggggca gccaagtggg gcctggtggc tgagcggctg ctggagctgg cagccggctt   2640 ctcgacgtc ctctcacgcg tgcaggtgtt cctgcgcgg ctgctggagc ttcacgtttt     2700
caagctggtg gccctgtaca ccgtctgggt ggccctgaag gaggtgtcgg tgatgaacct   2760
gctgctggtg gtgctgtggg ccttcgccct gccctaccca cgcttccggc ccatggcctc   2820
ctgcctgtcc accgtgtgga cctgcgtcat catcgtgtgt aagatgctgt accagctcaa   2880
```

```
ggttgtcaac ccccaggagt attccagcaa ctgcaccgag cccttcccca acagcaccaa    2940
cttgctgccc acggagatca gccagtccct gctgtaccgg gggcccgtgg accctgccaa    3000
ctggtttggg gtgcggaaag ggttccccaa cctgggctac atccagaacc acctgcaagt    3060
gctgctgctg ctggtattcg aggccatcgt gtaccggcgc caggagcact accgccggca    3120
gcaccagctg gccccgctgc ctgcccaggc cgtgtttgcc agcggcaccc gccagcagct    3180
ggaccaggat ctgctcggct gcctcaagta cttcatcaac ttcttcttct acaaattcgg    3240
gctggagatc tgcttcctga tggccgtgaa cgtgatcggg cagcgcatga actttctggt    3300
gaccctgcac ggttgctggc tggtggccat cctcacccgc aggcaccgcc aggccattgc    3360
ccgcctctgg cccaactact gcctcttcct ggcgctgttc ctgctgtacc agtacctgct    3420
gtgcctgggg atgccccgg ccctgtgcat tgattatccc tggcgctgga gccgggccgt    3480
ccccatgaac tccgcactca tcaagtggct gtacctgcct gatttcttcc gggcccccaa    3540
ctccaccaac ctcatcagcg actttctcct gctgctgtgc gcctcccagc agtggcaggt    3600
gttctcagct gagcgcacag aggagtggca gcgcatggct ggcgtcaaca ccgaccgcct    3660
ggagccgctg cggggggagc ccaaccccgt gcccaacttt atccactgca ggtcctacct    3720
tgacatgctg aaggtggccg tcttccgata cctgttctgg ctggtgctgg tggtggtgtt    3780
tgtcacgggg gccacccgca tcagcatctt cgggctgggc tacctgctgg cctgcttcta    3840
cctgctgctc ttcggcacgg ccctgctgca gaggacaca cggccccgcc tcgtgctgtg    3900
ggactgcctc attctgtaca acgtcaccgt catcatctcc aagaacatgc tgtcgctcct    3960
ggcctgcgtc ttcgtggagc agatgcagac cggcttctgc tgggtcatcc agctcttcag    4020
ccttgtatgc accgtcaagg gctactatga ccccaaggag atgatggaca gagaccagga    4080
ctgcctgctg cctgtggagg aggctggcat catctgggac agcgtctgct tcttcttcct    4140
gctgctgcag cgccgcgtct tccttagcca ttactacctg cacgtcaggg ccgacctcca    4200
ggccaccgcc ctgctagcct caggggcttc gccctctac aacgctgcca acctcaagag    4260
cattgacttt caccgcagga tagaggagaa gtccctggcc cagctgaaaa gacagatgga    4320
gcgtatccgt gccaagcagg agaagcacag gcagggccgg gtggaccgca gtcgcccca    4380
ggacaccctg ggccccaagg accccggcct ggagccaggg cccgacagtc aggggggctc    4440
ctccccgcca cggaggcagt ggtggcggcc ctggctggac cacgccacag tcatccactc    4500
cggggactac ttcctgtttg agtccgacag tgaggaagag gaggaggctg ttcctgaaga    4560
cccgaggccg tcggcacaga gtgccttcca gctggcgtac caggcatggg tgaccaacgc    4620
ccaggcggtg ctgaggcggc ggcagcagga gcaggagcag gcaaggcagg aacaggcagg    4680
acagctaccc acaggaggtg gtcccagcca ggaggtggag ccagcagagg ccccgaggag    4740
ggcagcggca ggccggagcc atgtggtgca gagggtgctg agcacggcgc agttcctgtg    4800
gatgctgggg caggcgctag tggatgagct gacacgctgg ctgcaggagt tcacccggca    4860
ccacggcacc atgagcgacg tgctgcgggc agagcgctac ctcctcacac aggagctcct    4920
gcagggcggc gaagtgcaca ggggcgtgct ggatcagctg tacacaagcc aggccgaggc    4980
cacgctgcca ggcccaccg aggccccaa tgcccaagc accgtgtcca gtgggctggg    5040
cgcggaggag ccactcagca gcatgacaga cgacatgggc agcccctga gcaccggcta    5100
ccacacgcgc agtggcagtg aggaggcagt caccgacccc gggggagcgtg aggtggtgc    5160
ctctctgtac caggggactga tgcggacggc cagcgagctg ctcctggaca ggcgcctgcg    5220
catcccagag ctggaggagg cagagctgtt tgcggagggg cagggccggg cgctgcggct    5280
```

```
gctgcgggcc gtgtaccagt gtgtggccgc ccactcggag ctgctctgct acttcatcat   5340
catcctcaac cacatggtca cggcctccgc cggctcgctg gtgctgcccg tgctcgtctt   5400
cctgtgggcc atgctgtcga tcccgaggcc cagcaagcgc ttctggatga cggccatcgt   5460
cttcaccgag atcgcggtgg tcgtcaagta cctgttccag tttgggttct tccccctggaa  5520 cagccacgtg gtgctgcggc gctacgagaa caagccctac ttcccgcccc gcatcctggg   5580
cctggagaag actgacggct acatcaagta cgacctggtg cagctcatgg ccctttttctt  5640 ccaccgctcc cagctgctgt gctatggcct ctgggaccat gaggaggact caccatccaa   5700
ggagcatgac aagagcggcg aggaggagca gggagccgag gaggggccag gggtgcctgc   5760
ggccaccacc gaagaccaca ttcaggtgga agccagggtc ggacccacgg acgggacccc   5820
agaaccccaa gtggagctca ggccccgtga tacgaggcgc atcagtctac gttttagaag   5880
aaggaagaag gagggcccag cacggaaagg agcggcagcc atcgaagctg aggacaggga   5940
ggaagaagag gggaggaag agaaagaggc ccccacgggg agagaagaa ggccaagccg    6000 ctctggagga agagtaaggg cggccgggcg gcggctgcag ggcttctgcc tgtccctggc   6060
ccagggcaca tatcggccgc tacgcgcttt cttccacgac atcctgcaca ccaagtaccg   6120
cgcagccacc gacgtctatg ccctcatgtt cctggctgat gttgtcgact tcatcatcat   6180 cattttggc ttctgggcct ttgggaagca ctcggcggcc acagacatca cgtcctccct    6240
atcagacgac caggtacccg aggctttcct ggtcatgctg ctgatccagt tcagtaccat   6300
ggtggttgac cgcgcccctct acctgcgcaa gaccgtgctg ggcaagctgg ccttccaggt  6360
ggcgctggtg ctggccatcc acctatggat gttcttcatc ctgcccgccg tcactgagag   6420
gatgttcaac cagaatgtgg tggcccagct ctggtacttc gtgaagtgca tctacttcgc   6480
cctgtccgcc taccagatcc gctgcggcta ccccacccgc atcctcggca acttcctcac   6540
caagaagtac aatcatctca acctcttcct cttccagggg ttccggctgg tgccgttcct   6600
ggtggagctg cgggcagtga tggactgggt gtggacggac accacgctgt ccctgtccag   6660
ctggatgtgt gtggaggaca tctatgccaa catcttcatc atcaaatgca gccgagagac   6720
agagaagaaa tacccgcagc ccaaagggca gaagaagaag aagatcgtca agtacggcat   6780
gggtggcctc atcatcctct tcctcatcgc catcatctgg ttcccactgc tcttcatgtc   6840
gctggtgcgc tccgtggttg gggttgtcaa ccagcccatc gatgtcaccg tcaccctgaa   6900
gctgggcggc tatgagccgc tgttcaccat gagcgcccag cagccgtcca tcatcccctt   6960 cacgcccag gcctatgagg agctgtcccg gcagtttgac cccagccgc tggccatgca    7020 gttcatcagc cagtacagcc ctgaggacat cgtcacggcg cagattgagg cagctccgg    7080 ggcgctgtgg cgcatcagtc ccccagccg tgcccagatg aagcgggagc tctacaacgg   7140
cacggccgac atcacctgc gcttcacctg gaacttccag agggacctgg cgaagggagg   7200
cactgtggag tatgccaacg agaagcacat gctggccctg ccccaaca gcactgcacg     7260 gcggcagctg ccagcctgc tcgagggcac ctcggaccag tctgtggtca tccctaatct    7320
cttccccaag tacatccgtg cccccaacgg gcccgaagcc aaccctgtga agcagctgca    7380
gcccaatgag gaggccgact acctcggcgt gcgtatccca ctgcggaggg agcagggtgc   7440
gggggccacc ggcttcctcg aatggtgggt catcgagctg caggagtgcc ggaccgactg   7500
caacctgctg cccatggtca ttttcagtga caaggtcagc ccaccgagcc tcggcttcct   7560
ggctggctac ggcatcatgg ggctgtacgt gtccatcgtg ctggtcatcg gcaagttcgt   7620
```

-continued

```
gcgcggattc ttcagcgaga tctcgcactc cattatgttc gaggagctgc cgtgcgtgga   7680
ccgcatcctc aagctctgcc aggacatctt cctggtgcgg gagactcggg agctggagct   7740
ggaggaggag ttgtacgcca agctcatctt cctctaccgc tcaccggaga ccatgatcaa   7800
gtggactcgt gagaaggagt aggagctgct gctggcgccc gagagggaag gagccggcct   7860
gctgggcagc gtggccacaa ggggcggcac tcctcaggcc gggggagcca ctgccccgtc   7920
caaggccgcc agctgtgatg catcctcccg gcctgcctga gccctgatgc tgctgtcaga   7980
gaaggacact gcgtccccac ggcctgcgtg gcgctgccgt ccccacgtg tactgtagag    8040 tttttttttt aattaaaaaa tgttttattt atacaaatgg acaatcaga               8089
```

<210> SEQ ID NO 4
<211> LENGTH: 2521
<212> TYPE: PRT
<213> ORGANISM: homo sapien

<400> SEQUENCE: 4

```
Met Glu Pro His Val Leu Gly Ala Val Leu Tyr Trp Leu Leu Leu Pro
1               5                   10                  15

Cys Ala Leu Leu Ala Ala Cys Leu Leu Arg Phe Ser Gly Leu Ser Leu
            20                  25                  30

Val Tyr Leu Leu Phe Leu Leu Leu Pro Trp Phe Pro Gly Pro Thr
        35                  40                  45

Arg Cys Gly Leu Gln Gly His Thr Gly Arg Leu Leu Arg Ala Leu Leu
    50                  55                  60

Gly Leu Ser Leu Phe Leu Val Ala His Leu Ala Leu Gln Ile Cys
65                  70                  75                  80

Leu His Ile Val Pro Arg Leu Asp Gln Leu Leu Gly Pro Ser Cys Ser
                85                  90                  95

Arg Trp Glu Thr Leu Ser Arg His Ile Gly Val Thr Arg Leu Asp Leu
            100                 105                 110

Lys Asp Ile Pro Asn Ala Ile Arg Leu Val Ala Pro Asp Leu Gly Ile
        115                 120                 125

Leu Val Val Ser Ser Val Cys Leu Gly Ile Cys Gly Arg Leu Ala Arg
    130                 135                 140

Asn Thr Arg Gln Ser Pro His Pro Arg Glu Leu Asp Asp Asp Glu Arg
145                 150                 155                 160

Asp Val Asp Ala Ser Pro Thr Ala Gly Leu Gln Glu Ala Ala Thr Leu
                165                 170                 175

Ala Pro Thr Arg Arg Ser Arg Leu Ala Ala Arg Phe Arg Val Thr Ala
            180                 185                 190

His Trp Leu Leu Val Ala Ala Gly Arg Val Leu Ala Val Thr Leu Leu
        195                 200                 205

Ala Leu Ala Gly Ile Ala His Pro Ser Ala Leu Ser Ser Val Tyr Leu
    210                 215                 220

Leu Leu Phe Leu Ala Leu Cys Thr Trp Trp Ala Cys His Phe Pro Ile
225                 230                 235                 240

Ser Thr Arg Gly Phe Ser Arg Leu Cys Val Ala Val Gly Cys Phe Gly
                245                 250                 255

Ala Gly His Leu Ile Cys Leu Tyr Cys Tyr Gln Met Pro Leu Ala Gln
            260                 265                 270

Ala Leu Leu Pro Pro Ala Gly Ile Trp Ala Arg Val Leu Gly Leu Lys
        275                 280                 285

Asp Phe Val Gly Pro Thr Asn Cys Ser Ser Pro His Ala Leu Val Leu
```

```
                    290                 295                 300
Asn Thr Gly Leu Asp Trp Pro Val Tyr Ala Ser Pro Gly Val Leu Leu
305                 310                 315                 320

Leu Leu Cys Tyr Ala Thr Ala Ser Leu Arg Lys Leu Arg Ala Tyr Arg
                    325                 330                 335

Pro Ser Gly Gln Arg Lys Glu Ala Ala Lys Gly Tyr Glu Ala Arg Glu
                340                 345                 350

Leu Glu Leu Ala Glu Leu Asp Gln Trp Pro Gln Glu Arg Glu Ser Asp
            355                 360                 365

Gln His Val Val Pro Thr Ala Pro Asp Thr Glu Ala Asp Asn Cys Ile
        370                 375                 380

Val His Glu Leu Thr Gly Gln Ser Ser Val Leu Arg Arg Pro Val Arg
385                 390                 395                 400

Pro Lys Arg Ala Glu Pro Arg Glu Ala Ser Pro Leu His Ser Leu Gly
                    405                 410                 415

His Leu Ile Met Asp Gln Ser Tyr Val Cys Ala Leu Ile Ala Met Met
                420                 425                 430

Val Trp Ser Ile Thr Tyr His Ser Trp Leu Thr Phe Val Leu Leu Leu
            435                 440                 445

Trp Ala Cys Leu Ile Trp Thr Val Arg Ser Arg His Gln Leu Ala Met
        450                 455                 460

Leu Cys Ser Pro Cys Ile Leu Leu Tyr Gly Met Thr Leu Cys Cys Leu
465                 470                 475                 480

Arg Tyr Val Trp Ala Met Asp Leu Arg Pro Glu Leu Pro Thr Thr Leu
                    485                 490                 495

Gly Pro Val Ser Leu Arg Gln Leu Gly Leu Glu His Thr Arg Tyr Pro
                500                 505                 510

Cys Leu Asp Leu Gly Ala Met Leu Leu Tyr Thr Leu Thr Phe Trp Leu
            515                 520                 525

Leu Leu Arg Gln Phe Val Lys Glu Lys Leu Leu Lys Trp Ala Glu Ser
        530                 535                 540

Pro Ala Ala Leu Thr Glu Val Thr Val Ala Asp Thr Glu Pro Thr Arg
545                 550                 555                 560

Thr Gln Thr Leu Leu Gln Ser Leu Gly Glu Leu Val Lys Gly Val Tyr
                    565                 570                 575

Ala Lys Tyr Trp Ile Tyr Val Cys Ala Gly Met Phe Ile Val Val Ser
                580                 585                 590

Phe Ala Gly Arg Leu Val Val Tyr Lys Ile Val Tyr Met Phe Leu Phe
            595                 600                 605

Leu Leu Cys Leu Thr Leu Phe Gln Val Tyr Tyr Ser Leu Trp Arg Lys
        610                 615                 620

Leu Leu Lys Ala Phe Trp Trp Leu Val Val Ala Tyr Thr Met Leu Val
625                 630                 635                 640

Leu Ile Ala Val Tyr Thr Phe Gln Phe Gln Asp Phe Pro Ala Tyr Trp
                    645                 650                 655

Arg Asn Leu Thr Gly Phe Thr Asp Glu Gln Leu Gly Asp Leu Gly Leu
                660                 665                 670

Glu Gln Phe Ser Val Ser Glu Leu Phe Ser Ser Ile Leu Val Pro Gly
            675                 680                 685

Phe Phe Leu Leu Ala Cys Ile Leu Gln Leu His Tyr Phe His Arg Pro
        690                 695                 700

Phe Met Gln Leu Thr Asp Met Glu His Val Ser Leu Pro Gly Thr Arg
705                 710                 715                 720
```

-continued

```
Leu Pro Arg Trp Ala His Arg Gln Asp Ala Val Ser Gly Thr Pro Leu
            725                 730                 735

Leu Arg Glu Glu Gln Glu His Gln Gln Gln Gln Glu Glu Glu
        740                 745                 750

Glu Glu Glu Asp Ser Arg Asp Glu Gly Leu Gly Val Ala Thr Pro
            755                 760                 765

His Gln Ala Thr Gln Val Pro Glu Gly Ala Ala Lys Trp Gly Leu Val
    770                 775                 780

Ala Glu Arg Leu Leu Glu Leu Ala Ala Gly Phe Ser Asp Val Leu Ser
785                 790                 795                 800

Arg Val Gln Val Phe Leu Arg Arg Leu Leu Glu Leu His Val Phe Lys
                805                 810                 815

Leu Val Ala Leu Tyr Thr Val Trp Val Ala Leu Lys Glu Val Ser Val
            820                 825                 830

Met Asn Leu Leu Leu Val Val Leu Trp Ala Phe Ala Leu Pro Tyr Pro
            835                 840                 845

Arg Phe Arg Pro Met Ala Ser Cys Leu Ser Thr Val Trp Thr Cys Val
    850                 855                 860

Ile Ile Val Cys Lys Met Leu Tyr Gln Leu Lys Val Val Asn Pro Gln
865                 870                 875                 880

Glu Tyr Ser Ser Asn Cys Thr Glu Pro Phe Pro Asn Ser Thr Asn Leu
                885                 890                 895

Leu Pro Thr Glu Ile Ser Gln Ser Leu Leu Tyr Arg Gly Pro Val Asp
            900                 905                 910

Pro Ala Asn Trp Phe Gly Val Arg Lys Gly Phe Pro Asn Leu Gly Tyr
            915                 920                 925

Ile Gln Asn His Leu Gln Val Leu Leu Leu Val Phe Glu Ala Ile
            930                 935                 940

Val Tyr Arg Arg Gln Glu His Tyr Arg Arg Gln His Gln Leu Ala Pro
945                 950                 955                 960

Leu Pro Ala Gln Ala Val Phe Ala Ser Gly Thr Arg Gln Gln Leu Asp
            965                 970                 975

Gln Asp Leu Leu Gly Cys Leu Lys Tyr Phe Ile Asn Phe Phe Phe Tyr
            980                 985                 990

Lys Phe Gly Leu Glu Ile Cys Phe Leu Met Ala Val Asn Val Ile Gly
            995                 1000                1005

Gln Arg Met Asn Phe Leu Val Thr Leu His Gly Cys Trp Leu Val
    1010                1015                1020

Ala Ile Leu Thr Arg Arg His Arg Gln Ala Ile Ala Arg Leu Trp
    1025                1030                1035

Pro Asn Tyr Cys Leu Phe Leu Ala Leu Phe Leu Leu Tyr Gln Tyr
    1040                1045                1050

Leu Leu Cys Leu Gly Met Pro Pro Ala Leu Cys Ile Asp Tyr Pro
    1055                1060                1065

Trp Arg Trp Ser Arg Ala Val Pro Met Asn Ser Ala Leu Ile Lys
    1070                1075                1080

Trp Leu Tyr Leu Pro Asp Phe Phe Arg Ala Pro Asn Ser Thr Asn
    1085                1090                1095

Leu Ile Ser Asp Phe Leu Leu Leu Cys Ala Ser Gln Gln Trp
    1100                1105                1110

Gln Val Phe Ser Ala Glu Arg Thr Glu Glu Trp Gln Arg Met Ala
    1115                1120                1125
```

```
Gly Val Asn Thr Asp Arg Leu Glu Pro Leu Arg Gly Glu Pro Asn
1130                1135                1140

Pro Val Pro Asn Phe Ile His Cys Arg Ser Tyr Leu Asp Met Leu
1145                1150                1155

Lys Val Ala Val Phe Arg Tyr Leu Phe Trp Leu Val Leu Val Val
1160                1165                1170

Val Phe Val Thr Gly Ala Thr Arg Ile Ser Ile Phe Gly Leu Gly
1175                1180                1185

Tyr Leu Leu Ala Cys Phe Tyr Leu Leu Leu Phe Gly Thr Ala Leu
1190                1195                1200

Leu Gln Arg Asp Thr Arg Ala Arg Leu Val Leu Trp Asp Cys Leu
1205                1210                1215

Ile Leu Tyr Asn Val Thr Val Ile Ile Ser Lys Asn Met Leu Ser
1220                1225                1230

Leu Leu Ala Cys Val Phe Val Glu Gln Met Gln Thr Gly Phe Cys
1235                1240                1245

Trp Val Ile Gln Leu Phe Ser Leu Val Cys Thr Val Lys Gly Tyr
1250                1255                1260

Tyr Asp Pro Lys Glu Met Met Asp Arg Asp Gln Asp Cys Leu Leu
1265                1270                1275

Pro Val Glu Glu Ala Gly Ile Ile Trp Asp Ser Val Cys Phe Phe
1280                1285                1290

Phe Leu Leu Leu Gln Arg Arg Val Phe Leu Ser His Tyr Tyr Leu
1295                1300                1305

His Val Arg Ala Asp Leu Gln Ala Thr Ala Leu Leu Ala Ser Arg
1310                1315                1320

Gly Phe Ala Leu Tyr Asn Ala Ala Asn Leu Lys Ser Ile Asp Phe
1325                1330                1335

His Arg Arg Ile Glu Glu Lys Ser Leu Ala Gln Leu Lys Arg Gln
1340                1345                1350

Met Glu Arg Ile Arg Ala Lys Gln Glu Lys His Arg Gln Gly Arg
1355                1360                1365

Val Asp Arg Ser Arg Pro Gln Asp Thr Leu Gly Pro Lys Asp Pro
1370                1375                1380

Gly Leu Glu Pro Gly Pro Asp Ser Pro Gly Gly Ser Ser Pro Pro
1385                1390                1395

Arg Arg Gln Trp Trp Arg Pro Trp Leu Asp His Ala Thr Val Ile
1400                1405                1410

His Ser Gly Asp Tyr Phe Leu Phe Glu Ser Asp Ser Glu Glu Glu
1415                1420                1425

Glu Glu Ala Val Pro Glu Asp Pro Arg Pro Ser Ala Gln Ser Ala
1430                1435                1440

Phe Gln Leu Ala Tyr Gln Ala Trp Val Thr Asn Ala Gln Ala Val
1445                1450                1455

Leu Arg Arg Arg Gln Gln Glu Gln Glu Gln Ala Arg Gln Glu Gln
1460                1465                1470

Ala Gly Gln Leu Pro Thr Gly Gly Gly Pro Ser Gln Glu Val Glu
1475                1480                1485

Pro Ala Glu Gly Pro Glu Glu Ala Ala Ala Gly Arg Ser His Val
1490                1495                1500

Val Gln Arg Val Leu Ser Thr Ala Gln Phe Leu Trp Met Leu Gly
1505                1510                1515

Gln Ala Leu Val Asp Glu Leu Thr Arg Trp Leu Gln Glu Phe Thr
```

```
                1520                1525                1530
Arg His His Gly Thr Met Ser Asp Val Leu Arg Ala Glu Arg Tyr
    1535                1540                1545

Leu Leu Thr Gln Glu Leu Leu Gln Gly Gly Glu Val His Arg Gly
    1550                1555                1560

Val Leu Asp Gln Leu Tyr Thr Ser Gln Ala Glu Ala Thr Leu Pro
    1565                1570                1575

Gly Pro Thr Glu Ala Pro Asn Ala Pro Ser Thr Val Ser Ser Gly
    1580                1585                1590

Leu Gly Ala Glu Glu Pro Leu Ser Ser Met Thr Asp Asp Met Gly
    1595                1600                1605

Ser Pro Leu Ser Thr Gly Tyr His Thr Arg Ser Gly Ser Glu Glu
    1610                1615                1620

Ala Val Thr Asp Pro Gly Glu Arg Glu Ala Gly Ala Ser Leu Tyr
    1625                1630                1635

Gln Gly Leu Met Arg Thr Ala Ser Glu Leu Leu Leu Asp Arg Arg
    1640                1645                1650

Leu Arg Ile Pro Glu Leu Glu Glu Ala Glu Leu Phe Ala Glu Gly
    1655                1660                1665

Gln Gly Arg Ala Leu Arg Leu Leu Arg Ala Val Tyr Gln Cys Val
    1670                1675                1680

Ala Ala His Ser Glu Leu Leu Cys Tyr Phe Ile Ile Ile Leu Asn
    1685                1690                1695

His Met Val Thr Ala Ser Ala Gly Ser Leu Val Leu Pro Val Leu
    1700                1705                1710

Val Phe Leu Trp Ala Met Leu Ser Ile Pro Arg Pro Ser Lys Arg
    1715                1720                1725

Phe Trp Met Thr Ala Ile Val Phe Thr Glu Ile Ala Val Val Val
    1730                1735                1740

Lys Tyr Leu Phe Gln Phe Gly Phe Phe Pro Trp Asn Ser His Val
    1745                1750                1755

Val Leu Arg Arg Tyr Glu Asn Lys Pro Tyr Phe Pro Pro Arg Ile
    1760                1765                1770

Leu Gly Leu Glu Lys Thr Asp Gly Tyr Ile Lys Tyr Asp Leu Val
    1775                1780                1785

Gln Leu Met Ala Leu Phe Phe His Arg Ser Gln Leu Leu Cys Tyr
    1790                1795                1800

Gly Leu Trp Asp His Glu Glu Asp Ser Pro Ser Lys Glu His Asp
    1805                1810                1815

Lys Ser Gly Glu Glu Glu Gln Gly Ala Glu Gly Pro Gly Val
    1820                1825                1830

Pro Ala Ala Thr Thr Glu Asp His Ile Gln Val Glu Ala Arg Val
    1835                1840                1845

Gly Pro Thr Asp Gly Thr Pro Glu Pro Gln Val Glu Leu Arg Pro
    1850                1855                1860

Arg Asp Thr Arg Arg Ile Ser Leu Arg Phe Arg Arg Lys Lys
    1865                1870                1875

Glu Gly Pro Ala Arg Lys Gly Ala Ala Ile Glu Ala Glu Asp
    1880                1885                1890

Arg Glu Glu Glu Glu Gly Glu Glu Lys Glu Ala Pro Thr Gly
    1895                1900                1905

Arg Glu Lys Arg Pro Ser Arg Ser Gly Gly Arg Val Arg Ala Ala
    1910                1915                1920
```

Gly Arg Arg Leu Gln Gly Phe Cys Leu Ser Leu Ala Gln Gly Thr
1925                 1930                 1935

Tyr Arg Pro Leu Arg Arg Phe Phe His Asp Ile Leu His Thr Lys
1940                 1945                 1950

Tyr Arg Ala Ala Thr Asp Val Tyr Ala Leu Met Phe Leu Ala Asp
1955                 1960                 1965

Val Val Asp Phe Ile Ile Ile Ile Phe Gly Phe Trp Ala Phe Gly
1970                 1975                 1980

Lys His Ser Ala Ala Thr Asp Ile Thr Ser Ser Leu Ser Asp Asp
1985                 1990                 1995

Gln Val Pro Glu Ala Phe Leu Val Met Leu Leu Ile Gln Phe Ser
2000                 2005                 2010

Thr Met Val Val Asp Arg Ala Leu Tyr Leu Arg Lys Thr Val Leu
2015                 2020                 2025

Gly Lys Leu Ala Phe Gln Val Ala Leu Val Leu Ala Ile His Leu
2030                 2035                 2040

Trp Met Phe Phe Ile Leu Pro Ala Val Thr Glu Arg Met Phe Asn
2045                 2050                 2055

Gln Asn Val Val Ala Gln Leu Trp Tyr Phe Val Lys Cys Ile Tyr
2060                 2065                 2070

Phe Ala Leu Ser Ala Tyr Gln Ile Arg Cys Gly Tyr Pro Thr Arg
2075                 2080                 2085

Ile Leu Gly Asn Phe Leu Thr Lys Lys Tyr Asn His Leu Asn Leu
2090                 2095                 2100

Phe Leu Phe Gln Gly Phe Arg Leu Val Pro Phe Leu Val Glu Leu
2105                 2110                 2115

Arg Ala Val Met Asp Trp Val Trp Thr Asp Thr Thr Leu Ser Leu
2120                 2125                 2130

Ser Ser Trp Met Cys Val Glu Asp Ile Tyr Ala Asn Ile Phe Ile
2135                 2140                 2145

Ile Lys Cys Ser Arg Glu Thr Glu Lys Lys Tyr Pro Gln Pro Lys
2150                 2155                 2160

Gly Gln Lys Lys Lys Lys Ile Val Lys Tyr Gly Met Gly Gly Leu
2165                 2170                 2175

Ile Ile Leu Phe Leu Ile Ala Ile Ile Trp Phe Pro Leu Leu Phe
2180                 2185                 2190

Met Ser Leu Val Arg Ser Val Val Gly Val Val Asn Gln Pro Ile
2195                 2200                 2205

Asp Val Thr Val Thr Leu Lys Leu Gly Gly Tyr Glu Pro Leu Phe
2210                 2215                 2220

Thr Met Ser Ala Gln Gln Pro Ser Ile Ile Pro Phe Thr Ala Gln
2225                 2230                 2235

Ala Tyr Glu Glu Leu Ser Arg Gln Phe Asp Pro Gln Pro Leu Ala
2240                 2245                 2250

Met Gln Phe Ile Ser Gln Tyr Ser Pro Glu Asp Ile Val Thr Ala
2255                 2260                 2265

Gln Ile Glu Gly Ser Ser Gly Ala Leu Trp Arg Ile Ser Pro Pro
2270                 2275                 2280

Ser Arg Ala Gln Met Lys Arg Glu Leu Tyr Asn Gly Thr Ala Asp
2285                 2290                 2295

Ile Thr Leu Arg Phe Thr Trp Asn Phe Gln Arg Asp Leu Ala Lys
2300                 2305                 2310

-continued

| | | | | | | | | | | | | |
|---|---|---|---|---|---|---|---|---|---|---|---|---|
| Gly | Gly 2315 | Thr | Val | Glu | Tyr 2320 | Ala | Asn | Glu | Lys | His 2325 | Met | Leu | Ala | Leu |
| Ala | Pro 2330 | Asn | Ser | Thr | Ala 2335 | Arg | Arg | Gln | Leu | Ala 2340 | Ser | Leu | Leu | Glu |
| Gly | Thr 2345 | Ser | Asp | Gln | Ser 2350 | Val | Val | Ile | Pro | Asn 2355 | Leu | Phe | Pro | Lys |
| Tyr | Ile 2360 | Arg | Ala | Pro | Asn 2365 | Gly | Pro | Glu | Ala | Asn 2370 | Pro | Val | Lys | Gln |
| Leu | Gln 2375 | Pro | Asn | Glu | Glu 2380 | Ala | Asp | Tyr | Leu | Gly 2385 | Val | Arg | Ile | Gln |
| Leu | Arg 2390 | Arg | Glu | Gln | Gly 2395 | Ala | Gly | Ala | Thr | Gly 2400 | Phe | Leu | Glu | Trp |
| Trp | Val 2405 | Ile | Glu | Leu | Gln 2410 | Glu | Cys | Arg | Thr | Asp 2415 | Cys | Asn | Leu | Leu |
| Pro | Met 2420 | Val | Ile | Phe | Ser 2425 | Asp | Lys | Val | Ser | Pro 2430 | Pro | Ser | Leu | Gly |
| Phe | Leu 2435 | Ala | Gly | Tyr | Gly 2440 | Ile | Met | Gly | Leu | Tyr 2445 | Val | Ser | Ile | Val |
| Leu | Val 2450 | Ile | Gly | Lys | Phe 2455 | Val | Arg | Gly | Phe | Phe 2460 | Ser | Glu | Ile | Ser |
| His | Ser 2465 | Ile | Met | Phe | Glu 2470 | Glu | Leu | Pro | Cys | Val 2475 | Asp | Arg | Ile | Leu |
| Lys | Leu 2480 | Cys | Gln | Asp | Ile 2485 | Phe | Leu | Val | Arg | Glu 2490 | Thr | Arg | Glu | Leu |
| Glu | Leu 2495 | Glu | Glu | Glu | Leu 2500 | Tyr | Ala | Lys | Leu | Ile 2505 | Phe | Leu | Tyr | Arg |
| Ser | Pro 2510 | Glu | Thr | Met | Ile 2515 | Lys | Trp | Thr | Arg | Glu 2520 | Lys | Glu | | |

PIEZO TYPE MECHANOSENSITIVE ION CHANNEL COMPONENT 1 (PIEZO1) VARIANTS AND USES THEREOF

REFERENCE TO A SEQUENCE LISTING

This application includes a Sequence Listing submitted electronically as a text file named 18923802501SEQ, created on Feb. 5, 2020, with a size of 132 kilobytes. The Sequence Listing is incorporated by reference herein.

FIELD

The present disclosure provides methods of treating patients having varicose veins, methods of identifying subjects having an increased risk of developing varicose veins, and methods of diagnosing varicose veins in a human subject, comprising detecting the presence of PIEZO1 predicted loss-of-function variant nucleic acid molecules and polypeptides in a biological sample from the patient or subject.

BACKGROUND

Varicose veins is a common multifactorial disease with largely unknown genetic drivers that is often seen in patients with chronic venous insufficiency, together classified as chronic venous disease. Dysfunction of venous valves is associated with varicose veins, venous hypertension, and thrombosis. Several processes, such as changes in hemodynamic forces, endothelial activation, inflammation, hypoxia, and dysregulation of matrix metalloproteinases and their tissue inhibitors have been associated with varicose vein development. Varicose vein risk factors include increased age, female sex, number of pregnancies, obesity, history of deep venous thrombosis, and standing occupation. Varicose veins has also been linked to insufficient lymph drainage and chronic venous insufficiency. In addition, several genome-wide association studies (GWAS) displayed about 18.5% varicose vein heritability.

PIEZO1 is encoded by a 70 kb gene located at 16q24.3 and is present in five potential isoforms. PIEZO1 protein is 2,521 amino acids long, and is a 286 kDa transmembrane protein that contains 38 transmembrane domains and functions as a homo-tetramer. PIEZO1 encodes an evolutionarily conserved endothelial mechanosensitive cation channel, which generates currents characterized by a linear current-voltage relationship that are sensitive to ruthenium red and gadolinium. PIEZO1 is ubiquitously expressed and plays a role in epithelial cell adhesion by maintaining integrin activation through R-Ras recruitment to the endoplasmic reticulum, most probably in its activated state, and subsequent stimulation of calpain signaling. In vasculature, PIEZO1 is involved in endothelial cell migration and sprouting angiogenesis. Specifically, PIEZO1 acts as a sensor for bloodflow-associated shear stress and promotes endothelial cell organization and alignment in the direction of blood flow ensuring proper vessel formation, remodeling, and maturation. PIEZO1 also appears to be required for lymphatic valve formation. Other reported functions include blood pressure regulation, urine osmolarity, erythrocyte integrity, pressure sensing, and collecting duct osmoregulation.

SUMMARY

The present disclosure provides methods of identifying a human subject having an increased risk of developing varicose veins, wherein the method comprises determining or having determined in a biological sample obtained from the subject the presence or absence of: a Piezo Type Mechanosensitive Ion Channel Component 1 (PIEZO1) predicted loss-of-function variant genomic nucleic acid molecule; a PIEZO1 predicted loss-of-function variant mRNA molecule; a PIEZO1 predicted loss-of-function variant cDNA molecule produced from the mRNA molecule; or a PIEZO1 predicted loss-of-function variant polypeptide; wherein: the absence of the PIEZO1 predicted loss-of-function variant genomic nucleic acid molecule, mRNA molecule, cDNA molecule, or polypeptide indicates that the subject does not have an increased risk for developing varicose veins; and the presence of the PIEZO1 predicted loss-of-function variant genomic nucleic acid molecule, mRNA molecule, cDNA molecule, or polypeptide indicates that the subject has an increased risk for developing varicose veins.

The present disclosure also provides methods of diagnosing varicose veins in a human subject, wherein the method comprises detecting in a sample obtained from the subject the presence or absence of: a Piezo Type Mechanosensitive Ion Channel Component 1 (PIEZO1) predicted loss-of-function variant genomic nucleic acid molecule; a PIEZO1 predicted loss-of-function variant mRNA molecule; a PIEZO1 predicted loss-of-function variant cDNA molecule produced from the mRNA molecule; or a PIEZO1 predicted loss-of-function variant polypeptide; wherein when the subject has a PIEZO1 predicted loss-of-function variant genomic nucleic acid molecule, mRNA molecule, cDNA molecule, or polypeptide, and has one or more symptoms of varicose veins, then the subject is diagnosed as having varicose veins.

The present disclosure also provides methods of treating a patient with a therapeutic agent that treats or inhibits varicose veins, wherein the patient is suffering from varicose veins or has an increased risk of developing varicose veins, the method comprising the steps of: determining whether the patient has a Piezo Type Mechanosensitive Ion Channel Component 1 (PIEZO1) predicted loss-of-function variant nucleic acid molecule encoding a human PIEZO1 polypeptide by: obtaining or having obtained a biological sample from the patient; and performing or having performed a genotyping assay on the biological sample to determine if the patient has a genotype comprising the PIEZO1 predicted loss-of-function variant nucleic acid molecule; and when the patient is PIEZO1 reference, then administering or continuing to administer to the patient the therapeutic agent that treats or inhibits the varicose veins in a standard dosage amount; and when the patient is heterozygous or homozygous for a PIEZO1 predicted loss-of-function variant nucleic acid molecule, then administering or continuing to administer to the patient the therapeutic agent that treats or inhibits the varicose veins in an amount that is the same as or greater than the standard dosage amount; wherein the presence of a genotype having the PIEZO1 predicted loss-of-function variant nucleic acid molecule encoding the human PIEZO1 polypeptide indicates the patient has an increased risk of developing varicose veins.

BRIEF DESCRIPTION OF THE FIGURES

The accompanying figures, which are incorporated in and constitute a part of this specification, illustrate several aspects and together with the description serve to explain the principles of the present disclosure.

FIG. 4 shows Single-point and aggregate results for the 65 pLOF variants in PIEZO1.

FIG. 5 shows LD Assessment for PIEZO1.

DESCRIPTION

Figure 1:
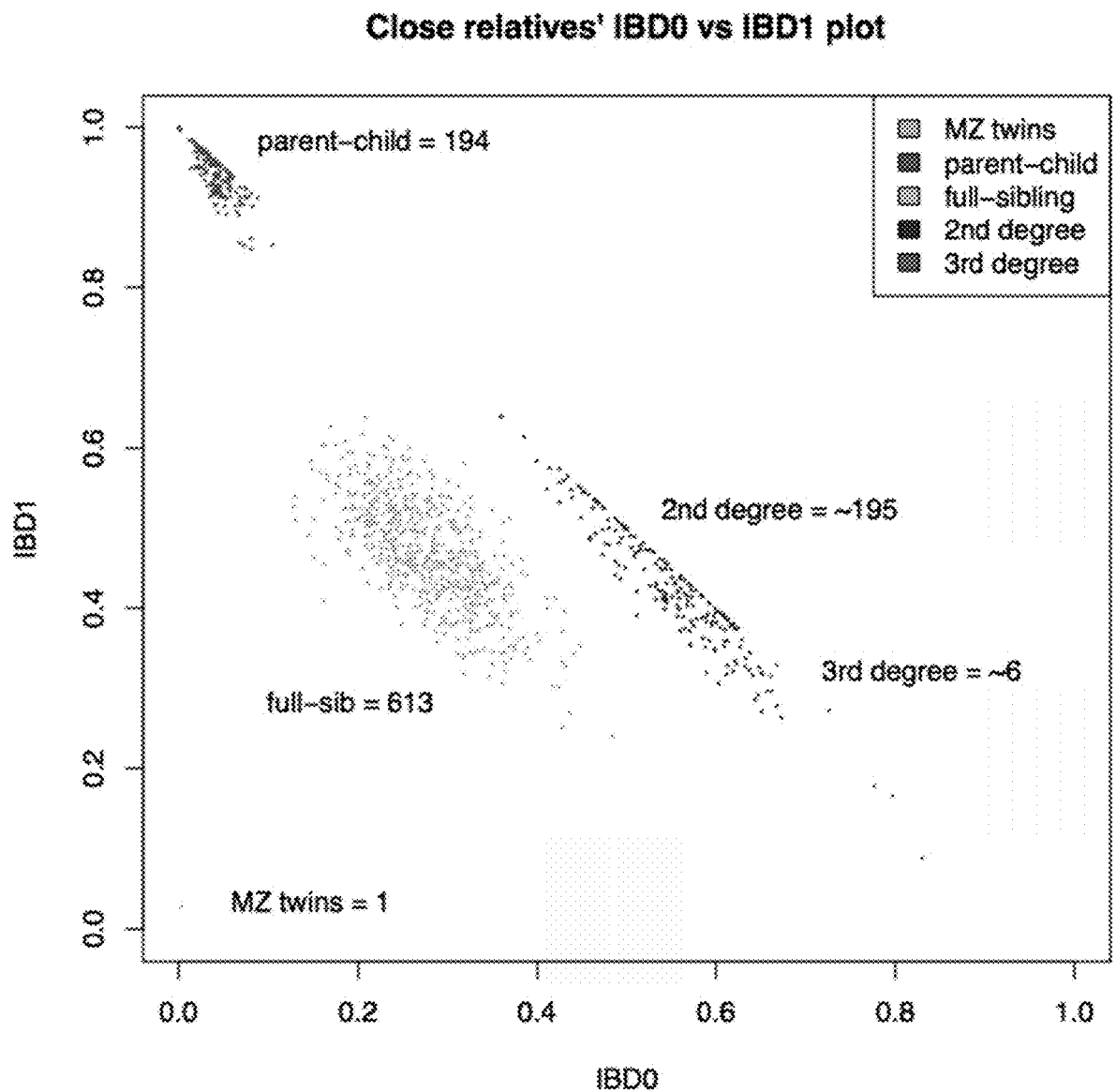
FIG. 1 shows a representative distribution of IBD sharing for pairs of individuals in UKB 50k WES; estimated proportion of WES genotypes with no alleles identical by descent (IBD) vs. 1 allele IBD amongst all pairs of UKB 50k exome participants.

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the terms "subject" and "patient" are used interchangeably. A subject may include any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human.

As used herein, a "nucleic acid," a "nucleic acid molecule," a "nucleic acid sequence," a "polynucleotide," or an "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "comprising" may be replaced with "consisting" or "consisting essentially of" in particular embodiments as desired.

As used herein, the phrase "corresponding to" or grammatical variations thereof when used in the context of the numbering of a particular amino acid or nucleotide sequence or position refers to the numbering of a specified reference sequence when the particular amino acid or nucleotide sequence is compared to the reference sequence (e.g., with the reference sequence herein being the nucleic acid molecule or polypeptide of (wild type) PIEZO1). In other words, the residue (e.g., amino acid or nucleotide) number or residue (e.g., amino acid or nucleotide) position of a particular polymer is designated with respect to the reference sequence rather than by the actual numerical position of the residue within the particular amino acid or nucleotide sequence. For example, a particular amino acid sequence can be aligned to a reference sequence by introducing gaps to optimize residue matches between the two sequences. In these cases, although the gaps are present, the numbering of the residue in the particular amino acid or nucleotide sequence is made with respect to the reference sequence to which it has been aligned.

It has been observed in accordance with the present disclosure that certain variations in PIEZO1 associate with a risk of developing varicose veins. It is believed that no variants of the PIEZO1 gene or protein have any known association with varicose veins in human beings. Therefore, human subjects having PIEZO1 alterations that associate with varicose veins may be treated such that varicose veins is inhibited, the symptoms thereof are reduced, and/or development of symptoms is repressed. Accordingly, the present disclosure provides methods for leveraging the identification of such variants in subjects to identify or stratify risk in such subjects of developing varicose veins, or to diagnose subjects as having varicose veins, such that subjects at risk or subjects with active disease may be treated.

For purposes of the present disclosure, any particular human can be categorized as having one of three PIEZO1 genotypes: i) PIEZO1 reference; ii) heterozygous for a PIEZO1 predicted loss-of-function variant, and iii) homozygous for a PIEZO1 predicted loss-of-function variant. A human is PIEZO1 reference when the human does not have a copy of a PIEZO1 predicted loss-of-function variant nucleic acid molecule. A human is heterozygous for a PIEZO1 predicted loss-of-function variant when the human has a single copy of a PIEZO1 predicted loss-of-function variant nucleic acid molecule. A PIEZO1 predicted loss-of-function variant nucleic acid molecule is any PIEZO1 nucleic acid molecule (such as, a genomic nucleic acid molecule, an mRNA molecule, or a cDNA molecule) encoding a PIEZO1 polypeptide having a partial loss-of-function, a complete loss-of-function, a predicted partial loss-of-function, or a predicted complete loss-of-function. A human who has a PIEZO1 polypeptide having a partial loss-of-function (or predicted partial loss-of-function) is hypomorphic for PIEZO1. The PIEZO1 predicted loss-of-function variant nucleic acid molecule can be any variant nucleic acid molecule described herein. A human is homozygous for a PIEZO1 predicted loss-of-function variant when the human has two copies of any of the PIEZO1 predicted loss-of-function variant nucleic acid molecules.

For human subjects or patients that are genotyped or determined to be heterozygous or homozygous for a PIEZO1 predicted loss-of-function variant nucleic acid molecule, such human subjects or patients have an increased risk of developing varicose veins. For human subjects or patients that are genotyped or determined to be heterozygous or homozygous for a PIEZO1 predicted loss-of-function variant nucleic acid molecule, such human subjects or patients can be treated with an agent effective to treat varicose veins.

The present disclosure provides methods of identifying a human subject having an increased risk of developing varicose veins, wherein the method comprises determining or having determined in a biological sample obtained from the subject the presence or absence of a PIEZO1 predicted loss-of-function variant nucleic acid molecule (such as a genomic nucleic acid molecule, mRNA molecule, and/or cDNA molecule) or polypeptide; wherein the absence of the PIEZO1 predicted loss-of-function variant nucleic acid molecule or polypeptide indicates that the subject does not have an increased risk for developing varicose veins; and the presence of the PIEZO1 predicted loss-of-function variant genomic nucleic acid molecule, mRNA molecule, cDNA molecule, or polypeptide indicates that the subject has an increased risk for developing varicose veins.

The present disclosure also provides methods of identifying a human subject having an increased risk of developing varicose veins, wherein the method comprises determining or having determined in a biological sample obtained from the subject the presence or absence of: i) a PIEZO1 predicted loss-of-function variant genomic nucleic acid molecule; ii) a PIEZO1 predicted loss-of-function variant mRNA molecule; iii) a PIEZO1 predicted loss-of-function variant cDNA molecule produced from the mRNA molecule; or iv) a PIEZO1 predicted loss-of-function variant polypeptide; wherein: the absence of the PIEZO1 predicted loss-of-function variant genomic nucleic acid molecule, mRNA molecule, cDNA molecule, or polypeptide indicates that the subject does not have an increased risk for developing varicose veins; and the presence of the PIEZO1 predicted loss-of-function variant genomic nucleic acid molecule, mRNA molecule, cDNA molecule, or polypeptide indicates that the subject has an increased risk for developing varicose veins.

The present disclosure also provides methods of identifying a human subject having an increased risk for developing varicose veins, wherein the method comprises: determining or having determined in a biological sample obtained from the subject the presence or absence of a PIEZO1 predicted loss-of-function variant nucleic acid molecule (such as a genomic nucleic acid molecule, mRNA molecule, and/or cDNA molecule) encoding a human PIEZO1 polypeptide; wherein: i) when the human subject lacks a PIEZO1 predicted loss-of-function variant nucleic acid molecule (i.e., the human subject is genotypically categorized as a PIEZO1 reference), then the human subject does not have an increased risk for developing varicose veins; and ii) when the human subject has a PIEZO1 predicted loss-of-function variant nucleic acid molecule (i.e., the human subject is categorized as heterozygous for a PIEZO1 predicted loss-of-function variant or homozygous for a PIEZO1 predicted loss-of-function variant), then the human subject has an increased risk for developing varicose veins.

In any of the embodiments described herein, the PIEZO1 predicted loss-of-function variant nucleic acid molecule can be any PIEZO1 nucleic acid molecule (such as, for example, genomic nucleic acid molecule, mRNA molecule, or cDNA molecule) encoding a PIEZO1 polypeptide having a partial loss-of-function, a complete loss-of-function, a predicted partial loss-of-function, or a predicted complete loss-of-function. For example, the PIEZO1 predicted loss-of-function variant nucleic acid molecule can be any of the PIEZO1 variant nucleic acid molecules described herein.

Determining whether a human subject has a PIEZO1 predicted loss-of-function variant nucleic acid molecule in a biological sample can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the human subject.

In any of the embodiments described herein, the varicose veins can be early stage varicose veins (e.g., C0 according to CEAP (Clinical, Etiological, Anatomical, and Pathophysiological) classification). In some embodiments, the varicose veins can be late stage varicose veins (e.g., C6 according to CEAP classification). In some embodiments, the varicose veins can be at any disease stage (e.g., C0-C6 according to CEAP classification). In some embodiments, the human subject is a female.

In some embodiments, when a human subject is identified as having an increased risk of developing varicose veins, the human subject is further treated with a therapeutic agent that treats or inhibits varicose veins, as described herein. For example, when the human subject is heterozygous or homozygous for a PIEZO1 predicted loss-of-function variant nucleic acid molecule, and therefore has an increased risk for developing varicose veins, the human subject is administered a therapeutic agent that treats or inhibits varicose veins. In some embodiments, when the patient is homozygous for a PIEZO1 predicted loss-of-function variant nucleic acid molecule, the patient is administered the therapeutic agent that treats or inhibits varicose veins in a dosage amount that is the same as or greater than the standard dosage amount administered to a patient who is heterozygous for a PIEZO1 predicted loss-of-function variant nucleic acid molecule. In some embodiments, the patient is heterozygous for a PIEZO1 predicted loss-of-function variant nucleic acid molecule. In some embodiments, the patient is homozygous for a PIEZO1 predicted loss-of-function variant nucleic acid molecule.

The present disclosure provides methods of diagnosing varicose veins in a human subject, wherein the methods comprise detecting in a sample obtained from the subject the presence or absence of a PIEZO1 predicted loss-of-function variant nucleic acid molecule (such as a genomic nucleic acid molecule, mRNA molecule, and/or cDNA molecule) or polypeptide; wherein when the subject has a PIEZO1 predicted loss-of-function variant genomic nucleic acid molecule, mRNA molecule, cDNA molecule, or polypeptide, and has one or more symptoms of varicose veins, then the subject is diagnosed as having varicose veins.

The present disclosure also provides methods of diagnosing varicose veins in a human subject, wherein the methods comprise detecting in a sample obtained from the subject the presence or absence of: i) a PIEZO1 predicted loss-of-function variant genomic nucleic acid molecule; ii) a PIEZO1 predicted loss-of-function variant mRNA molecule; iii) a PIEZO1 predicted loss-of-function variant cDNA molecule produced from the mRNA molecule; or iv) a PIEZO1 predicted loss-of-function variant polypeptide; wherein when the subject has a PIEZO1 predicted loss-of-function variant genomic nucleic acid molecule, mRNA molecule, cDNA molecule, or polypeptide, and has one or more symptoms of varicose veins, then the subject is diagnosed as having varicose veins.

The present disclosure also provides methods of diagnosing varicose veins in a human subject, wherein the methods comprise detecting in a sample obtained from the subject the presence or absence of a PIEZO1 predicted loss-of-function variant nucleic acid molecule (such as a genomic nucleic acid molecule, mRNA molecule, and/or cDNA molecule) encoding a human PIEZO1 polypeptide; wherein when the subject has a PIEZO1 predicted loss-of-function variant genomic nucleic acid molecule, mRNA molecule, cDNA molecule, or polypeptide (i.e., the human subject is categorized as heterozygous or homozygous for a PIEZO1 predicted loss-of-function variant nucleic acid molecule), and has one or more symptoms of varicose veins, then the subject is diagnosed as having varicose veins In any of the embodiments described herein, the PIEZO1 predicted loss-of-function variant nucleic acid molecule can be any PIEZO1 nucleic acid molecule (such as, for example, genomic nucleic acid molecule, mRNA molecule, or cDNA molecule) encoding a PIEZO1 polypeptide having a partial loss-of-function, a complete loss-of-function, a predicted partial loss-of-function, or a predicted complete loss-of-function. For example, the PIEZO1 predicted loss-of-function variant nucleic acid molecule can be any of the PIEZO1 variant nucleic acid molecules described herein.

Detecting the presence or absence of a PIEZO1 predicted loss-of-function variant nucleic acid molecule in a sample obtained from the subject can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the human subject.

In any of the embodiments described herein, the varicose veins can be early stage varicose veins (e.g., C0 according to CEAP (Clinical, Etiological, Anatomical, and Pathophysiological) classification). In some embodiments, the varicose veins can be late stage varicose veins (e.g., C6 according to CEAP classification). In some embodiments, the varicose veins can be at any disease stage (e.g., C0-C6 according to CEAP classification). In some embodiments, the human subject is a female.

In some embodiments, when a human subject is diagnosed as having varicose veins, the human subject is further treated with a therapeutic agent that treats or inhibits varicose veins, as described herein. For example, when the human subject is determined to be heterozygous or homozygous for a PIEZO1 predicted loss-of-function variant nucleic acid molecule, and has one or more symptoms of varicose veins, the human subject is administered a therapeutic agent that treats or inhibits varicose veins. In some embodiments, when the patient is homozygous for a PIEZO1 predicted loss-of-function variant nucleic acid molecule, the patient is administered the therapeutic agent that treats or inhibits varicose veins in a dosage amount that is the same as or greater than the standard dosage amount administered to a patient who is heterozygous for a PIEZO1 predicted loss-of-function variant nucleic acid molecule. In some embodiments, the patient is heterozygous for a PIEZO1 predicted loss-of-function variant nucleic acid molecule. In some embodiments, the patient is homozygous for a PIEZO1 predicted loss-of-function variant nucleic acid molecule.

The present disclosure also provides methods of treating a patient with a therapeutic agent that treats or inhibits varicose veins, wherein the patient is suffering from varicose veins or has an increased risk of developing varicose veins, the methods comprising the steps of: determining whether the patient has a PIEZO1 predicted loss-of-function variant nucleic acid molecule encoding a human PIEZO1 polypeptide by: obtaining or having obtained a biological sample from the patient; and performing or having performed a genotyping assay on the biological sample to determine if the patient has a genotype comprising the PIEZO1 predicted loss-of-function variant nucleic acid molecule; and when the patient is PIEZO1 reference, then administering or continuing to administer to the patient the therapeutic agent that treats or inhibits the varicose veins in a standard dosage amount; and when the patient is heterozygous or homozygous for a PIEZO1 predicted loss-of-function variant nucleic acid molecule, then administering or continuing to administer to the patient the therapeutic agent that treats or inhibits the varicose veins in an amount that is the same as or greater than the standard dosage amount; wherein the presence of a genotype having the PIEZO1 predicted loss-of-function variant nucleic acid molecule encoding the human PIEZO1 polypeptide indicates the patient has an increased risk of developing varicose veins. In some embodiments, the patient is heterozygous for a PIEZO1 predicted loss-of-function variant nucleic acid molecule. In some embodiments, the patient is homozygous for a PIEZO1 predicted loss-of-function variant nucleic acid molecule.

In any of the embodiments described herein, the PIEZO1 predicted loss-of-function variant nucleic acid molecule can be any PIEZO1 nucleic acid molecule (such as, for example, genomic nucleic acid molecule, mRNA molecule, or cDNA molecule) encoding a PIEZO1 polypeptide having a partial loss-of-function, a complete loss-of-function, a predicted partial loss-of-function, or a predicted complete loss-of-function. For example, the PIEZO1 predicted loss-of-function variant nucleic acid molecule can be any of the PIEZO1 variant nucleic acid molecules described herein.

The genotyping assay to determine whether a patient has a PIEZO1 predicted loss-of-function variant nucleic acid molecule encoding a human PIEZO1 polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the human subject.

In some embodiments, when the patient is homozygous for a PIEZO1 predicted loss-of-function variant nucleic acid molecule, the patient is administered the therapeutic agent that treats or inhibits varicose veins in a dosage amount that is the same as or greater than the standard dosage amount administered to a patient who is heterozygous for a PIEZO1 predicted loss-of-function variant nucleic acid molecule.

The present disclosure also provides methods of treating a patient with a therapeutic agent that treats or inhibits varicose veins, wherein the patient is suffering from varicose veins or has an increased risk of developing varicose veins, the methods comprising the steps of: determining whether the patient has a PIEZO1 predicted loss-of-function variant polypeptide by: obtaining or having obtained a biological sample from the patient; and performing or having performed an assay on the biological sample to determine if the patient has a PIEZO1 predicted loss-of-function variant polypeptide; and when the patient does not have a PIEZO1 predicted loss-of-function variant polypeptide, then administering or continuing to administer to the patient the therapeutic agent that treats or inhibits the varicose veins in a standard dosage amount; and when the patient has a PIEZO1 predicted loss-of-function variant polypeptide, then administering or continuing to administer to the patient the therapeutic agent that treats or inhibits the varicose veins in an amount that is the same as or greater than the standard dosage amount; wherein the presence of a PIEZO1 predicted loss-of-function variant polypeptide indicates the patient has an increased risk of developing varicose veins. In some embodiments, the patient has a PIEZO1 predicted loss-of-function variant polypeptide. In some embodiments, the patient does not have a PIEZO1 predicted loss-of-function variant polypeptide.

The assay to determine whether a patient has a PIEZO1 predicted loss-of-function variant polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the human subject.

In any of the embodiments described herein, the PIEZO1 predicted loss-of-function variant polypeptide can be any PIEZO1 polypeptide having a partial loss-of-function, a complete loss-of-function, a predicted partial loss-of-function, or a predicted complete loss-of-function. For example, the PIEZO1 predicted loss-of-function variant polypeptide can be any of the PIEZO1 variant polypeptides described herein.

In any of the embodiments described herein, the varicose veins can be early stage varicose veins (e.g., C0 according to CEAP (Clinical, Etiological, Anatomical, and Pathophysiological) classification). In some embodiments, the varicose veins can be late stage varicose veins (e.g., C6 according to CEAP classification). In some embodiments, the varicose veins can be at any disease stage (e.g., C0-C6 according to CEAP classification). In some embodiments, the human subject is a female.

Symptoms of varicose veins include, but are not limited to, heavy legs, appearance of spider veins (telangiectasia) in the affected leg, ankle swelling, especially in the evening, brownish-yellow shiny skin discoloration near the affected veins, redness, dryness, and itchiness of areas of skin (termed stasis dermatitis or venous eczema), cramps especially developing when making a sudden move such as standing up, minor injuries to the affected area, bleeding more than normal or taking a long time to heal, shrinking of the skin above the ankle (lipodermatosclerosis), restless legs syndrome, whitened, irregular scar-like patches appearing at the ankles (atrophie blanche), or any combination thereof.

Examples of therapeutic agents that treat or inhibit varicose veins include, but are not limited to flavonoids, such as diosmin or hesperidin, and anti-inflammatory agents, such as ibuprofen and aspirin.

In some embodiments, the dose of the therapeutic agents that treat or inhibit varicose veins can be reduced by about 10%, by about 20%, by about 30%, by about 40%, by about 50%, by about 60%, by about 70%, by about 80%, or by about 90% for patients or human subjects that are heterozygous for a PIEZO1 predicted loss-of-function variant nucleic acid molecule (i.e., a lower than the standard dosage amount) compared to patients or human subjects that are homozygous for a PIEZO1 predicted loss-of-function variant nucleic acid molecule (who may receive a standard dosage amount). In some embodiments, the dose of the therapeutic agents that treat or inhibit varicose veins can be reduced by about 10%, by about 20%, by about 30%, by about 40%, or by about 50%. In addition, the dose of therapeutic agents that treat or inhibit varicose veins in patients or human subjects that are heterozygous for a PIEZO1 predicted loss-of-function variant nucleic acid molecule can be administered less frequently compared to patients or human subjects that are homozygous for a PIEZO1 predicted loss-of-function variant nucleic acid molecule.

Administration of the therapeutic agents that treat or inhibit varicose veins can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a patient can receive therapy for a prolonged period of time such as, for example, 6 months, 1 year, or more.

Administration of the therapeutic agents that treat or inhibit varicose veins can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in varicose veins, a decrease/reduction in the severity of varicose veins (such as, for example, a reduction or inhibition of development of varicose veins), a decrease/reduction in symptoms and varicose vein-related effects, delaying the onset of symptoms and varicose vein-related effects, reducing the severity of symptoms of varicose vein-related effects, reducing the severity of an acute episode, reducing the number of symptoms and varicose vein-related effects, reducing the latency of symptoms and varicose vein-related effects, an amelioration of symptoms and varicose vein-related effects, reducing secondary symptoms, reducing secondary infections, preventing relapse to varicose veins, decreasing the number or frequency of relapse episodes, increasing latency between symptomatic episodes, increasing time to sustained progression, speeding recovery, and/or increasing efficacy of or decreasing resistance to alternative therapeutics, following administration of the agent or composition comprising the agent. A prophylactic effect may comprise a complete or partial avoidance/inhibition or a delay of varicose vein development/progression (such as, for example, a complete or partial avoidance/inhibition or a delay) following administration of a therapeutic protocol. Treatment of varicose veins encompasses the treatment of patients already diagnosed as having any form of varicose veins at any clinical stage or manifestation, the delay of the onset or evolution or aggravation or deterioration of the symptoms or signs of varicose veins, and/or preventing and/or reducing the severity of varicose veins.

The present disclosure also provides, in any of the methods described herein, the detection or determination of the presence of a PIEZO1 predicted loss-of-function variant genomic nucleic acid molecule, a PIEZO1 predicted loss-of-function variant mRNA molecule, and/or a PIEZO1 predicted loss-of-function variant cDNA molecule in a biological sample from a subject human. It is understood that gene sequences within a population and mRNA molecules encoded by such genes can vary due to polymorphisms such as single-nucleotide polymorphisms. The sequences provided herein for the PIEZO1 variant nucleic acid molecules disclosed herein are only exemplary sequences. Other sequences for the PIEZO1 variant nucleic acid molecules are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting any PIEZO1 variant nucleic acid molecule, preliminary processing designed to isolate or enrich the sample for the genomic DNA can be employed. A variety of known techniques may be used for this purpose. When detecting the level of any PIEZO1 variant mRNA, different techniques can be used enrich the biological sample with mRNA. Various methods to detect the presence or level of a mRNA or the presence of a particular variant genomic DNA locus can be used.

In some embodiments, detecting a human PIEZO1 predicted loss-of-function variant nucleic acid molecule in a human subject comprises assaying or genotyping a biological sample obtained from the human subject to determine whether a PIEZO1 genomic nucleic acid molecule, a PIEZO1 mRNA molecule, or a PIEZO1 cDNA molecule produced from an mRNA molecule in the biological sample comprises one or more variations that cause a loss-of-function (partial or complete) or are predicted to cause a loss-of-function (partial or complete).

In some embodiments, the methods of detecting the presence or absence of a PIEZO1 predicted loss-of-function variant nucleic acid molecule (such as, for example, a genomic nucleic acid molecule, an mRNA molecule, and/or a cDNA molecule) in a human subject, comprise: performing an assay on a biological sample obtained from the human subject, which assay determines whether a nucleic acid molecule in the biological sample comprises a particular nucleotide sequence.

In some embodiments, the biological sample comprises a cell or cell lysate. Such methods can further comprise, for example, obtaining a biological sample from the subject comprising a PIEZO1 genomic nucleic acid molecule or mRNA molecule, and if mRNA, optionally reverse transcribing the mRNA into cDNA. Such assays can comprise, for example determining the identity of these positions of the particular PIEZO1 nucleic acid molecule. In some embodiments, the method is an in vitro method.

In some embodiments, the determining step, detecting step, or genotyping assay comprises sequencing at least a portion of the nucleotide sequence of the PIEZO1 genomic nucleic acid molecule, the PIEZO1 mRNA molecule, or the PIEZO1 cDNA molecule produced from the mRNA molecule in the biological sample, wherein the sequenced portion comprises one or more variations that cause a loss-of-function (partial or complete) or are predicted to cause a loss-of-function (partial or complete).

In any of the methods described herein, the determining step, detecting step, or genotyping assay comprises sequencing at least a portion of the nucleotide sequence of the PIEZO1 nucleic acid molecule in the biological sample, wherein the sequenced portion comprises a position corresponding to a predicted loss-of-function variant position, wherein when a variant nucleotide at the predicted loss-of-function variant position is detected, the PIEZO1 nucleic acid molecule in the biological sample is a PIEZO1 predicted loss-of-function variant nucleic acid molecule.

In some embodiments, the determining step, detecting step, or genotyping assay comprises: a) contacting the biological sample with a primer hybridizing to a portion of the nucleotide sequence of the PIEZO1 nucleic acid molecule that is proximate to a predicted loss-of-function variant position; b) extending the primer at least through the predicted loss-of-function variant position; and c) determining whether the extension product of the primer comprises a variant nucleotide at the predicted loss-of-function variant position.

In some embodiments, the assay comprises sequencing the entire nucleic acid molecule. In some embodiments, only a PIEZO1 genomic nucleic acid molecule is analyzed. In some embodiments, only a PIEZO1 mRNA is analyzed. In some embodiments, only a PIEZO1 cDNA obtained from PIEZO1 mRNA is analyzed.

In some embodiments, the determining step, detecting step, or genotyping assay comprises: a) amplifying at least a portion of the PIEZO1 nucleic acid molecule that encodes the human PIEZO1 polypeptide, wherein the portion comprises a predicted loss-of-function variant position; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the predicted loss-of-function variant position; and d) detecting the detectable label.

In some embodiments, the nucleic acid molecule is mRNA and the determining step further comprises reverse-transcribing the mRNA into a cDNA prior to the amplifying step.

In some embodiments, the determining step, detecting step, or genotyping assay comprises: contacting the nucleic acid molecule in the biological sample with an alteration-specific probe comprising a detectable label, wherein the alteration-specific probe comprises a nucleotide sequence which hybridizes under stringent conditions to a predicted loss-of-function variant position; and detecting the detectable label.

The alteration-specific probes or alteration-specific primers described herein comprise a nucleic acid sequence which is complementary to and/or hybridizes, or specifically hybridizes, to a PIEZO1 predicted loss-of-function variant nucleic acid molecule, or the complement thereof. In some embodiments, the alteration-specific probes or alteration-specific primers comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, or at least about 50 nucleotides. In some embodiments, the alteration-specific probes or alteration-specific primers comprise or consist of at least 15 nucleotides. In some embodiments, the alteration-specific probes or alteration-specific primers comprise or consist of at least 15 nucleotides to at least about 35 nucleotides. In some embodiments, alteration-specific probes or alteration-specific primers hybridize to PIEZO1 predicted loss-of-function variant genomic nucleic acid molecules, PIEZO1 predicted loss-offunction variant mRNA molecules, and/or PIEZO1 predicted loss-of-function variant cDNA molecules under stringent conditions.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the human subject.

In any of the embodiments described herein, the PIEZO1 predicted loss-of-function variant nucleic acid molecule can be any PIEZO1 nucleic acid molecule (such as, for example, genomic nucleic acid molecule, mRNA molecule, or cDNA molecule) encoding a PIEZO1 polypeptide having a partial loss-of-function, a complete loss-of-function, a predicted partial loss-of-function, or a predicted complete loss-of-function. For example, the PIEZO1 predicted loss-of-function variant nucleic acid molecule can be any of the PIEZO1 variant nucleic acid molecules described herein.

In some embodiments, the assay comprises contacting the biological sample with a primer or probe, such as an alteration-specific primer or alteration-specific probe, that specifically hybridizes to a PIEZO1 variant genomic sequence, variant mRNA sequence, or variant cDNA sequence and not the corresponding PIEZO1 reference sequence under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a PIEZO1 variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides molecular complexes comprising any of the PIEZO1 nucleic acid molecules (genomic nucleic acid molecules, mRNA molecules, or cDNA molecules), or complement thereof, described herein and any of the alteration-specific primers or alteration-specific probes described herein. In some embodiments, the PIEZO1 nucleic acid molecules (genomic nucleic acid molecules, mRNA molecules, or cDNA molecules), or complement thereof, in the molecular complexes are single-stranded. In some embodiments, the PIEZO1 nucleic acid molecule is any of the genomic nucleic acid molecules described herein. In some embodiments, the PIEZO1 nucleic acid molecule is any of the mRNA molecules described herein. In some embodiments, the PIEZO1 nucleic acid molecule is any of the cDNA molecules described herein. In some embodiments, the molecular complex comprises any of the PIEZO1 nucleic acid molecules (genomic nucleic acid molecules, mRNA molecules, or cDNA molecules), or complement thereof, described herein and any of the alteration-specific primers described herein. In some embodiments, the molecular complex comprises any of the PIEZO1 nucleic acid molecules (genomic nucleic acid molecules, mRNA molecules, or cDNA molecules), or complement thereof, described herein and any of the alteration-specific probes described herein. In some embodiments, the molecular complex comprises a non-human polymerase.

In some embodiments, detecting the presence of a human PIEZO1 predicted loss-of-function polypeptide comprises performing an assay on a sample obtained from a human subject to determine whether a PIEZO1 polypeptide in the subject contains one or more variations that causes the polypeptide to have a loss-of-function (partial or complete) or predicted loss-of-function (partial or complete). In some embodiments, the assay comprises sequencing at least a portion of the PIEZO1 polypeptide that comprises a variant position. In some embodiments, the detecting step comprises sequencing the entire polypeptide. Identification of a variant amino acid at the variant position of the PIEZO1 polypeptide indicates that the PIEZO1 polypeptide is a PIEZO1 predicted loss-of-function polypeptide. In some embodiments, the assay comprises an immunoassay for detecting the presence of a polypeptide that comprises a variant. Detection of a variant amino acid at the variant position of the PIEZO1 polypeptide indicates that the PIEZO1 polypeptide is a PIEZO1 predicted loss-of-function polypeptide.

The probes and/or primers (including alteration-specific probes and alteration-specific primers) described herein comprise or consist of from about 15 to about 100, from about 15 to about 35 nucleotides. In some embodiments, the alteration-specific probes and alteration-specific primers comprise DNA. In some embodiments, the alteration-specific probes and alteration-specific primers comprise RNA. In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers (including alteration-specific probes and alteration-specific primers) specifically hybridize to any of the nucleic acid molecules disclosed herein under stringent conditions. In the context of the disclosure "specifically hybridizes" means that the probe or primer (including alteration-specific probes and alteration-specific primers) does not hybridize to a nucleic acid sequence encoding a PIEZO1 reference genomic nucleic acid molecule, a PIEZO1 reference mRNA molecule, and/or a PIEZO1 reference cDNA molecule. In some embodiments, the probes (such as, for example, an alteration-specific probe) comprise a label. In some embodiments, the label is a fluorescent label, a radiolabel, or biotin.

The nucleotide sequence of a PIEZO1 reference genomic nucleic acid molecule is set forth in SEQ ID NO:1, which is 69,883 nucleotides in length. The first nucleotide recited in SEQ ID NO:1 corresponds to the nucleotide at position 88,715,338 of chromosome 16 (see, hg38_knownGene_ENST00000301015.14).

Numerous variant genomic nucleic acid molecule of PIEZO1 exist, including, but not limited to (using the human genome reference build GRch38): 16:88715629:G:A, 16:88715728:G:T, 16:88715767:G:A, 16:88715802:C:A, 16:88715822:D:4, 16:88715987:I:1, 16:88716359:A:G, 16:88716570:C:T, 16:88716874:G:A, 16:88717213:T:A, 16:88719588:G:A, 16:88719722:C:G, 16:88719870:G:T, 16:88720068:D:2, 16:88720229:C:A, 16:88720248:D:4, 16:88720394:C:T, 16:88720644:D:1, 16:88720698:D:1, 16:88720698:I:1, 16:88721165:C:A, 16:88721268:D:1, 16:88721307:G:A, 16:88721586:G:C, 16:88721652:G:C, 16:88722217:C:T, 16:88722605:I:1, 16:88723005:I:7, 16:88723253:G:A, 16:88723311:C:T, 16:88725081:C:A, 16:88726282:G:A, 16:88726546:C:T, 16:88726619:G:A, 16:88726924:G:A, 16:88727038:C:T, 16:88727072:D:1, 16:88727163:G:A, 16:88731768:D:1, 16:88732334:C:G, 16:88732411:D:1, 16:88732720:D:1, 16:88733326:G:C, 16:88733337:D:4, 16:88733587:C:A, 16:88733965:D:1, 16:88734017:C:A, 16:88734042:I:1, 16:88734679:C:T, 16:88734909:I:1, 16:88736167:D:2, 16:88736324:G:A, 16:88736391:G:T, 16:88736409:C:T, 16:88736671:G:A, 16:88737557:A:C, 16:88737727:C:G, 16:88737815:C:T, 16:88738283:G:C, 16:88738637:G:A, 16:88738735:D:1, 16:88741477:C:T, 16:88742306:D:1, 16:88749399:G:A, and 16:88784929:C:T. Thus, for example, using the SEQ ID NO:1 reference genomic nucleotide sequence as a base (with the first nucleotide listed therein designated as position 88,715,338), the first listed variant (16:88715629:G:A) would have a guanine replaced with an adenine (designated the "variant nucleotide") at position 88,715,629 (designated the "variant position"). Those variants designated as a "D" followed by a number have a deletion of the stated number of nucleotides. Those variants designated as an "I" followed by a number have an insertion of the stated number of nucleotides (any nucleotide). Any of these PIEZO1 predicted loss-of-function variant genomic nucleic acid molecules can be detected in any of the methods described herein.

The nucleotide sequence of a PIEZO1 reference mRNA molecule is set forth in SEQ ID NO:2 (see, NCBI Reference Sequence: NM_001142864.4), which is 8,089 nucleotides in length. The variant nucleotides at their respective variant positions for the variant genomic nucleic acid molecules described herein also have corresponding variant nucleotides at their respective variant positions for the variant mRNA molecules based upon the PIEZO1 reference mRNA sequence according to SEQ ID NO:2. Any of these PIEZO1 predicted loss-of-function variant mRNA molecules can be detected in any of the methods described herein.

The nucleotide sequence of a PIEZO1 reference cDNA molecule is set forth in SEQ ID NO:3 (based upon NCBI Reference Sequence: NM_001142864.4), which is 8,089 nucleotides in length. The variant nucleotides at their respective variant positions for the variant genomic nucleic acid molecules described herein also have corresponding variant nucleotides at their respective variant positions for the variant cDNA molecules based upon the PIEZO1 reference cDNA sequence according to SEQ ID NO:3. Any of these PIEZO1 predicted loss-of-function variant cDNA molecules can be detected in any of the methods described herein.

The amino acid sequence of a PIEZO1 reference polypeptide is set forth in SEQ ID NO:4 (see, UniProt Accession No. Q92508.4 and NCBI RefSeq accession NM_001142864.4), which is 2,521 amino acids in length. Using the translated nucleotide sequence of either the PIEZO1 mRNA or cDNA molecules, the PIEZO1 variant polypeptides having corresponding translated variant amino acids at variant positions (codons). Any of these PIEZO1 predicted loss-of-function variant polypeptides can be detected in any of the methods described herein.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence. In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned. A variety of computational algorithms exist that can be used for performing a sequence alignment to identify a nucleotide or amino acid position in one polymeric molecule that corresponds to a nucleotide or amino acid position in another polymeric molecule. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: Materials and Methods

WES Sample Preparation and Sequencing

Genomic DNA samples normalized to approximately 16 ng/µl were transferred in house from the UK Biobank in 0.5 ml 2D matrix tubes (Thermo Fisher Scientific) and stored in an automated sample biobank (LiCONiC Instruments) at −80° C. prior to sample preparation. One sample had insufficient DNA for sequencing. Exome capture was completed using a high-throughput, fully-automated approach developed in house. Briefly, DNA libraries were created by enzymatically shearing 100 ng of genomic DNA to a mean fragment size of 200 base pairs using a custom NEBNext Ultra II FS DNA library prep kit (New England Biolabs) and a common Y-shaped adapter (Integrated DNA Technologies) was ligated to all DNA libraries. Unique, asymmetric 10 base pair barcodes were added to the DNA fragment during library amplification with KAPA HiFi polymerase (KAPA Biosystems) to facilitate multiplexed exome capture and sequencing. Equal amounts of sample were pooled prior to overnight exome capture, approximately 16 hours, with a slightly modified version of IDT's xGen probe library; supplemental probes were added to capture regions of the genome well-covered by a previous capture reagent (NimbleGen VCRome) but poorly covered by the standard xGen probes. In total, n=38,997,831 bases were included in the targeted regions. Captured fragments were bound to streptavidin-coupled DYNABEADS® (Thermo Fisher Scientific) and non-specific DNA fragments removed through a series of stringent washes using the xGen Hybridization and Wash kit according to the manufacturer's recommended protocol (Integrated DNA Technologies). The captured DNA was PCR amplified with KAPA HiFi and quantified by qPCR with a KAPA Library Quantification Kit (KAPA Biosystems). The multiplexed samples were pooled and then sequenced using 75 base pair paired-end reads with two 10 base pair index reads on the Illumina NOVASEQ® 6000 platform using S2 flow cells.

Sequence Alignment, Variant Identification, and Genotype Assignment

Upon completion of sequencing, raw data from each Illumina NOVASEQ® run was gathered in local buffer storage and uploaded to the DNAnexus platform for automated analysis. After upload was complete, analysis began with the conversion of CBCL files to FASTQ-formatted reads and assigned, via specific barcodes, to samples using the bcl2fastq conversion software (Illumina Inc., San Diego, Calif.). Sample-specific FASTQ files, representing all the reads generated for that sample, were then aligned to the GRCh38 genome reference with BWA-mem. The resultant binary alignment file (BAM) for each sample contained the mapped reads' genomic coordinates, quality information, and the degree to which a particular read differed from the reference at its mapped location. Aligned reads in the BAM file were then evaluated to identify and flag duplicate reads with the Picard MarkDuplicates tool (world wide web at "picard.sourceforge.net"), producing an alignment file (duplicatesMarked.BAM) with all potential duplicate reads marked for exclusion in downstream analyses.

GVCF files, including variant calls, were then produced on each individual sample using the WeCall variant caller (world wide web at "github.com/Genomicsplc/wecall") from Genomics PLC, identifying both SNVs and INDELs as compared to the reference. Additionally, each GVCF file carried the zygosity of each variant, read counts of both reference and alternate alleles, genotype quality representing the confidence of the genotype call, and the overall quality of the variant call at that position.

Upon completion of variant calling, individual sample BAM files were converted to fully lossless CRAM files using samtools. Metric statistics were captured for each sample to evaluate capture, alignment, insert size, and variant calling quality, using Picard (world wide web at "picard.sourceforge.net"), bcftools (world wide web at "samtools.github.io/bcftools"), and FastQC (world wide web at "bioinformatics.babraham.ac.uk/projects/fastqc").

Following completion of sample sequencing, samples showing disagreement between genetically-determined and reported sex (n=15), high rates of heterozygosity/contamination (D-stat>0.4) (n=7), low sequence coverage (less than 85% of targeted bases achieving 20× coverage) (n=1), or genetically-identified sample duplicates (n=14), and WES variants discordant with genotyping chip (n=9) were excluded. Six samples failed quality control in multiple categories, resulting in 38 individuals being excluded. The remaining 49,960 samples were then used to compile a project-level VCF (PVCF) for downstream analysis. The PVCF was created using the GLnexus joint genotyping tool. Care was taken to carry all homozygous reference, heterozygous, homozygous alternate, and no-call genotypes into the project-level VCF. An additional filtered PVCF, 'Goldilocks', was also generated. In the filtered Goldilocks PVCF, samples carrying SNP variant calls in the single sample pipeline or a DP<7 were converted to 'No-Call'. After the application of the DP filter, sites where all remaining samples were called as Heterozygous and all samples have an AB<85% ref/15% alt were excluded. Samples carrying INDEL variant calls in the single sample pipeline with a DP<10 were converted to 'No-Call'. After the application of the DP filter, sites where all remaining samples were called as Heterozygous and all samples have an AB<80% ref/20% alt were excluded. Multi-allelic variant sites in the PVCF file were normalized by left-alignment and represented as bi-allelic.

Phenotype Definition

ICD10-based cases required one or more of the following: a primary diagnosis or a secondary diagnosis in in-patient Health Episode Statistics (HES) records. ICD10-based excludes had primary or secondary diagnosis in the code range. ICD10-based controls were defined as those individuals that were not cases or excludes. Custom phenotype definitions included one or more of the following: ICD-10 diagnosis, self-reported illness from verbal interview and doctor-diagnosed illness from online-follow-up, touch-screen information. Quantitative traits (such as, physical measures, blood counts, cognitive function tests, and imaging derived phenotypes) were downloaded from UK Biobank (UKB) repository and spanned one or more visits. In total, 1,073 binary traits with case count 50 and 669 number of quantitative traits, were tested in WES association analyses.

Annotation of Predicted Loss-of-Function (LOF) Variants

Variants were annotated using snpEff and gene models from Ensembl Release 85. A comprehensive and high quality transcript set was obtained for protein coding regions which included all protein coding transcripts with an annotated Start and Stop codon from the Ensembl gene models. Variants annotated as stop_gained, start_lost, splice_donor, splice_acceptor, stop_lost and frameshift are considered to be LOF variants.

A recent large-scale study of genetic variation in 141,456 individuals provides a catalog of LOF variants. A direct comparison to this data is difficult due to numerous factors such as differences in exome sequencing capture platforms, variant calling algorithms and annotation. Additionally, the number of individuals and the geographic distribution of ascertainment (and thus genetic diversity) in the NFE subset of gnomAD may be larger than that of UK Biobank with WES in this report. Nonetheless, the gnomAD exome sites labeled as "PASS" from gnomAD r2.1 were annotated using the annotation pipeline. Data from gnomAD were lifted over to HG38 using Picard LiftoverVcf. The data was subset to Non-Finnish Europeans (NFE) (n=56,885 samples), individuals) restricted to variants with $MAF_{NFE}<1\%$ and obtained 261,309 LOFs in any transcript in 17,951 genes. Restricting LOFs only to those that are present in all transcripts, 175,162 LOFs were observed in 16,462 genes. 134,745 LOFs were observed in all transcripts of genes in UKB participants with WES of European ancestry.

Methods for LOF Burden Association Analysis

Burden tests of association were performed for rare LOFs within 49,960 individuals of European ancestry. For each gene region as defined by Ensembl. LOFs with MAF≤0.01 were collapsed such that any individual that is heterozygous for at least one LOF in that gene region is considered heterozygous, and only individuals that carry two copies of the same LOF are considered homozygous. Rare variants were not phased, and so compound heterozygotes are not considered in this analysis.

For each gene region, 668 rank-based inverse normal transformed (RINT) quantitative measures (including all subjects and sex-stratified models) with ≥5 individuals with non-missing phenotype information were assessed using an additive mixed model implemented in BOLT-LMM v2. Prior to normalization, traits were first transformed as appropriate (log 10, square) and adjusted for a standard set of covariates including age, sex, study site, first four principal components of ancestry, and in some cases BMI and/or smoking status. Data-points greater than five median absolute deviations from the median were excluded as outliers prior to normalization. 1,073 discrete outcomes (including all subjects and sex-stratified models) with 50 cases were assessed with covariate adjustment for age, sex and first four principle components of ancestry using a generalized mixed model implemented in SAIGE. For each quantitative and discrete trait included in the analysis, only gene regions in which >3 LOF carriers with non-missing phenotype and covariate information were evaluated.

Positive controls were systematically defined using a two-step approach. First, each gene for relevant disease, trait, biological, or functional evidence was annotated using publicly available resources including OMIM, NCBI Med-Gen, and the NHGRI-EBI GWAS catalogue. Genes with supporting evidence from at least one source, were then manually curated using NCBI PubMed to verify the relationship between the trait and LOF variants in the gene of interest. Genes with locus-level support for the trait of interest or related phenotype(s) in the GWAS catalog but lacking clear supporting evidence for a LOF association are reported herein as novel LOF associations.

Methods for Single Variant LOF Association Analysis

Single variant association analysis was performed using the same methods as described in the methods section for burden association analysis. For gene-trait associations with $p<10^{-7}$, single variant association statistics was calculated with the phenotype of interest for all LOFs included in the burden test that are observed with a minor allele count 5 in the 49,960 European ancestry individuals with WES. Association statistics for these variants are reported in Extended Data (ExtData_SingleVariantLOFs_V1.xlsx).

P-VAL Leave-One-Out (LOO) Burden is the p-value of the absence/presence test excluding the variant being tested. Delta P-Val Burden is the ratio of the p-value in the drop-one-out analysis compared to the burden test using all 65 variants. Burden summary statistics using all 65 variants in unrelated individuals: B=1.44, SE=0.26, p-value=3.12E-08, cMAF=0.00174, cMAC=152, cMAF_cases=0.0066, cMAC_cases=17, cMAF_controls=0.0016, cMAC_cases=135. Stepwise logistic regression selected 11/65 variants (AIC 11451). Burden summary statistics using the 11 variants: B=3.71, SE=0.437, p-value<2e-16, cMAF=0.0003, cMAC=22, cMAF_cases=0.005, cMAC_cases=12, cMAF_controls=0.0001, cMAC_controls=10. When analysis is restricted to variants with MAC>1, stepwise logistic regression selects 5/13 variants (AIC 11484). Burden summary statistics using the 5 variants: B=3.02, SE=0.53, p-value=8.92e-09.

LD (r2) across the 11 pLOF variants selected by stepwise regression for PIEZO1 and a positive control (16: 88835545_G_A; highlighted in green) reported in the literature for PIEZO1. None of these 12 variants are in LD, R2>0.01. When the burden test is adjusted for the previously reported variant rs2911463 (16:88835545_G_A), the burden test p-value remains <2E-16 (AIC 11,444), which indicates that the burden is not tagging the reported variant.

Example 2: Demographics and Clinical Characteristics of Sequenced Participants

A total of 50,000 participants were selected, prioritizing individuals with more complete phenotype data: those with whole body MRI imaging data from the UK Biobank Imaging Study, enhanced baseline measurements, hospital episode statistics (HES), and/or linked primary care records (which will soon be available to approved researchers). During data generation, samples from 40 participants were excluded due to failed quality control measures or participant withdrawal, resulting in a final set of 49,960 individuals. Overall, the sequenced sample is representative of the 500,000 UKB participants (Table 1). There were no notable differences in age, sex, or ancestry between the sequenced sample and overall study population. Sequenced participants were more likely to have HES diagnosis codes (84.2% among sequenced vs. 77.3% overall) and enhanced measures (Table 1).

TABLE 1

| Clinical characteristics in whole exome sequenced and all UK Biobank participants | | |
|---|---|---|
| Basic Demographics and Clinical Characteristics | UKB 50k WES Participants | UKB 500k Participants |
| N | 49,960 | 502,543 |
| Female, n(%) | 27,243 (54) | 273,460 (54) |
| Age at assessment, years | 58 (45-71) | 58 (45-71) |
| Body mass index, kg/m$^2$ | 26 (21-31) | 26 (21-31) |
| Number of imaged participants | 12,075[b] | 21,407[a] |
| Number of current/past smokers, n(%) | 17,515 (35) | 216,482 (43) |
| Townsend Deprivation Index | −2.0 (−6.1, −2.1) | −2.13 (−6.2, −1.97) |
| Inpatient ICD10 codes per patient | 5 | 5 |
| Patients with >=1 ICD10 diagnoses (%) | 84.2 | 78.0 |
| Genetic Ancestry Assignment[c] | | |
| African (%) | 1.49 | 1.24 |
| East Asian (%) | 0.54 | 0.51 |
| European (%) | 93.66 | 94.55 |
| Cardiometabolic phenotypes | | |
| Coronary Disease, n(%) | 3,3340 (6.6) | 35,879 (7.1) |
| Heart Failure, n(%) | 300 (0.6) | 4,399 (0.8) |
| Type 2 Diabetes, n(%) | 1,541 (3.0) | 17,261 (3.4) |
| Respiratory and immunological phenotypes | | |
| Asthma, n(%) | 8,250 (16) | 68,149 (13) |
| COPD, n(%) | 741 (1.4) | 7,438 (1.4) |
| Rheumatoid Arthritis, n(%) | 710 (1.4) | 7,337 (1.4) |
| Inflammatory Bowel Disease n(%) | 543 (1.0) | 5,783 (1.1) |
| Neurodegenerative phenotypes | | |
| Alzheimer's Disease, n(%) | 13 (0.05) | 320 (0.06) |
| Parkinson's Disease, n(%) | 65 (0.13) | 1,043 (0.2) |
| Multiple Sclerosis, n(%) | 126 (0.25) | 1,352 (0.26) |
| Myasthenia Gravis, n(%) | 14 (0.02) | 217 (0.04) |
| Oncology phenotypes | | |
| Breast Cancer, n(%) | 1,667 (3.3) | 16,887 (3.3) |
| Ovarian Cancer, n(%) | 162 (0.3) | 1,777 (0.3) |
| Pancreatic Cancer, n(%) | 602 (1.2) | 4,611 (0.9) |
| Prostate Cancer, n(%) | 848 (1.6) | 8,855 (1.7) |
| Melanoma, n(%) | 598 (1.1) | 5,715 (1.1) |

TABLE 1-continued

Clinical characteristics in whole exome sequenced and all UK Biobank participants

| Basic Demographics and Clinical Characteristics | UKB 50k WES Participants | UKB 500k Participants |
|---|---|---|
| Enhanced measures | | |
| Hearing test available, n(%) | 40,546 (81.1) | 167,011 (33.2) |
| Pulse Rate, n(%) | 40,548 (34.2) | 170,761 (33.9) |
| Visual Acuity Measured, n(%) | 39,461 (78.9) | 117,092 (23.2) |
| IOP measured (left), n(%) | 37,940 (75.9) | 111,942 (22.2) |
| Autorefraction, n(%) | 36,067 (72.1) | 105,989 (21.0) |
| Retinal OCT, n(%) | 32,748 (65.5) | 67,708 (13.4) |
| ECG at rest, n(%) | 10,829 (27.1) | 13,572 (2.1) |
| Cognitive Function, n(%) | 9,511 (19.0) | 96,362 (19.1) |
| Digestive Health, n(%) | 13,553 (28.1) | 142,310 (28.3) |
| Physical Activity Measurement, n(%) | 10,684 (21.3) | 101,117 (20.1) |

Figure 3:
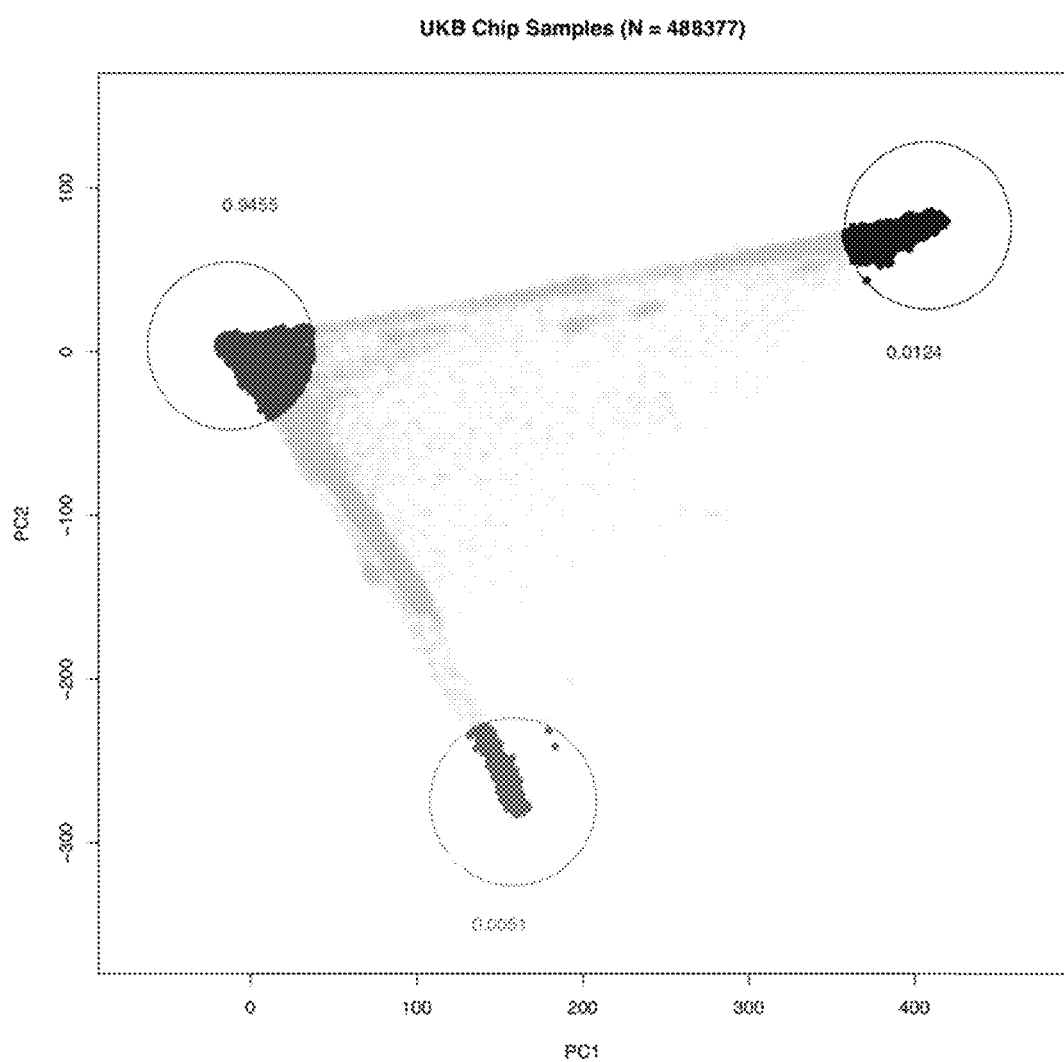
FIG. 3 shows continental ancestry in UK Biobank 500k and 50k; principal component 1 and 2 for n=488,377 individuals available from the UK Biobank Data Showcase; three pre-defined regions of a plot of represent African (blue), East Asian (green), and European (red) ancestry.
Figure 3:
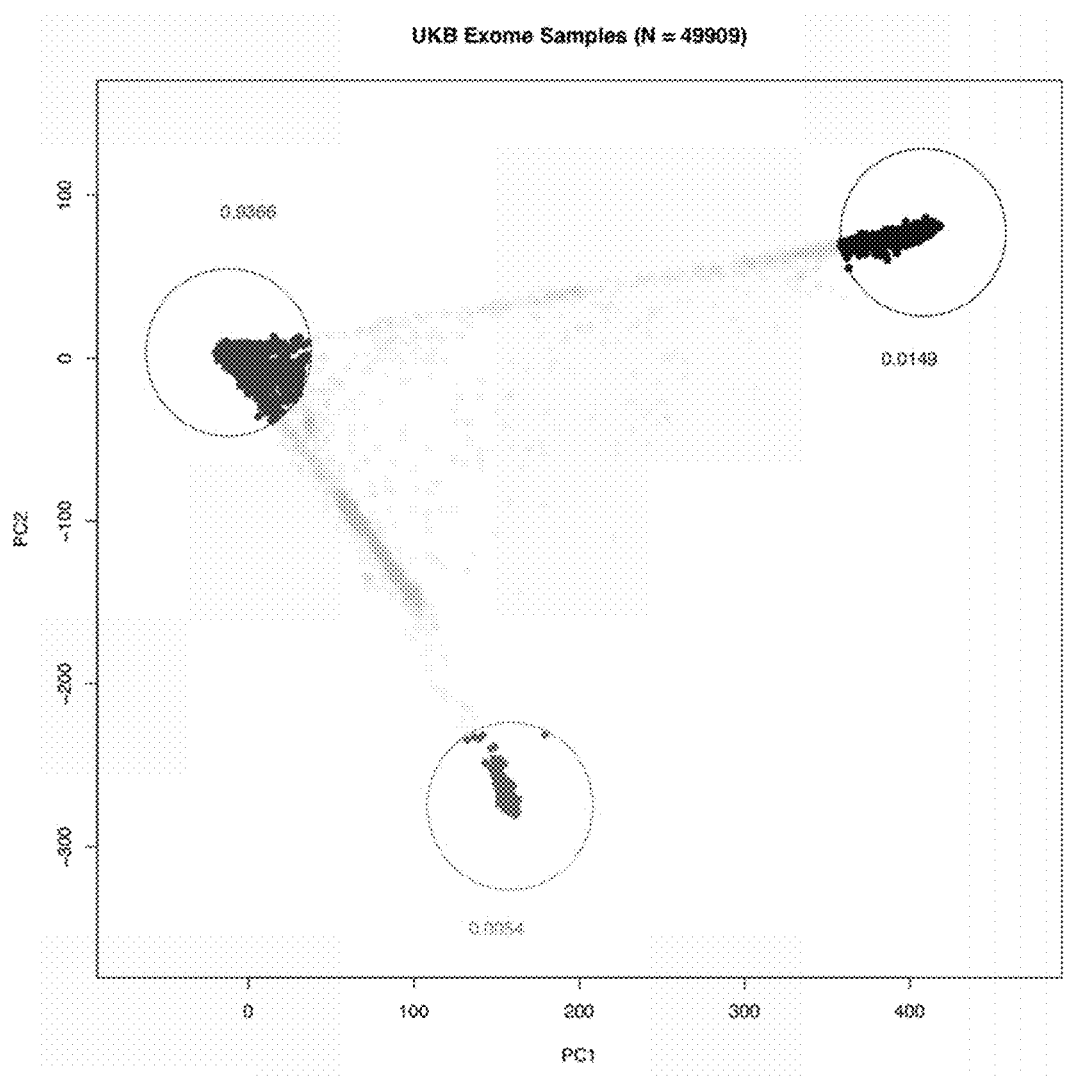

[a] The number of samples with at least one non-missing image derived phenotype value from data downloaded from UK Biobank in November 2018.
[b] The number of samples with exome sequencing data and at least one non-missing image derived phenotype value from data downloaded from UK Biobank in November 2018.
[c] Number of samples in 3 pre-defined regions of a plot of the first two genetic principal component scores, where the regions are selected to represent African, East Asian, and European ancestry (see, FIG. 3).

Participants with WES with at least one HES diagnosis code did not differ from non-sequenced participants in the median number of primary and secondary ICD10 codes or broad phenotype distributions, other than codes for asthma (ICD10 J45) and status asthmaticus (ICD10 J46), as the most enriched in sequenced samples, and senile cataract (ICD10 H25) and unknown and unspecified causes of morbidity (ICD10 R69), as the most depleted. The sequenced subset includes 194 parent-offspring pairs, 613 full-sibling pairs, 1 monozygotic twin pairs and 195 second degree relationships. The distribution of relatedness between pairs of individuals in UKB WES are included in FIG. 1.

Example 3: Summary and Characterization of Coding Variation from WES

Figure 2:
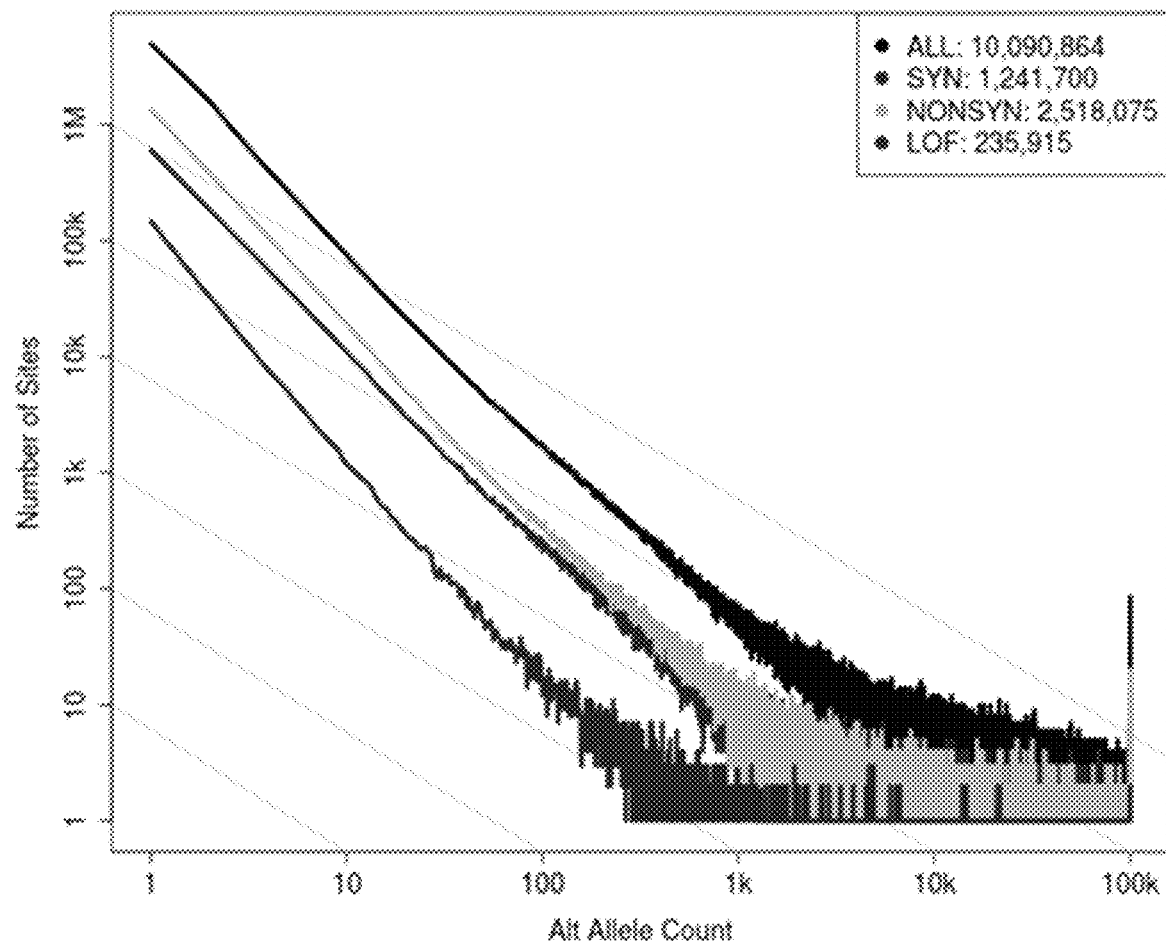
FIG. 2 shows an observed site frequency spectrum (SFS) for all autosomal variants and by functional prediction; UKB 50k exomes were down-sampled at random to the number of individuals specified on the horizontal axis; the number of genes containing at least the indicated count of LOFs AAF<1% as in the legend are plotted on the vertical axis; the maximum number of autosomal genes is 18,272.

The protein coding regions and exon-intron splice sites of 19,467 genes were targeted. Counts of autosomal variants observed across all individuals by type/functional class for all and for MAF<1% frequency. All variants passed QC criteria, individual and variant missingness <10%, and Hardy Weinberg p-value >$10^{-15}$. Median count of variants and interquartile range (IQR) for all variants and for MAF<1%. The average proportion of targeted bases (n=38, 997,831) achieving at least 20× coverage in each sample was 94.6% (standard deviation 2.1%). 10,028,025 single nucleotide and indel variants were observed after quality control, 98.5% with minor allele frequency (MAF)<1% (Table 2). Of the total variants, 3,995,785 are within targeted regions. These variants included 2,431,680 non-synonymous (98.9% with MAF<1%), 1,200,882 synonymous (97.8% with MAF<1%), and 205,867 predicted loss of function (pLOF) variants affecting at least one coding transcript (initiation codon loss, premature stop codons, splicing, and frameshifting indel variants; 99.7% with MAF<1%) (FIG. 2). The tally of 9,403 synonymous (IQR 125), 8,369 non-synonymous (IQR 132) and 161 pLOF variants (IQR 14) per individual (median values) is comparable to previous exome sequencing studies. If the analysis is restricted to pLOF variants that affect all transcripts for a gene, the number of pLOF variants drops to 140,850 overall and 96 per individual (a reduction of about 31.6% and about 40.4%, respectively), consistent with previous studies.

TABLE 2

Summary statistics for variants in sequenced exomes of 49,960 UKB participants

| | WES in n = 49,960 autosomes | | Median Per Participant (IQR) | |
|---|---|---|---|---|
| | # Variants | # Variants MAF <1% | # Variants | # Variants MAF <1% |
| Total | 10,028,025 | 9,882,400 | 49,000 (628) | 1,626 (133) |
| Targeted Regions | 3,995,785 | 3,941,162 | 18,670 (235) | 640 (56) |
| Variant Type | | | | |
| SNVs | 3,823,276 | 3,770,454 | 18,404 (233) | 613 (54) |
| Indels | 142,603 | 141,439 | 266 (16) | 21 (25) |
| Multi-Allelic | 466,433 | 459,434 | 2,304 (50) | 84 (15) |
| Functional Prediction | | | | |
| Synonymous | 1,200,882 | 1,175,279 | 9,403 (125) | 222 (26) |
| Missense | 2,431,680 | 2,406,367 | 8,369 (132) | 367 (38) |
| pLOF (any transcript) | 205,867 | 205,215 | 161 (14) | 20 (7) |
| pLOF (all transcripts) | 140,850 | 140,445 | 96 (10) | 14 (6) |

Example 4: Phenotypic Associations with LOF Variation

The combination of WES and rich health information allows for broad investigation of the phenotypic consequences of human genetic variation. LOF variation can yield tremendous insights into gene function; however, imputed datasets are missing the majority of such variation. WES is well-suited to identify LOF variants and to evaluate their phenotypic associations. Gene burden tests of associations for rare (AAF<1%) pLOF variants (pLOF variants identified in WES across all genes with >3 pLOF variant carriers) were conducted with 1,741 traits (1,073 discrete traits with at least 50 case counts defined by hospital episode statistics and self-report data, 668 quantitative, anthropometric, and blood traits) in n=46,979 individuals of primarily European ancestry. For each gene-trait association, the strength of association for the pLOF gene burden test was also compared to the association results for each of the SNVs included in the burden test.

Example 5: LOF Associations and Novel Gene Discovery le;.4qIn the pLOF gene burden association analysis, a novel association between PIEZO1 LOFs (cumulative allele frequency=0.2%) and greatly increased risk for varicose veins was identified. Results for PIEZO1 for the binary phenotype of asymptomatic varicose veins of lower extremities within the UKB 50k exome and UKB 150k exome are shown in Table 3.

TABLE 3

PIEZO1 LOF gene burden associations

| Exome | Counts RR\|RA\|AA | OR (95% CI) | Burden P | NSNV | Lowest P SNV |
|---|---|---|---|---|---|
| UKB 50k | Ctrls: 43285\|142\|0 | 4.9 (3.1, 7.8) | $2.7 \times 10^{-8}$ | 65 | 2.29E-3 |

TABLE 3-continued

PIEZO1 LOF gene burden associations

| Exome | Counts RR\|RA\|AA | OR (95% CI) | Burden P | NSNV | Lowest P SNV |
|---|---|---|---|---|---|
| UKB 150k | Cases: 1267\|20\|0 Ctrls: 131514\|443\|0 Cases: 3559\|36\|0 | 3.0 (2.1, 4.4) | $1.8 \times 10^{-8}$ | | |

This finding is driven by a burden of rare LOF variants, with the most significant PIEZO1 single variant LOF association in the UKB 50k exome achieving a p-value of $2.29 \times 10^{-3}$. Leave one out analyses of the UKB 50k exome indicate no single variant accounts for the entire signal and step-wise regression analyses indicated that 11 separate variants (5 of which had MAC>1) were contributing to the overall burden signal (FIG. 4).

This finding was replicated in 2,953 varicose veins cases and 75,694 controls previously exome sequenced (OR=2.7, $p=1.86 \times 10^{-9}$). This region had previously been implicated by common non-coding variants with small effects on disease risk, where rs2911463 and other nearby common variants on chromosome 16 have recently been associated with varicose veins (frequency=0.69, OR=0.996, p-value=$1.0 \times 10^{-27}$ in GWAS of 408,455 genotyped U.K. Biobank participants). The rs2911463 variant is not in LD with any of the key variants identified (FIG. 5) and the burden test remains significant when adjusting for rs2911463.

What is claimed is:

1. A method of treating a patient with a therapeutic agent that treats or inhibits varicose veins, wherein the patient is suffering from varicose veins, the method comprising the steps of:
   determining whether the patient has a Piezo Type Mechanosensitive Ion Channel Component 1 (PIEZO1) predicted loss-of-function variant nucleic acid molecule which is a PIEZO1 genomic nucleic acid molecule, or an mRNA molecule produced therefrom, or a cDNA molecule produced from the mRNA molecule, wherein the PIEZO1 predicted loss-of-function variant is selected from 16:88715629:G:A, 16:88715728:G:T, 16:88715767:G:A, 16:88715802:C:A, 16:88715822:D:4, 16:88715987:I:1, 16:88716359:A:G, 16:88716570:C:T, 16:88716874:G:A, 16:88717213:T:A, 16:88719588:G:A, 16:88719722:C:G, 16:88719870:G:T, 16:88720068:D:2, 16:88720229:C:A, 16:88720248:D:4, 16:88720394:C:T, 16:88720644:D:1, 16:88720698:D:1, 16:88720698:I:1, 16:88721165:C:A, 16:88721268:D:1, 16:88721307:G:A, 16:88721586:G:C, 16:88721652:G:C, 16:88722217:C:T, 16:88722605:I:1, 16:88723005:I:7, 16:88723253:G:A, 16:88723311:C:T, 16:88725081:C:A, 16:88726282:G:A, 16:88726546:C:T, 16:88726619:G:A, 16:88726924:G:A, 16:88727038:C:T, 16:88727072:D:1, 16:88727163:G:A, 16:88731768:D:1, 16:88732334:C:G, 16:88732411:D:1, 16:88732720:D:1, 16:88733326:G:C, 16:88733337:D:4, 16:88733587:C:A, 16:88733965:D:1, 16:88734017:C:A, 16:88734042:I:1, 16:88734679:C:T, 16:88734909:I:1, 16:88736167:D:2, 16:88736324:G:A, 16:88736391:G:T, 16:88736409:C:T, 16:88736671:G:A, 16:88737557:A:C, 16:88737727:C:G, 16:88737815:C:T, 16:88738283:G:C, 16:88738637:G:A, 16:88738735:D:1, 16:88741477:C:T, 16:88742306:D:1, 16:88749399:G:A, and/or 16:88784929:C:T by:
   obtaining or having obtained a biological sample from the patient; and
   performing or having performed a genotyping assay on the biological sample to determine if the patient has a genotype comprising the PIEZO1 predicted loss-of-function variant nucleic acid molecule; and
   administering or continuing to administer to the patient identified as a PIEZO1 reference patient the therapeutic agent that treats or inhibits varicose veins in a standard dosage amount for the PIEZO1 reference patient; and
   administering or continuing to administer to the patient who carries heterozygous or homozygous PIEZO1 predicted loss-of-function variant nucleic acid molecule the therapeutic agent that treats or inhibits varicose veins in an amount that is greater than the standard dosage amount for the PIEZO1 reference patient;
   wherein the presence of the heterozygous or homozygous loss-of-function variant in the PIEZO1 nucleic acid molecule associates with a burden for developing varicose veins.

2. The method according to claim 1, wherein the genotyping assay is carried out in vitro.

3. The method according to claim 1, wherein the genotyping assay comprises sequencing a portion of the nucleotide sequence of the PIEZO1 nucleic acid molecule in the biological sample, wherein the sequenced portion comprises a position corresponding to a predicted loss-of-function variant position.

4. The method according to claim 1, wherein the genotyping assay comprises:
   a) contacting the biological sample with a primer hybridizing to a portion of the nucleotide sequence of the PIEZO1 nucleic acid molecule that is proximate to a predicted loss-of-function variant position;
   b) extending the primer through the predicted loss-of-function variant position; and
   c) determining whether the extension product of the primer comprises a variant nucleotide at the predicted loss-of-function variant position.

5. The method according to claim 3, wherein the genotyping assay comprises sequencing the entire PIEZO1 nucleic acid molecule.

6. The method according to claim 1, wherein the genotyping assay comprises:
   a) amplifying a portion of the PIEZO1 nucleic acid molecule that encodes the human PIEZO1 polypeptide, wherein the portion comprises a predicted loss-of-function variant position;
   b) labeling the amplified nucleic acid molecule with a detectable label;
   c) contacting the labeled nucleic acid molecule with a support comprising an alteration-specific probe, wherein the alteration-specific probe comprises a nucleotide sequence which hybridizes under stringent conditions to the predicted loss-of-function variant position; and
   d) detecting the detectable label.

7. The method according to claim 6, wherein the PIEZO1 nucleic acid molecule in the biological sample is mRNA and the mRNA is reverse-transcribed into a cDNA prior to the amplifying step.

8. The method according to claim 1, wherein the genotyping assay comprises:
   contacting the PIEZO1 nucleic acid molecule in the biological sample with an alteration-specific probe comprising a detectable label, wherein the alteration-specific probe comprises a nucleotide sequence which hybridizes under stringent conditions to a PIEZO1 predicted loss-of-function variant position; and
   detecting the detectable label.

\* \* \* \* \*